(12) United States Patent
Day

(10) Patent No.: US 11,996,179 B2
(45) Date of Patent: May 28, 2024

(54) METHOD AND SYSTEM FOR DISEASE CONDITION REPROGRAMMING BASED ON PERSONALITY TO DISEASE CONDITION MAPPING

(71) Applicant: GenoEmote LLC, Bellevue, WA (US)

(72) Inventor: Alexandrea Lauren Day, Bellevue, WA (US)

(*) Notice: Subject to any disclaimer, the term of this patent is extended or adjusted under 35 U.S.C. 154(b) by 10 days.

(21) Appl. No.: 17/941,533

(22) Filed: Sep. 9, 2022

(65) Prior Publication Data

US 2023/0071994 A1    Mar. 9, 2023

Related U.S. Application Data

(60) Provisional application No. 63/264,803, filed on Dec. 2, 2021, provisional application No. 63/261,037, filed on Sep. 9, 2021.

(51) Int. Cl.
*G16H 20/70*    (2018.01)
*A61B 5/00*    (2006.01)
(Continued)

(52) U.S. Cl.
CPC ........... *G16H 20/70* (2018.01); *A61B 5/0022* (2013.01); *A61B 5/0205* (2013.01); *A61B 5/164* (2013.01);
(Continued)

(58) Field of Classification Search
CPC ........ G16H 20/70; G16H 10/20; G16H 40/63; G16H 40/67; G16H 50/70; G16H 50/20;
(Continued)

(56) References Cited

U.S. PATENT DOCUMENTS 11,291,796 B2    4/2022    Li
2006/0047538 A1    3/2006    Condurso et al.
(Continued)

FOREIGN PATENT DOCUMENTS

CN    104856704    8/2015
CN    107307865    11/2017
(Continued)

OTHER PUBLICATIONS

Jovanovic et al., "Intelligent interactive technologies for mental health and well-being", Artificial Intelligence: Theory and Applications, 2021•Springer (Year: 2021).*
(Continued)

*Primary Examiner* — Qian Yang
(74) *Attorney, Agent, or Firm* — Hassan Abbas Shakir; Shakir Law PLLC

(57) ABSTRACT

An emotional or mental belief system reprogramming system is disclosed. The system includes a digital framework including a pattern recognition module configured to identify and recommend reprogramming and alter a health status of a user, the digital framework includes (1) a digitally recorded library of human emotions, unconscious agendas, perceptions, beliefs, and mindsets of a control group of users selected from a population of users (2) a question engine configured to interrogate the user using a library of predetermined questions and to identify a plurality of underlying unconscious agendas of the user that generate behavior of the user and associated negative emotions of the user, (3) an expressive, experiential digital agent having digitized color, gestures, expressions, movements, emotions, beliefs, intent, intuition, and haptic effects, the digital agent configured to interact with the user in real time, to ask questions, to engage the user.

27 Claims, 18 Drawing Sheets

(51) Int. Cl.

| | |
|---|---|
| *A61B 5/0205* | (2006.01) |
| *A61B 5/16* | (2006.01) |
| *A61M 21/02* | (2006.01) |
| *G06V 40/16* | (2022.01) |
| *G06V 40/20* | (2022.01) |
| *G06V 40/70* | (2022.01) |
| *G16H 10/20* | (2018.01) |
| *G16H 40/63* | (2018.01) |
| *G16H 40/67* | (2018.01) |
| *G16H 50/70* | (2018.01) |
| *H04M 1/72448* | (2021.01) |
| *A61B 5/021* | (2006.01) |
| *A61B 5/024* | (2006.01) |
| *A61M 21/00* | (2006.01) |
| *G06V 40/10* | (2022.01) |

(52) U.S. Cl.
CPC ............ *A61B 5/165* (2013.01); *A61B 5/4842* (2013.01); *A61B 5/7264* (2013.01); *A61B 5/7267* (2013.01); *A61B 5/7275* (2013.01); *A61B 5/742* (2013.01); *A61M 21/02* (2013.01); *G06V 40/174* (2022.01); *G06V 40/20* (2022.01); *G06V 40/70* (2022.01); *G16H 10/20* (2018.01); *G16H 40/63* (2018.01); *G16H 40/67* (2018.01); *G16H 50/70* (2018.01); *H04M 1/72448* (2021.01); *A61B 5/021* (2013.01); *A61B 5/024* (2013.01); *A61M 2021/0027* (2013.01); *A61M 2021/005* (2013.01); *A61M 2205/3584* (2013.01); *A61M 2205/52* (2013.01); *A61M 2230/30* (2013.01); *G06F 2203/011* (2013.01); *G06V 40/15* (2022.01)

(58) Field of Classification Search
CPC ..... A61B 5/0022; A61B 5/0205; A61B 5/164; A61B 5/165; A61B 5/4842; A61B 5/7264; A61B 5/7267; A61B 5/7275; A61B 5/742; A61B 5/021; A61B 5/024; A61B 5/4836; A61M 21/02; A61M 2021/0027; A61M 2021/005; A61M 2205/3584; A61M 2205/52; A61M 2230/30; A61M 2021/0022; A61M 2205/3303; A61M 2205/3317; A61M 2205/3375; A61M 2205/3553; A61M 2205/3592; A61M 2205/507; A61M 2205/581; A61M 2205/582; A61M 2205/584; A61M 2205/609; A61M 2205/8212; A61M 2230/06; A61M 2230/10; A61M 2230/63; A61M 2230/65; A61M 21/00; A61M 2205/505; G06V 40/174; G06V 40/20; G06V 40/70; G06V 40/15; H04M 1/72448; G06F 2203/011; G06F 18/40

See application file for complete search history.

(56) References Cited

U.S. PATENT DOCUMENTS

| | | | |
|---|---|---|---|
| 2018/0218238 A1* | 8/2018 | Viirre | ................ G06N 5/01 |
| 2019/0122667 A1* | 4/2019 | Andersen | ............... G06F 40/30 |
| 2019/0306093 A1 | 10/2019 | Schilling et al. | |
| 2020/0251211 A1* | 8/2020 | McKinney | .............. G06F 3/011 |
| 2020/0367798 A1* | 11/2020 | Frolov | .................... A61B 5/165 |
| 2020/0373001 A1 | 11/2020 | Harrison et al. | |
| 2021/0182663 A1 | 6/2021 | Galuten | |
| 2021/0275078 A1 | 9/2021 | Leuthardt | |
| 2022/0200934 A1 | 6/2022 | Datta et al. | |

FOREIGN PATENT DOCUMENTS

| | | | |
|---|---|---|---|
| CN | 113208626 | | 8/2021 |
| KR | 102453173 B1 | | 1/2023 |
| WO | WO 2019/246239 | * | 12/2019 |
| WO | 2020257354 | | 12/2020 |
| WO | 2021026329 | | 2/2021 |
| WO | 2021125647 | | 6/2021 |

OTHER PUBLICATIONS

Office Action issued in U.S. Appl. No. 17/941,496 by the USPTO on Dec. 20, 2023, 22 pgs.
Office Action issued in U.S. Appl. No. 18/383,026 by the USPTO on Dec. 14, 2023, 6 pgs.

* cited by examiner

METHOD AND SYSTEM FOR DISEASE CONDITION REPROGRAMMING BASED ON PERSONALITY TO DISEASE CONDITION MAPPING

CROSS-REFERENCES TO RELATED APPLICATIONS

This application claims the benefit of and priority to U.S. Provisional Application No. 63/261,037, Titled "SYSTEMS AND METHODS FOR A TRUTH-DETECTION THERAPY ASSISTANT USING BIOMETRIC SENSORS AND MACHINE LEARNING TO FACILITATE MAPPING OF SPECIFIC UNCONSCIOUS AGENDAS TO SPECIFIC DISEASE CONDITIONS" and filed on Sep. 9, 2021, which is hereby incorporated by reference in its entirety for all purposes, and U.S. Provisional Application No. 63/264,803, Titled "EXPRESSIVE, EXPERIENTIAL, CROSS-PLATFORM, AUTO-MORPHING (ADAPTING) METAVERSE AVATAR WITH COMMUNICATION ATTRIBUTES USING SENSORS AND COLOR SIGNATURES MAPPED TO WORDS, THE MEANING AND FEELING OF WORDS, USING MACHINE LEARNING AS INFORMED BY INTENT" and filed on Dec. 2, 2021, which is hereby incorporated by reference in its entirety for all purposes.

TECHNICAL FIELD

The present invention relates generally to an emotional or mental belief system reprogramming system that includes a digital framework. Specifically, the digital framework includes a pattern recognition module configured to identify and recommend reprogramming and alter an emotional or mental state of a user.

BACKGROUND OF THE INVENTION

Examples of the present disclosure describes systems and methods for creating software and/or hardware to assist therapists in their work with patients and to help users during self-therapy, by identifying unconsciously-held agendas that impact health and well-being, using machine learning to validate the line of questioning by the therapist, chatbot (etc.), of the patient. Therapy is a process where little is known consciously so a method to access the unconscious where answers about self are known is needed. Therefore, this invention is to provide access to unconscious agendas in the unconscious that determine what emotions are experienced consciously and what disease could result. Previously, no one has attempted to map disease conditions to emotions. But today, there is an empirical method to prove that a specific emotion is a risk factor for a specific disease. This invention is intended to discover, map, and validate that emotions can effect health or illness, by measuring changes in gene expression. While this statement makes it sound simple, it is not and requires a number of steps to accomplish the goal.

To understand this discussion, it is appropriate to teach the reader about the current state of the mental and physical healthcare systems and the frustrations that doctors, therapists, and patients experience because many questions continue to go unanswered. From the patient's perspective, "Why am I sick? What can I do to feel better? Can anyone help me?" The inability of a doctor to help if there is no pathology exacerbates the problem. And mental health therapists are not often sought for physical problems, so hence the huge gap within the helping professions for mental and physical healthcare.

Research has revealed that 90% of doctor visits are stress-related and do not result in any positive test results which means there is no diagnosis and no disease. But the patient feels ill and wants to know how to feel better. As a result, the talent and time of physicians is wasted and ends up frustrated not being able to help because he/she has no training to address stressed-related maladies (aches, pains, headaches, nausea, etc.). Mental healthcare is not remarkably successful either with physical problems and it's prohibitively expensive. There are many different methods and processes to choose from as well which adds to the confusion. The most effective method, proven by research has been determined to be Cognitive-behavioral therapy and its different flavors however, patients need more direction to get referred to a therapist when their aches and pains are not diagnoseable by a physician.

In genetic research it is known that there are a number of factors that cause DNA mutations and how they are expressed. Of course, there are inherited genes that could be expressed or are turned off, regressed. There are environmental factors that can cause disease such as smoking or pesticides that alter DNA or it's expression. Included within this "environmental" category is "stress." However, lowering stress does not come naturally to humans. In fact, our society is becoming more stressed which will result in more stress-related doctor visits, more people in therapy not getting as much help as they need—talking doesn't help for most people beyond 24-48 hours. And of course, disease conditions will increase. There is a deep need to identify what specific stressors (emotions) are causing what specific diseases. We must understand the relationship between body chemistry, biology, emotions and unconscious agendas (what we believe) and help people change their emotional risk factors that lead to disease, just like how smoking has been determined to cause cancer.

Negative emotions and the belief systems that produce them are also risk factors in every diagnosed disease. This is a tall statement but over 40 years and thousands of clients, it has been antidotally proven. We are undertaking scientific research now to provide evidence-based outcomes that match what we have already learned and based upon previous research that proves that changing one's outlook on life improves health and well-being. This is not new; it's simply a validation of what we know, scientifically with tools to measure with.

Finally, why does a therapist need a truth-detecting assistant? It's because most people do not have a grasp of how they feel, consciously nor do they particularly want to know. However, the unconscious is full of ideas, knows exactly how one feels and how to change the person's life to experience well-being, if they would only listen. Cognitive-behavioral therapy (CBT) being the most successful can be improved with this invention by assisting a therapist in the process, speeding up access to the unconscious drivers of negative behavior/emotions, and revealing the changes needed to improve not only mental health but stress levels, disease prevention and/or improvement of disease conditions.

CBT is conducted by a therapist helping a patient to identify negative thinking that produces negative emotions and undesired behavior and/or a disease condition. An example would be telling yourself you are just going to have one chocolate and before you know it you've eaten half the box. Then, you rationalize why you need to eat the rest, so no one will know you did that (behavior). A CBT therapist would ask you what feelings you are experiencing when you get caught up in this behavior. Thereafter would be a search, for a negative unconscious agenda to change, to stop the behavior. Support would be offered and recommended exercises to support the desired behavioral change.

However, the rub is—what consciously is discussed during a therapy session is typically not the core issue but a more surface reason, guessed by the conscious mind as the therapist questions the patient. Consciousness is a trickster and often denies it's behavior as being in their control. As a result, most people are not able to make real permanent change. This invention will not only identify the exact feeling felt when acting out an unwanted behavior, but also identify the unconscious agenda (belief system) to "reprogram" to change both the negative feeling and the unconscious agenda. This positively impacts the physical body, the mind, health outcomes and permanent behavioral change.

SUMMARY OF THE INVENTION

In one aspect, an emotional or mental belief system reprogramming system is disclosed. The system includes a digital framework including a pattern recognition module configured to identify and recommend reprogramming and alter a health status of a user, the digital framework includes (1) a digitally recorded library of human emotions, unconscious agendas, perceptions, beliefs, and mindsets of a control group of users selected from a population of users (2) a question engine configured to interrogate the user using a library of predetermined questions and to identify a plurality of underlying unconscious agendas of the user that generate behavior of the user and associated negative emotions of the user, (3) an expressive, experiential digital agent having digitized color, gestures, expressions, movements, emotions, beliefs, intent, intuition, and haptic effects, the digital agent configured to interact with the user in real time, to ask questions, to engage the user, and to direct the user to perform certain tasks, wherein the digital agent comprises a conversational digital avatar, and/or a conversational chatbot, (4) a plurality of sensors communicably connected to the digital framework and to the user during a question-answer session with a therapist, chatbot, avatar, coach, friend as a means of engaging the question engine, each of the plurality of sensors configured to communicate, record and report at least one of: a physiological state or an emotional state of the user while responding to a plurality of questions posed by the therapist, chatbot, avatar, coach, friend as a means of engaging the question engine during the question-answer session, (5) a baseline measuring module configured to evaluate the user's responses and reactions to the questions posed by the therapist, chatbot, avatar, coach, friend as a means of engaging the question engine, and to determine and differentiate between a valid answer and an invalid answer, and thereby to construct a baseline measure for the user, and (6) a reprogramming module configured to identify and recommend reprogramming of a plurality of negative beliefs of the user, accomplished through relaxation, breathing, recording and repeating a plurality of de-programming and reprogramming statements, confirmed as accurate, by the digital framework through an analysis of the plurality of sensors data in combination with the underlying unconscious agendas of the user.

In one aspect, a method of reprogramming a belief system of a user using a digital framework that includes a pattern recognition module, is disclosed. The method includes reprogramming and altering a mental or emotional state of a user using a digital framework comprising a pattern recognition module. The identifying, recommending for reprogramming and altering the health status of the user includes (1) interrogating the user using a question engine comprising a library of predetermined questions and identifying a plurality of underlying unconscious agendas of the user that generate behavior of the user and triggered by negative emotions of the user, (2) engaging an expressive, experiential digital agent having digitized color, gestures, expressions, movements, emotions, beliefs, intent, intuition, and haptic effects to interact with the user in real time, to ask questions, to engage the user, and direct the user to perform certain tasks, wherein the digital agent comprises a conversational digital avatar, and a conversational chatbot, (3) communicably connecting a plurality of sensors to the digital framework and to the user during a question-answer session with a therapist or the question engine, each of the plurality of sensors communicating, recording and reporting at least one of: a physiological state or an emotional state of the user while responding to a plurality of questions posed by the therapist, chatbot, avatar, coach, friend or the question engine during the question-answer session, and (4) evaluating the user's responses and reactions to the questions posed by the therapist, chatbot, avatar, coach, friend or the question engine using a baseline measuring module, determining and differentiating between a valid answer and an invalid answer, and thereby constructing a baseline measure for the user, (5) identifying and recommending reprogramming a plurality of negative beliefs of the user through relaxation, breathing, recording and repeating of a plurality of de-programming and reprogramming statements, confirmed as accurate, by the digital framework through an analysis of the plurality of sensors data in combination with the underlying unconscious agendas of the user.

In one aspect, a non-transitory machine-readable storage medium, includes instructions embodied thereon for reprogramming and altering a mental or emotional state of a user is disclosed. The instructions when executed using one or more computer processors causes the machine to perform identifying and recommending reprogramming and altering a a mental or emotional state of a user of a user using a digital framework comprising a pattern recognition module. The identifying and recommending reprogramming and altering the health status of the user includes (1) interrogating the user using a question engine comprising a library of predetermined questions and identifying a plurality of underlying unconscious agendas of the user that generate behavior of the user and, triggered by the negative emotions of the user, (2) engaging an expressive, experiential digital agent having digitized color, gestures, expressions, movements, emotions, beliefs, intent, intuition, and haptic effects to interact with the user in real time, to ask questions, to engage the user, and direct the user to perform certain tasks, wherein the digital agent comprises a conversational digital avatar, and a conversational chatbot, (3) communicably connecting a plurality of sensors to the digital framework and to the user during a question-answer session with a therapist or the question engine, each of the plurality of sensors communicating, recording and reporting at least one of: a physiological state or an emotional state of the user while responding to a plurality of questions posed by the therapist or the question engine during the question-answer session, (4) evaluating the user's responses and reactions to the questions posed by the therapist or the question engine using a baseline measuring module, determining and differentiating between a valid answer and an invalid answer, and thereby constructing a baseline measure for the user, and (5) identifying and recommending reprogramming a plurality of negative beliefs of the user through relaxation, breathing, recording and repeating of a plurality of de-programming and reprogramming statements, confirmed as accurate, by the digital framework through an analysis of the plurality of sensors data in combination with the underlying unconscious agendas of the user.

BRIEF DESCRIPTION OF DRAWINGS

Non-limiting and non-exhaustive examples are described with reference to the following figures.

DETAILED DESCRIPTION

Figure 1:
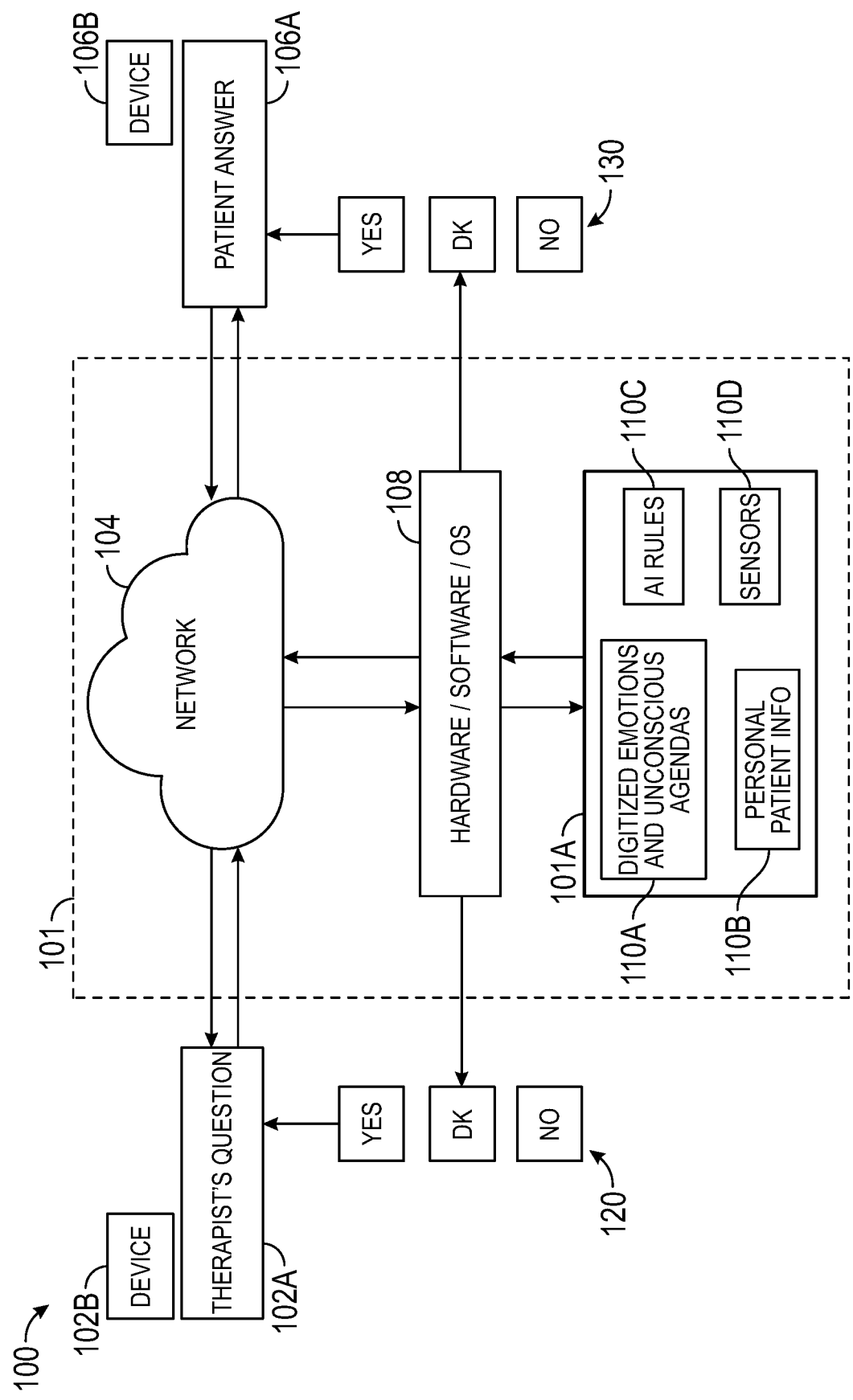
FIG. 1 illustrates a health status recording and reporting system including a digital framework that includes a pattern recognition module configured to record and report a health status of a user.

Various aspects of the disclosure are described more fully below with references to the accompanying drawings, which form a part hereof, and which show specific exemplary aspects. However, different aspects of the disclosure may be implemented in many different forms and should not be construed as limited to the aspects set forth herein; rather, these aspects are provided so that this disclosure will be thorough and complete and will fully convey the scope of the aspects to those skilled in the art. Aspects may be practiced as methods, systems, or devices. Accordingly, aspects may take the form of hardware implementations, an entirely software implementation or an implementation combining software and hardware aspects. In examples, a model may be a rule-based model, a machine-learning regressor, a machine learning classifier, a neural network, or any combination thereof. In addition, changes in biometric sensors could be combined with any configuration already stated. The following detailed description is not to be taken in a limiting sense. In addition, the truth-detection assistant can also evaluate biometric sensor data from non-verbal communication from a user "experiencing an emotion" while being connected to biometric sensors or other biological methods, with, in some embodiments, only the positive, yes response result being the data that is collected, stored and used in various implementations. In another aspect the negative or don't know answers may be stored and used for research in yet another implementation.

A "Gene expression measurement", as used in this disclosure, is usually achieved by quantifying levels of the gene product, which is often a protein. Two common techniques used for protein quantification include Western blotting and enzyme-linked immunosorbent assay or ELISA. Note, new methods of measuring proteins and other substances, cells, electrical impulse etc., are being discovered and so the discovery is not limited through previously, commonly-used methods.

A "health status recording and reporting system", as used in this disclosure, essentially relates to a personality to disease condition mapping system that includes a digital framework including a pattern recognition module configured to assess commonly experienced emotions and belief systems and diagnosed and/or reported disease conditions of a user;

A "method of recording and reporting a health status of a user", as used in this disclosure, essentially relates to creating a prediction of human disease conditions, personality risk factor, based upon "personality," by assessing the plurality of human emotions/unconscious agendas and predicting disease conditions based upon similar data across a population and verified through epigenetic comparison of the group, to identify similarities between diagnosis, commonly experienced emotions and belief systems of the group. The method is implemented using a digital framework that includes a pattern recognition module and epigenetics testing.

"Recording and reporting a health status of a user", as used in this disclosure, essentially relates to personality to disease condition mapping method, meaning emotional/belief system assessment and mapping to disease conditions of the user using a digital framework that includes a pattern recognition module configured to map emotions and belief systems to disease conditions;

A "health status", as used in this disclosure, includes both physiological health and mental health. An exemplary health status further means any commonly experienced emotions and belief systems and diagnosed and/or reported disease conditions of a user, the prediction of disease conditions, personality risk factor. Further, a "health status", as used in this disclosure includes epigenetic measurement across groups that present similarly, as mapped from disease conditions to emotions and belief systems. Currently, genome discovery knows that genes express when a disease condition exists (not all of course but many). What is different is, we relate emotions and belief systems to genes to predict disease conditions, before they occur. But to do the discovery work, and build the map, we must first verify that a person with a disease does exhibit, experience X emotions and X beliefs.

An "unconscious agenda", as used in this disclosure, means perceptions, beliefs, mindsets, of a control group of users selected from a population of users;

A "therapist", as used in this disclosure, means and includes human and digital therapist and/or chatbot, avatar, coach/friend, etc.;

A "computer", as used in this disclosure, means any machine, device, circuit, component, or module, or any system of machines, devices, circuits, components, modules, or the like, which are capable of manipulating data according to one or more instructions, such as, for example, without limitation, a computer processor, a microprocessor, a central processing unit, a general purpose computer, a super computer, a personal computer, a laptop computer, a palmtop computer, a notebook computer, a desktop computer, a workstation computer, a server, or the like, or an array of computer processors, microprocessors, central processing units, general purpose computers, super computers, personal computers, laptop computers, palmtop computers, notebook computers, desktop computers, workstation computers, servers, or the like.

A "server", as used in this disclosure, means any combination of software and/or hardware, including at least one application and/or at least one computer to perform services for connected clients as part of a client-server architecture. The at least one server application may include, but is not limited to, for example, an application program that can accept connections to service requests from clients by sending back responses to the clients. The server may be configured to run the at least one application, often under heavy workloads, unattended, for extended periods of time with minimal human direction. The server may include a plurality of computers configured, with the at least one application being divided among the computers depending upon the workload. For example, under light loading, the at least one application can run on a single computer. However, under heavy loading, multiple computers may be required to run the at least one application. The server, or any if its computers, may also be used as a workstation.

A "database", as used in this disclosure, means any combination of software and/or hardware, including at least one application and/or at least one computer. The database may include a structured collection of records or data organized according to a database model, such as, for example, but not limited to at least one of a relational model, a hierarchical model, a network model or the like. The database may include a database management system application (DBMS) as is known in the art. The at least one application may include, but is not limited to, for example, an application program that can accept connections to service requests from clients by sending back responses to the clients. The database may be configured to run the at least one application, often under heavy workloads, unattended, for extended periods of time with minimal human direction.

A "communication link", as used in this disclosure, means a wired and/or wireless medium that conveys data or information between at least two points. The wired or wireless medium may include, for example, a metallic conductor link, a radio frequency (RF) communication link, an Infrared (IR) communication link, an optical communication link, or the like, without limitation. The RF communication link may include, for example, WiFi, WiMAX, IEEE 802.11, DECT, 0G, 1G, 2G, 3G or 4G cellular standards, Bluetooth, and the like.

The terms "including", "include" and variations thereof, as used in this disclosure, mean "including, but not limited to", unless expressly specified otherwise.

The terms "a", "an", and "the", as used in this disclosure, means "one or more", unless expressly specified otherwise.

Devices that are in communication with each other need not be in continuous communication with each other, unless expressly specified otherwise. In addition, devices that are in communication with each other may communicate directly or indirectly through one or more intermediaries.

Although process steps, method steps, algorithms, or the like, may be described in a sequential order, such processes, methods and algorithms may be configured to work in alternate orders. In other words, any sequence or order of steps that may be described does not necessarily indicate a requirement that the steps be performed in that order. The steps of the processes, methods or algorithms described herein may be performed in any order practical. Further, some steps may be performed simultaneously.

When a single device or article is described herein, it will be readily apparent that more than one device or article may be used in place of a single device or article. Similarly, where more than one device or article is described herein, it will be readily apparent that a single device or article may be used in place of the more than one device or article. The functionality or the features of a device may be alternatively embodied by one or more other devices which are not explicitly described as having such functionality or features.

A "computer-readable medium", as used in this disclosure, means any medium that participates in providing data (for example, instructions) which may be read by a computer. Such a medium may take many forms, including non-volatile media and volatile media. Non-volatile media may include, for example, optical or magnetic disks and other persistent memory. Volatile media may include dynamic random access memory (DRAM). Transmission media may include coaxial cables, copper wire and fiber optics, including the wires that comprise a system bus coupled to the computer processor. Common forms of computer-readable medium include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other non-transitory medium from which a computer can read. A computer program product may be provided that stores software or computer readable program code on a computer-readable medium configured to, when read and executed by a computer processor, perform one or more steps of the processes described herein.

Various forms of computer readable media may be involved in carrying sequences of instructions to a computer. For example, sequences of instruction (i) may be delivered from a RAM to a computer processor, (ii) may be carried over a wireless transmission medium, and/or (iii) may be formatted according to numerous formats, standards or protocols, including, for example, WiFi, WiMAX, IEEE 802.11, DECT, 0G, 1G, 2G, 3G or 4G cellular standards, Bluetooth, or the like.

One or more parts of the above implementations may include software. Software is a general term whose meaning can range from part of the code and/or metadata of a single computer program to the entirety of multiple programs. A computer program (also referred to as a program) comprises code and optionally data. Code (sometimes referred to as computer program code or program code) comprises software instructions (also referred to as instructions). Instructions may be executed by hardware to perform operations. Executing software includes executing code, which includes executing instructions. The execution of a program to perform a task involves executing some or all of the instructions in that program.

An electronic device (also referred to as a device, computing device, computer, etc.) includes hardware and software. For example, an electronic device may include a set of one or more computer processors coupled to one or more machine-readable storage media (e.g., non-volatile memory such as magnetic disks, optical disks, read only memory (ROM), Flash memory, phase change memory, solid state drives (SSDs)) to store code and optionally data. For instance, an electronic device may include non-volatile memory (with slower read/write times) and volatile memory (e.g., dynamic random-access memory (DRAM), static random-access memory (SRAM)). Non-volatile memory persists code/data even when the electronic device is turned off or when power is otherwise removed, and the electronic device copies that part of the code that is to be executed by the set of computer processors of that electronic device from the non-volatile memory into the volatile memory of that electronic device during operation because volatile memory typically has faster read/write times. As another example, an electronic device may include a non-volatile memory (e.g., phase change memory) that persists code/data when the electronic device has power removed, and that has sufficiently fast read/write times such that, rather than copying the part of the code to be executed into volatile memory, the code/data may be provided directly to the set of computer processors (e.g., loaded into a cache of the set of computer processors). In other words, this non-volatile memory operates as both long term storage and main memory, and thus the electronic device may have no or only a small amount of volatile memory for main memory.

In addition to storing code and/or data on machine-readable storage media, typical electronic devices can transmit and/or receive code and/or data over one or more machine-readable transmission media (also called a carrier) (e.g., electrical, optical, radio, acoustical or other forms of propagated signals—such as carrier waves, and/or infrared signals). For instance, typical electronic devices also include a set of one or more physical network interface(s) to establish network connections (to transmit and/or receive code and/or data using propagated signals) with other electronic devices. Thus, an electronic device may store and transmit (internally and/or with other electronic devices over a network) code and/or data with one or more machine-readable media (also referred to as computer-readable media).

Software instructions (also referred to as instructions) are capable of causing (also referred to as operable to cause and configurable to cause) a set of computer processors to perform operations when the instructions are executed by the set of computer processors. The phrase "capable of causing" (and synonyms mentioned above) includes various scenarios (or combinations thereof), such as instructions that are always executed versus instructions that may be executed. For example, instructions may be executed: 1) only in certain situations when the larger program is executed (e.g., a condition is fulfilled in the larger program; an event occurs such as a software or hardware interrupt, user input (e.g., a keystroke, a mouse-click, a voice command); a message is published, etc.); or 2) when the instructions are called by another program or part thereof (whether or not executed in the same or a different process, thread, lightweight thread, etc.). These scenarios may or may not require that a larger program, of which the instructions are a part, be currently configured to use those instructions (e.g., may or may not require that a user enables a feature, the feature or instructions be unlocked or enabled, the larger program is configured using data and the program's inherent functionality, etc.). As shown by these exemplary scenarios, "capable of causing" (and synonyms mentioned above) does not require "causing" but the mere capability to cause. While the term "instructions" may be used to refer to the instructions that when executed cause the performance of the operations described herein, the term may or may not also refer to other instructions that a program may include. Thus, instructions, code, program, and software are capable of causing operations when executed, whether the operations are always performed or sometimes performed (e.g., in the scenarios described previously). The phrase "the instructions when executed" refers to at least the instructions that when executed cause the performance of the operations described herein but may or may not refer to the execution of the other instructions.

Electronic devices are designed for and/or used for a variety of purposes, and different terms may reflect those purposes (e.g., user devices, network devices). Some user devices are designed to mainly be operated as servers (sometimes referred to as server devices), while others are designed to mainly be operated as clients (sometimes referred to as client devices, client computing devices, client computers, or end user devices; examples of which include desktops, workstations, laptops, personal digital assistants, smartphones, wearables, augmented reality (AR) devices, virtual reality (VR) devices, mixed reality (MR) devices, etc.). The software executed to operate a user device (typically a server device) as a server may be referred to as server software or server code), while the software executed to operate a user device (typically a client device) as a client may be referred to as client software or client code. A server provides one or more services (also referred to as serves) to one or more clients.

The term "user" refers to an entity (e.g., an individual person) that uses an electronic device. Software and/or services may use credentials to distinguish different accounts associated with the same and/or different users. Users can have one or more roles, such as administrator, programmer/developer, and end user roles. As an administrator, a user typically uses electronic devices to administer them for other users, and thus an administrator often works directly and/or indirectly with server devices and client devices.

Proposed by this invention is a dramatic expansion of Health Psychology with focus on correlating specific emotions to specific disease conditions, and the unconscious agendas that underlie them plus the methods and systems to re-program unwanted or inhibiting beliefs by accessing the unconscious with AI/ML/Sensors where all the answers for a person live. Biometric sensors are being used today to measure the changes in the pupil, pupil dilation, to detect deception at a rate of 80-86% accuracy compared to a human attempting to do the same at only a 54% accuracy rate. We believe we are measuring the same element within the psyche that reacts with pupil changes whether it be the conscience or the unconscious. We believe it's both and hence this invention is to harness the power of truth-detection to benefit humankind. This invention will not limit biometric sensors to pupil dilation but will use one of more other sensors to reach a 99.99% efficacy rate. We also prefer to use the term: Truth Detection vs. Lie Detection.

This invention is expected to offer insights not available to either the therapist or the client/patient/person (at work, home or at play) and improve communication and unconscious information-sharing. Its purpose is to improve outcomes for those experiencing trauma, anxiety, depression or any diagnosed mental disease high levels of stress, inability to parent well, lead others, or remain consistent during sport and reduce risk and occurrence of disease conditions. The systems and methods disclosed herein can be used to analyze the relationship between unconscious agendas (what we believe) and disease conditions as it is theorized that each disease, whether physical or mental is the result of long-standing self-destructive beliefs that produce recurring negative emotions. An example would be migraines. In our research the underlying belief is, "I can't confront differences." So, when exposed to two opposite conditions, the body's chemistry/biology creates the migraine in an attempt to keep the victim from confronting differences because his/her "programming" says, "don't confront differences."

The key components included in the systems and methods are: 1) repositories of emotions, unconscious agendas (what we believe is true) which the system digitizes first for use with patients (users), 2) rule sets; education and training in regard to emotions, unconscious agendas, disease conditions, communication models for understanding, responses, a human-tempered response framework (conscience), and how to interpret questions, and answers, 3) personal information of the patient and/or person providing the answers to questions including a list of diagnosed disease conditions, personal stories, defined traumas, aspirations, preferences, his/her belief systems, session notes and/or observation(s) by others such as a report, 4) biometric sensors connected to the patient during questioning, and 5) machine learning technology that leverages all four components to differentiate between true, false or don't know answers made by patients, from questions posed by the therapist. Therapists and patients both have an interface and access to designated information as the use case defines.

To elaborate in this context, conscience is a human component of the mind that determines what is right or wrong. The human-tempered response framework is the software that includes the training of empathy, how to response to a human with questions to dig deeper. Pausing, or investigating further is what it means to temper a response "humanly" by a digital therapist, coach, chatbot, etc.

The systems and methods described here are not necessarily to build a lie detector. While it could be used for that purpose by changing the data sets and rules relevant to this use case, its purpose is to predict human disease conditions based upon unconscious agendas held by the patient and negative emotions experienced as a result by by-passing the conscious mind that is rarely "aware" of how it really feels and can only guess. The unconscious knows the exact feeling but needs easy access to find it, hence this invention.

The communication method between the therapist, patient and the AI machine engine can occur in any method from converting voice to text, for processing or by the AI machine engine learning conversational communication and may include using machine learned techniques and/or natural language processing techniques and may also include the use of latent semantic indexing, latent Dirichlet processing, word and/or sentence embedding models, collaborative filtering techniques, entity graphs, Jaccard similarity, cosine similarity and/or translation models.

In another embodiment, examples of the present disclosure describe systems and methods including software and/or hardware to create an improved virtual embodiment experience in the Metaverse, or other digital environments, and new systems and methods for communicating in real-time with one universal language across all populations, with attributes common to human or brain interaction, such as gestures, expressions, movements, emotions, beliefs, intent and intuition to create a life-like virtual agent including haptic effect to transmit emotions, intuition, and intent. This disclosure describes security features for protection, with features to create a mixed reality life form that feels feelings, intent and intuition. Sensors are utilized to measure brain waves to heighten awareness for threats identified and non-identified by analyzing the stress response system (SRS). The detection of brainwaves, brain or nervous system activity can be measured via several methods of quantum dots, digital footprint detection to predict an intent score, along with using biometric sensors to detect pure intent and bad-natured behavior. As intent is measured it will also alert/influence the decision making to act on the intent for further analysis. The Datastores of assets such as intent-word, word to color-matching, to convert words to colors, and colors to words using machine learning to manage context issues, are the foundation of a Universal language, an important component of this invention to communicate necessary messages. Other assets include photographs and videos of gestures, expressions, emotions, physiological responses and movements along with ethnicity, cultural, and gender photos and videos, all automatically converted into 3D wireframes for rendering graphical layers upon, in the Metaverse, or in other environments. The possible combinations of each of these assets allows for a unique embodiment, that is historically engraved in humanity. The virtual agent can change itself in persona, physical form, characteristic, cognitive profile and emotional state in the metaverse however, based upon selected option(s) including a choice to be one's real self, or change to an environment-appropriate agent, such as when under threat, or entering a work meeting, going to a party, or joining a group to blend in, etc. This alleviates the task to re-ornate oneself, being able to modify one's persona with thought on the fly or using programmable presets triggered automatically by environment change. This will further help humans orient and adapt to such technologies easier, by utilizing ML for their adaptation along with understanding of the possibilities of unlimited digital environments.

Implementing the scope and application of this disclosure into the Metaverse, or other environments, adds security to the agent by being able to validate or invalidate any question's answer, thus protecting against exploitation. While the exterior of the agent may change its visual form, the identity of the avatar itself (the owner) is fixed and known only to the owner unless the owner chooses to share it. Its unique properties allow persona to build trust, choose authentic friends, and have knowing through this security feature if someone is safe to trust and will alert for those that are not, by digitally measuring intent, allowing the avatar/person the free will to engage, or steer clear. While this disclosure is described as a feature for humans, it can also be immersed, merged into the Metaverse environment, and can be used between one virtual agent to another as well as human to virtual agent.

This morphing avatar affectively provides users with an automated fight or flight system which humans have and virtual agents currently, do not embody. Sensors worn by users in the real world or embedded in devices, either remote or virtual, respond to interpreted data from the Metaverse, emitted by others or situations having the methods and systems described in this disclosure to alert a person that a threat exists and in the present disclosure respond with an appropriate action. For example, if someone begins to stalk someone in the Metaverse the user being stalked could activate or automate a persona modification as well as receiving guidance on how they could react, predicting and suggesting behavioral response(s). A morphing virtual agent can also reflect someone else by sensing another's persona and commence mirroring upon mutual consent. Some of these morphings could also benefit helping another user adjust and feel comfortable, less stressed in a new environment. There are many useful reasons why someone would want to obscure, enhance or reflect personas. These are only a few.

Many only dream of a virtual agent that not only appears life-like using CGI, but also feels life-like. This disclosure describes how to solve for this by infusing intent, affect, feelings, intent, intuition, a universal language and corresponding movements into a morphing CGI avatar skin that can be modified on demand.

To be able to conceive and create the methods and systems for this life-like avatar requires a background in psychology, understanding what makes us human and a technologist to understand how to mirror that knowledge into code. This inventor brings both to the table and with an assist from a PhD colleague adds the scientific component to bring this avatar to life.

This disclosure offers the methods and systems to generate a 3D virtual agent that is capable of representing a real person, in the way they communicate and feel including machine learning methods to collect and fine-tune the relationship between oneself and its avatar so that the avatar is a full extension, capable of "being" that person in the Metaverse. In specific to virtual technology this is called an embodiment where the user feels as one with their avatar.

This concept has been proven by various research to have convinced the user of a mirror effect that makes them believe that the avatar is themselves.

Provided by this disclosure is a dramatic expansion of the avatar world and while conceptual, the systems and methods to bring it to life are not available in prior art and makes this invention novel. A life-like avatar is not only needed but desired by many.

Finally, the systems and methods to construct and deliver an expressive, experiential morphing avatar to life-like existence includes hardware, software, in the form of sensors (quantum dots or other brain wave, brain and/or nervous system sensors), physiological responses such as brainwaves and pupil reaction, micro expressions and such, datastores of assets, inputs and new models in machine learning, facial recognition, natural language processing and other computational processes. These will leverage existing best practices for language understanding and speech synthesis, semantics, color theory, 3D configuration, video transitions, biometric sensors, and digital asset management, configuration, and storage, among others.

This disclosure adds multiple human characteristics to avatars including a stress response system (SRS) by implementing the technology into the Metaverse. This SRS system also provides virtual intuitive cues to increase awareness. One language for all to easily communicate is another feature, and most importantly, the ability to safeguard one's identity with a façade in the form of a morphing avatar. And finally, intent (motive) and intuition are infused into the avatar, creating the ability for an avatar to become life-like.

Human intent drives emotions and behaviors and is what underlies all expression whether it be facial, body language or movement. It also is what makes us human. Goals and the desire to accomplish are informed by intent. Intent is digitized in this disclosure to add yet another human feature to the virtual agent. Notably, the measurement of intent is also used to determine threat (by measuring the intent of self or others using biometric sensors).

Experiences are elicited in the Metaverse and transmitted back to the user locally using biometric sensors, haptic effect tools and/or any other methods yet to be developed and readily available to implement a two-way experience between agent and user. Any specific reference in this disclosure does not limit its application in other formats, methods or systems, not yet contemplated or presented.

In another embodiment, examples of the present disclosure describe systems and methods including software and/or hardware to validate a reprogramming system with help of Epigenetic algorithm. Epigenetics is the study of gene expression. Epigenetics is a method to analyze changes in DNA expression to determine what emotions and behaviors are related to disease conditions and is a validation method chosen, among others.

To identify the negative emotion(s) often felt coming from an unconscious agenda is what therapists look for, beneath what is consciously known to a patient and the story they are telling, but instead seek to delve into the unconscious world of traumas, events, and a whole host of programming that directs the behavior of their patients, by asking questions and watching for reactions. The purpose of this invention is to bypass the conscious "knowing/verbal communication," and access the unconscious mind by analyzing answers to questions and looking for confirmation or not through AI/ML technology. This is the core goal of the systems and methods of this invention. Upon discovery, reprogramming of negative beliefs is accomplished through relaxation, breathing and repeating of de-programming and reprogramming statements, confirmed as correct, by AI/ML through the analysis of biometric sensor data in combination with personal information of the patient, repositories of emotions and unconscious agendas and AI rule sets. The therapist leads and the AI therapy assistant supports the therapist to "get to point" faster and more precisely than possible through a therapeutic conversation.

The benefit of validating the patient's answers as true or false cuts through extensive talking, often about the problem, and not as much about the solution. In this invention, assistance is provided to the therapist to quickly identify underlying unconscious agendas (core beliefs) that generate behavior and associated negative emotions by validating or invalidating the line of questioning from the therapist with the patient.

The rules portion of this invention trains the AI/ML how to ask questions, what list of emotions and unconscious agendas are and how to translate them, and biometric sensor results interpretation training. There is also a library of physical and mental disease conditions to correlate emotions and beliefs systems with. In addition, patient personal information is collected to personalize each QA session, including his/her life stories, personality traits and preferences, traumas throughout life, aspirations, record of discovered unconscious agendas, reported diagnosed disease conditions and therapy session notes, if any.

Finally, there is biometric sensor data from one or more inputs. The AI/ML engine receives an answer to a question posed by a questioner/along with a request for a response, either automated, queued and/or saved. The AI/ML engine uses its rule sets to compare the patient's answer to the digitized emotions, unconscious agendas, with personal data and the biometric sensor(s) to determine if the response is true, signaling its response as a yes, no or don't know through LED signaling or other methods common to signaling. Multiple systems and methods can be used for this communication. Biometric sensor(s) data includes detection of eye and/or facial movements, pulse, respiration, blood pressure changes, brain waves and/or DNA expression changes, or any other method to sense the truth or untruth of patient answers to questions posed by the therapist.

The methods and systems for assisting a therapist when conducting a therapy session with a user is foremost in the description herein, however, there is a wide range of use cases possible, including as a lie detector, a system and method for determining the emotions experienced by humans and to measure the probability of users being a good fit as an employee, a borrower, a candidate for parole, and/or the mental success factors, or the failure points, of an athlete.

The methods and systems can also be used to detect the truthfulness of non-verbal input such as feeling a feeling, or stating a belief system, using the same methodology.

The use of the term "therapist" does not limit its user base. For the purpose of this document and for the best understanding of this disclosure this term has been chosen, but the user conducting the questioning could be anyone from a coach to a parole officer, or anyone in between and the "user" can be any user type being questioned.

A therapist typically discusses emotional and/or behavioral issues that a user is experiencing to assist in the discovery of a cause and to provide guidance on possible solutions. A therapist is handicapped by the simple fact that users don't have access to what they "really feel or what they really believe," held deep in the unconscious and most often not available to consciousness, yet feelings and behavior occur as a result of this unconscious material. As complex human beings and to operate efficiently, we people are consciously tasked with only two or three thoughts at once such as driving, the wind blowing in your hair from an open window and the fragrance of spring flowers, and maybe also a song playing in the background. Even when driving we people are often on auto-pilot so we they can think about other things. What this means is our one's rich internal, unconscious life is operating below one's our consciousness including the autonomic system to provide thought-free heart beats, processing of inhaled oxygen and the digestion of food along with a high level of awareness to respond to anything. So, similar to an unawareness of how our one's body functions, out one's thoughts, feelings, memories are also out of our one's awareness unless we one consciously chooses to bring one or more up. And yet, even people wanting to bring up old memories to try to solve a behavioral problem or get released from negative emotions that control them, this is almost impossible because of the natural resistance (denial) their consciousness perpetuates to maintain the façade we they have built throughout their lives as an adaptive measure to be able to work, get along, perform, or raise a family. As a result of pushing down negative thoughts that may bubble up, humans have lost touch with their unconscious mind. It's not to say we people ever had full access, but access has been diminished by the ever-changing society around us. This explains why people who meditate have more access to their inner self, and benefit from it as proven by evidence-based research.

As a result, a therapist and his/her users can augment a therapy session with an AI Therapy Assistant that identifies the exact feeling being felt by the user and the unconscious agenda that causes it by directing a line of questioning. Each question asked by the therapist of the user is evaluated through biosensors and application of AI, repositories of information, rule sets and the personal information of a user, to determine what is true and what is false.

As our world changes it is easy to see how people are the product of their upbringing, the worldview that has been shaped by their experience, and the influences of politics, religion, and even fringe groups that can overtake the rationale of humans. If people can change toward the negative, then certainly, they can change for the positive, and this disclosure is for those who want to live better, healthier lives. No longer does anyone need to get stuck or be cursed by an abusive parental upbringing, spouse or child just because it's their experience. Now, each horrendous belief/unconscious agenda can be identified and changed for a different outcome, a healthy one.

The work underpinning this invention has been antidotally proven with thousands of users over the last 40 years and its time has come to build the technical components that embody the methodology to scale help to millions and to predict disease conditions based upon personality, a collection of emotions and belief systems. Therapy sessions, sessions to help improve performance at home, at work or at play, one-on-one with a person is not scalable and limited to those with resources. To level the playing field and offer a superior process, this invention is being built a deployed for unlimited access. The replacement of a human therapist is also beneficial from the standpoint of a digital therapist being unbiased, having none personal life experience that can influence engagement between the therapist and the patient.

While specific problems may be discussed, it should be understood that the examples should not be limited to solving only specific problems identified in the background or elsewhere in this disclosure.

The AI Therapy Assistant is built to perform a number of tasks that include digitizing emotions and belief systems for use when assisting a therapist. The system is also used to match reported diagnosed diseases by a user and the emotions and belief systems commonly experienced by each user and compare them across a broad population with the same exact characteristics, to map specific disease conditions to specific emotions and belief systems. And thirdly, the disclosure includes the validation of the mapped emotions and belief systems with a disease condition to changes in DNA expression, measuring both before re-programming an unconscious agenda for a baseline and after the re-programming is complete, to compare them.

To date, failure to digitize emotions has been the result of using facial expression, context, and a number of other biometric measurements. However, the missing link is the ability to validate what someone is feeling across populations, cultures, gender, etc. This disclosure is built to do just that. If a person says, "I feel love," and it is measured by the AI process laid out in this disclosure, the answer will be validated or not by how true the statement is by accessing the unconscious for its truthfulness. Regardless of culture, gender, etc. each person has an unbiased unconscious and when asked if a statement made consciously is true, the unconscious can deliver an answer, in this disclosure. If a person does not feel loved, then the answer will be "no." The ability to "get around" the conscious mind is the only way to get a human to really tell the truth.

Most people lie every day. Most people lie in everyday conversation when they are trying to appear likable and competent, according to a study conducted by University of Massachusetts psychologist Robert S. Feldman. Also, an experiment to measure accuracy of conscious determination of truth-telling revealed that only 54% of the time could a human differentiate between truth or untruth. When measuring the same group with assigning a word to a person such as honest or dishonest, the level of accuracy was much higher, meaning that unconscious measures are better at detecting when someone is telling the truth versus lying. We pose that the detection is also applicable to self since the unconscious is responsible for preserving or improving life for its host. Have you ever felt yourself shift to the "zone" when life is threatened? It's your unconscious mind taking over to save you life, but just for a moment. Hence the birth of truth detection in therapy which is both a new system, method, and a non-obvious disclosure.

As an example of a processing device operating environment, refer to the exemplary operating environments. In other instances, the components of systems disclosed herein may be distributed across and executable by multiple devices. For example, input may be entered on a client device(s) and information may be processed or accessed from other devices in a network (e.g., server devices, network appliances, biometric sensors or other client devices, etc.).

FIG. 1 illustrates a health status recording and reporting system 100 that includes a digital framework 101 that includes a pattern recognition module 101A configured to record and report a health status of a user. The digital 101 framework includes (1) a digitally recorded library 110A of human emotions and unconscious agendas of a control group of users selected from a population of users; (2) a digitally recorded set of rules 110C related to at least one of: (i) education and training in regard to emotions, unconscious agendas, disease conditions of the control group of users, (ii) communication models for understanding, responses of the control group of users, (iii) a human-tempered response framework, (iv) interpretation of questions posed to the control group of users, and (v) interpretation of answers of the control group of users; and (3) a digitally recorded user profile 110B of the user, the user profile includes personal information of the user, personal information includes a list of diagnosed disease conditions, personal life stories, defined traumas throughout life, aspirations, personality traits and preferences, the user's belief systems, record of discovered unconscious agendas, reported diagnosed disease conditions session notes, and/or observation by other humans expressed in reports.

The health status recording and reporting system 100 also includes a plurality of sensors 110D communicably connected to the digital framework 101 and to the user during a question-answer session with a therapist (and/or chatbot, avatar, coach/friend, etc.), each of the plurality of sensors configured to communicate, record and report at least one of: a physiological state or an emotional state of the user while responding to a plurality of questions posed by the therapist during the question-answer session.

The digital framework 101 is configured to (i) integrate a first input from the digitally recorded library 110A of human emotions and unconscious agendas, a second input from the digitally recorded set of rules 110C, and a third input from the digitally recorded user profile 110B of the user, a fourth input from the plurality of sensors 110D, and a fifth input about a physical or a mental disease condition, (ii) validate an accuracy of the user's response to the plurality of questions posed by the therapist, based on the first input, the second input, the third input, the fourth input and the fifth input, wherein the accuracy of the user's response to the plurality of questions posed by the therapist includes a statistical level of confidence score calculated based on data collected from the control group of users or the population of users, (iii) map and predict a disease condition of the user based on the first input, the second input, the third input, the fourth input and the fifth input, wherein the disease condition includes a medically diagnosed disease condition, and (iv) display and report the predicted disease condition of the user on a visible report or a printable report.

The set of rules is used by the therapist to train the digital framework to ask questions based on a list of emotions and unconscious agendas. The digital framework also includes a second digitally recorded library of physical and mental disease conditions (described in more details, in relation to the description of FIG. 7, specifically, in relation to element 750) that can be correlated with emotions and beliefs systems of the user. This correlation can occur as a result of AI/ML learning that when X people report a diagnosed disease and report frequently experienced specific emotions and beliefs. Further, there is no "database" of commonly felt emotions and unconscious agendas; they get derived from this disclosure as it is collected from users reporting what their experience is. In the future, the information of how a person feels and what they believe can come from within the process alleviating the "reporting" by the user of their personal feelings or beliefs so we should address both manners of data collection for a person's commonly felt emotions and beliefs held.

The plurality of sensors comprise biometric sensors configured to perform at least one of: detection of eye and/or facial movements, monitoring of pulse, respiration, blood pressure changes, brain waves and/or changes in gene expression of the user.

In one aspect, the pattern recognition module 101A uses statistics-based pattern recognition, such as using stochastic modeling techniques and includes an artificial intelligence (AI) architecture configured to predict the disease condition based on a similarity score or metric that represents the estimated similarity between the control group of users and their reported disease conditions with commonly felt emotions and unconscious agendas.

In one aspect, the pattern recognition module 101A includes a machine learning (ML) module configured to train the digital framework based on the set of rules to translate the user's response from a plurality of digitally recorded questions, and to interpret a plurality of outputs from the sensors.

In this disclosure, an artificial intelligence based (AI) architecture is used to create a data model based on relationships between variables, the strength of relationships, and interactions between variables. Bayesian Optimization is an optimization algorithm. Multi-objective means an optimization case/situation where more than one interrelated objective functions need to be optimized. Bayesian optimization used for multi-objective situation is referred to as multi-objective Bayesian optimization. Machine learning means a statistical algorithm that can train data to create a learned data model based on historical variables, and the training thereof, and modify and update the data model based on newly obtained single or multiple observations. Data model means a set of variables selected from a data source based on predictor variables, outcome variables, and relationship, i.e. strength of relationship between variables. Strength of relationship can be between predictor variables and outcome variables. Predictor variables are variables used to predict an outcome. Outcome variables are variables in which their value is dependent on a predictor variable or predictor variables. Feature selection means an algorithm that can identify and select variables within a data source that contribute to the predictor variables and outcome variables. Variable interaction means that the contribution of one predictor variable is modified by one or many other predictor variables, so that the combined contribution of all variables involved in the interaction is greater than the simple sum over the individual contributions attributable to each variable.

The digitally recorded library 110A of human emotions and unconscious agendas, the digitally recorded set of rules 110C, the digitally recorded user profile 110B of the user, the visible report, and the printable report are stored in a secure, distributed storage network 104 that includes at least one of: a Blockchain application and a distributed database application. Blockchain is a promising technology that can be used to manage data using a distributed, secure network architecture. Data stored in a blockchain cannot be easily compromised. Therefore, data that is considered sensitive can be securely stored in a blockchain which can prevent the corruption and unauthorized access thereto.

The distributed storage network (or platform) 104 can be, for example, a blockchain application used to process and store data securely within a distributed storage environment using a peer-to-peer network and Public Key Infrastructure (PKI) cryptography. The distributed storage platform can also be a distributed database application, e.g. common applications used in big data platforms and cloud computing platforms, used to process and store data securely within a distributed storage environment. The distributed storage platform can be a combination of a block chain application and a distributed database application. The data stored in the distributed storage environment can include, and without limitation, optimization variables, data models, and sensor and control variables. In one aspect, data provenance and data security are preserved by the use of blockchain so that data integrity is preserved. A digital twin or a subset of the data can be stored in the cloud so that AI/ML algorithms can be executed more efficiently.

The digital framework 101 is (i) installed on at least one of: a mobile telephone, a personal digital assistant, a computer and a distributed network system, (ii) accessed from the at least one of: the mobile telephone, the personal digital assistant, the computer and the distributed network system, and (iii) operationalized from the at least one of: the mobile telephone, the personal digital assistant, the computer and the distributed network system.

FIG. 1 further illustrates an overview of an example health status recording and reporting system 100 for creating a truth-telling assistant to a therapist as described herein. Example health status recording and reporting system 100 may be a combination of interdependent components that interact to form an integrated whole for assisting therapy. In aspects, health status recording and reporting system 100 may include hardware components (e.g., used to execute/run an operating system (OS)), and/or software components (e.g., applications, application programming interfaces (API's), modules, virtual machines, runtime libraries, etc.) running on hardware 108. As an example, therapist 102B and user devices 106B may provide access to user data of great variety including separate user interfaces with different data available including a Questioner version and an Answering version. Such data may be locally stored on hardware and include question, answer, and response information 120 and 130, with disclosure of the answer 120 to the therapist only, or both. For instance, therapist 102B or client devices 106B may directly access or query the AI response from an answer or receive it automatically. There may also be restrictions to data that is only for the therapist's eyes only. Various configurations can support various use cases and data access will vary between both, as applicable.

As presented, health status recording and reporting system 100 includes a therapist and/or therapist devices 102A-B, distributed network 104, distributed user device(s) 106A-B and a distributed server environment comprising one or more servers, such as server devices 110A-D One of skill in the art will appreciate that the scale of systems such as system 100 may vary and may include additional or fewer components than those described in FIG. 1. In some aspects, interfacing between components of the system 100 may occur remotely, for example, where components of system 100 may be distributed across one or more devices of a distributed network.

In some aspects, the AI therapy assistant may express in signals, lights, text, alerts, voice, sensory or any other form of communicative method.

Additionally, user devices 106B may provide access to user data of great variety. Such data may be locally stored on user device(s) 106B, or on one or more of server devices 110A-D. When a therapist is asking questions of the user, the AI Therapy Assistant is learning and providing direction by signaling true or false to answers provided by the user from questions posed by the therapist, among other examples.

Figure 2:
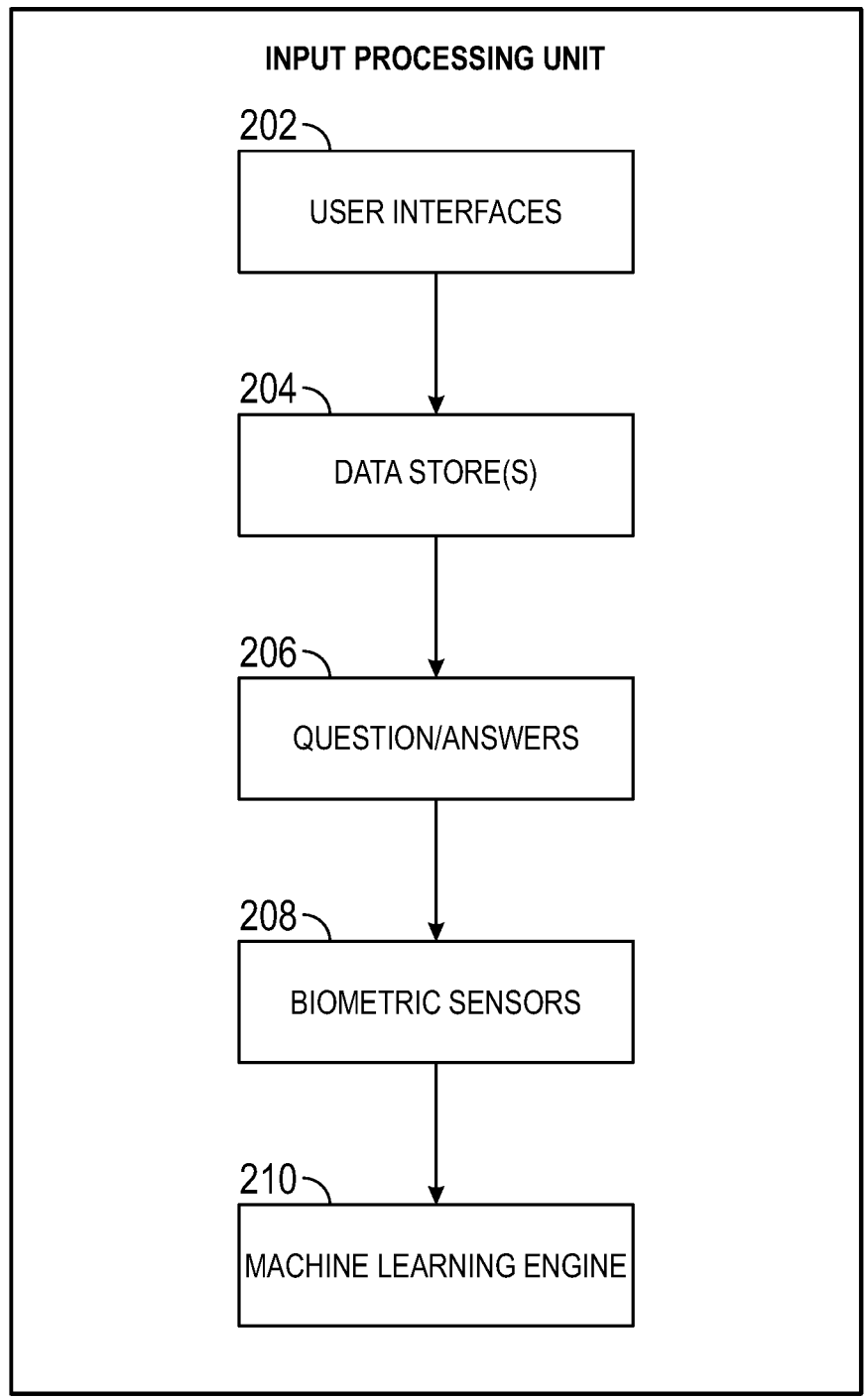
FIG. 2 illustrates an example of inputs for the machine learning engine to process for a network of an exemplary system for assisting a therapist with truth-detection capability.

FIG. 2 illustrates an overview of an exemplary input processing unit 200 for creating an AI Therapy Assistant, as described herein. The implementation is a combination of input process-components accessible by the therapist and/or client devices 202. In response to receiving the request, index engine 210 may access the knowledge base and the personal information of the user collected by interface 202 and/or stored by data store(s) 204. Index engine 210 may search for and collect questions, and/or answers identified in the request.

In at least one example, the analysis may include comparing one or more characteristics (e.g., traits, attributes, events, etc.) of a or the specific unconscious agenda or emotion in the knowledge base that includes sensor signals and related responses. Such characteristics may include demographic data (e.g., age, gender, location, time period of lifetime, etc.), behavioral data (e.g., access emotions, unconscious agendas, events, traumas as well as questioning techniques, etc.), stylistic content of data (e.g., style, diction, tone, voice, intent, sentence/dialogue length and complexity, etc.), psychographic data (e.g., opinions, values, attitudes, tempered responses, etc.), and the like. In such an example, at least a subset of the characteristics may be provided to a scoring or comparison algorithm/model for evaluation. The scoring or comparison algorithm/model may generate and/or assign scores or labels to the evaluated characteristics. The scoring or comparison algorithm/model may use the generated scores/labels to determine a similarity score or metric questions, answers, responses. The similarity score/metric may represent the estimated similarity between a specific questions/answers or responses. In aspects, the processed customized data may be used to create, organize, populate or update the machine learning engine for the specific question/answer/response to a disease condition.

Machine learning engine 210 may be further configured to access one or more data sources and/or APIs. In aspects, Machine learning engine 210 may have access to one or more data sources comprising logic for composing one or more questions directed to solicit information from a user. Information obtained as a result of posing the one or more questions to users or the specific therapist may be provided and processed accordingly.

The machine learning model may apply decision logic to determine a hierarchal data traversal process for collecting and analyzing therapist question, user reply data. In such aspects, questions/answers 206 may associate one or more established rule sets (or models) and facilitate the deployment and/or implementation of an AI Therapy Assistant and rule set (or model) to one or more computing devices, services or user accounts.

In another embodiment, FIG. 2 illustrates an overview of an exemplary input processing unit 200 for creating a morphing avatar, as described herein. The morphing avatar creation techniques implemented by input processing unit 200 may include the techniques and input described in FIG. 1. In alternative examples, a single system (comprising one or more components such as computer processor and/or memory) may perform the methods and processes described in systems 100 and 200, respectively.

With respect to FIG. 2, input processing unit 200 may include user interface 202, data store(s) 204, index generation engine 206, and biometric sensors 208. Interface 202 may be configured to receive, store and provide access to content, such as human characteristics, morphing avatar components for one or more avatars or agents. In aspects, interface 202 may access various data sources comprising human characteristics relating to one or more avatars or agents. Such data sources may include photos and videos renderings of multiple different combinations of genders and races, behavioral data and biometric sensor 208 interactions. The collected data may be stored by a data store accessible to interface 202, such as data stores 204. Data store(s) 204 may be configured to store and/or organize data according to various criteria. For instance, data store(s) 204 may store photos and videos, human characteristic data, colors, colors matched to words, meanings of words, and or emotions or intent.

Index engine 206 may be configured to create a personalized index generation engine. In aspects, index engine 206 may receive a request to generate a persona index. The request may be associated with one or more specific combination avatar or agents in regard to gender and race. In examples, a request may be transmitted to index engine 206 via interface 202 or received directly via an interface component accessible by a client or client device. In response to receiving the request, index engine 206 may access biometric sensor data 208 collected by interface 202 and/or stored by data store(s) 204. Index generation engine 206 may search for and collect data associated with the one or more specific persona or agents identified in the request. The morphing aspects associated with the one or more specific persona or agents ("personalized data") may be combined with a persona index (or a generic persona index) and processed to facilitate the creation of a personalized persona index (e.g., a persona index corresponding to the personalized data for the specific avatar/entity). In some aspects, processing the personalized data may include identifying and categorizing biometric data 208.

Processing the personalized data may further include determining and categorizing conversation data associated with persona/agents identified in the request. In examples, determining similarities between a specific avatar/entity and another avatar/entity (e.g., the "other person") in the Metaverse may include using machine learned techniques, natural language processing techniques and/or sentiment analysis to analyze and compare the morphing aspects of the other person. Such an analysis/comparison may include the use of latent semantic indexing, latent Dirichlet processing, word and/or sentence embedding models, collaborative filtering techniques, entity graphs, Jaccard similarity, cosine similarity and/or translation models such as color coding and decoding and proposed in this disclosure. Such an analysis/comparison may further include the use of validation indicators. In at least one example, the analysis may include comparing one or more characteristics such as stylistic data (e.g., style, diction, tone, voice, intent, sentence/dialogue length and complexity, etc.) or color and shape assignments to emotions, intent, words or the meaning of words, or gestures, movements, and facial expression, and the like.

In such an example, at least a subset of the characteristics may be provided to a scoring or comparison algorithm/model for evaluation. The scoring or comparison algorithm/model may generate and/or assign scores or labels to the evaluated characteristics. The scoring or comparison algorithm/model may use the generated scores/labels to determine a similarity score or metric for any form of avatar/entity. The similarity score/metric may represent the estimated similarity between a specific avatar/entity and the other person/entity. In aspects, the processed personalized data may be used to create, organize, populate or update a personalized persona index for the avatar/agent identified in the request.

Index engine 206 may be further configured to access one or more conversational data sources and/or APIs. In aspects, index engine 206 may have access to one or more data sources comprising remote or Metaverse data. The emote or Metaverse data may be used to supplement the data in a persona index. The color-coded and color de-coded data may include morphing aspects and human characteristics collected/derived from a plurality of users and relating to one or more personas/agents, events, time periods, and/or conversational scenarios. This conversational data may include conversational algorithms/models for processing with the biometric sensors 208 and the morphing aspects of the avatar/agent, included in conversational data. In examples, the conversational data may be collected from the Metaverse, and stored in, for example, a Metaverse chat index. The Metaverse chat index may include Metaverse users' perceptions, opinions and knowledge, their intention, emotions, thoughts, feelings, etc. regarding the actions, communications and/or events relating to one or more specific avatars/agents, a period of time, or one or more events.

For example, Metaverse engagement is two-way with users interacting and learning from each other and coupled with machine learning advance future communications especially when enhanced by biometric sensors 208 collecting and exchanging information between two users, each with an interface 202, connected to the index generation engine 206 and receiving analyzed and converted data and language from biometric sensors 208.

Alternately, the engagement is one-way whereby only one user interface 202 is immersed in the Metaverse, signals, analysis, and conversion of language is received by one user. The one user can still hear the words, meaning of words and convert them into color and decode upon receipt, hence being able to hear any language not understood, and have it understood upon conversion/translation from color to words and meaning of words, in real-time.

The index generation engine 206 may be configured to generate an avatar or agents or LU model. In aspects, input processing unit 200 may cause avatar or agents engine 206 to generate one or more avatar or agents (or instances thereof). Input processing unit 200 may then cause or facilitate the application of data from a persona index to the one or more generated avatars or agents. In examples, applying personalized data to an avatar or agents may generate a personalized avatar or agents configured to interact conversationally in the persona of a specific avatar/entity. In the instance that a user has created more than one avatar, the algorithm will identify these two avatars as one virtual agent in order to not disturb the model 208 when comparing/finding similarities between avatars. Applying personalized data to an avatar or agents may also cause a voice font, or a 3D model of an avatar/entity to be applied to the avatar or agents. Avatar or agent's engine 206 may be further configured to establish a set of interaction rules for an avatar or agents such as with emotion, facial expression, intent, movement and or any other expression of thought or feeling. In aspects, the set of interaction rules may provide for determining when (and in what order) to utilize the data and various data sources available to index generation engine 206. As an example, avatar or agents engine 206 may establish a rule set dictating that, in response to receiving dialogue input, a specific avatar or agents may attempt to provide a response using data from the following data sets (in order): 1) morphing aspects from a specific person/entity, 2) morphing aspects from users similar to the specific person/entity, 3) morphing aspects from a global user base (such as the internet at large) that may or may not be similar to the specific person/entity, and 4) generic, catch all phrases/questions that are not specific to the specific person/entity. As another example, in response to receiving dialogue input, avatar or agent's engine 206 may provide the received dialogue input to a machine learning model for processing dialogue including color encoding and decoding. The machine learning model may then apply decision logic to determine a hierarchal data traversal process for collecting reply to data. In such aspects, avatar or agent's engine 206 may associate one or more established rule sets (or models) with a corresponding personalized avatar or agents according to preferences to avatar display including race and gender and facilitate the deployment and/or implementation of the avatar or agents and rule set (or model) to one or more computing device, services or user accounts.

Figure 3:
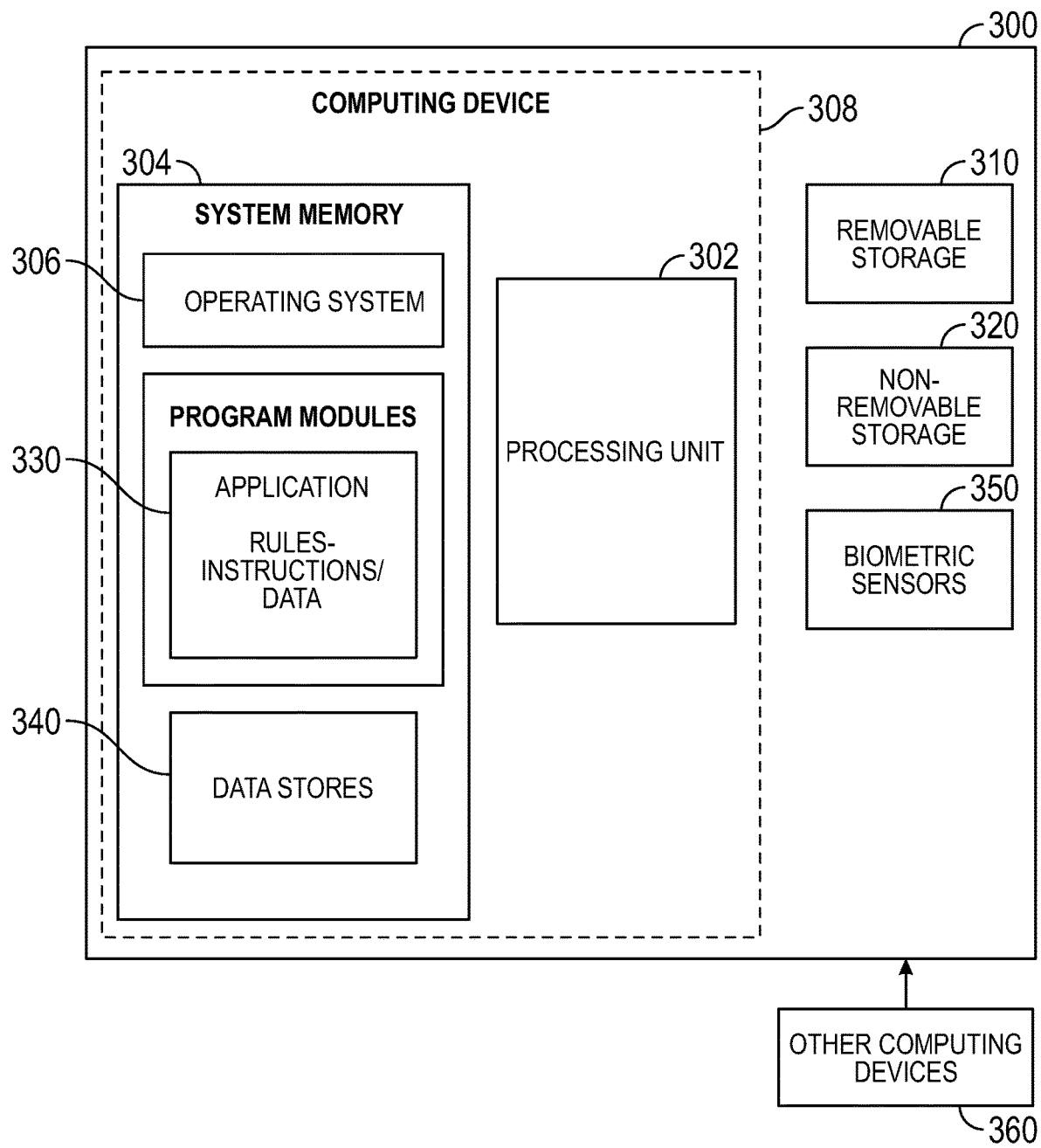
FIG. 3 is a block diagram illustrating example physical components of a computing device with which aspects of the disclosure may be practiced.

FIG. 3 is a block diagram illustrating physical components (e.g., hardware) of a computing device 300 with which aspects of the disclosure may be practiced. Example method 300 begins at operation 302 where a request associated with a specific person or entity is received. In aspects, a computing device, such as input processing unit 200, may receive a request to generate, train or modify a chat bot or LU model. FIG. 3 by a removable storage device 310 and a non-removable storage device 320. The computing device components described below may be suitable for the computing devices described above, including the client computing devices 102A-B and the server computing devices 106A-B. In a basic configuration, the computing device 300 may include at least one processing unit 302 and a system memory 304. Depending on the configuration and type of computing device, the system memory 304 may include, but is not limited to, volatile storage (e.g., random access memory), non-volatile storage (e.g., read-only memory), flash memory, or any combination of such memories. The system memory 304 may include an operating system 306 and one or more program modules 330 suitable for running software application 330, such as one or more components supported by the systems described herein. As an example, system memory 304 may store personal data (e.g., user personal data, trauma details, preferences, aspirations, user profile information, reported disease diagnosis, and behavioral data, etc.), instructions for creating an AI Therapy Assistant. The operating system 306, for example, may be suitable for controlling the operation of the computing device 308. Furthermore, embodiments of the disclosure may be practiced in conjunction with various libraries, other operating systems, or any other application program and is not limited to any particular application or system. This basic configuration is illustrated in FIG. 3 by those components within a dashed line 308. The computing device 300 may have additional features or functionality. For example, the computing device 300 may also include additional data storage devices 310 320 (removable and/or non-removable) such as, for example, magnetic disks, optical disks, or tape. Such additional storage is illustrated in FIG. 3 by a removable storage device 310 and a non-removable storage device 320.

As stated above, a number of program modules and data files may be stored in the system memory 304. While executing on the processing unit 302, the program modules 330 may perform processes including, but not limited to, the aspects, as described herein. Other program modules that may be used in accordance with aspects of the present disclosure may include electronic mail and contacts applications, word processing applications, spreadsheet applications, database applications, slide presentation applications, drawing or computer-aided application programs, etc. Furthermore, embodiments of the disclosure may be practiced in an electrical circuit comprising discrete electronic elements, packaged or integrated electronic chips containing logic gates, a circuit utilizing a microprocessor, or on a single chip containing electronic elements or micro processors. For example, embodiments of the disclosure may be practiced via a system-on-a-chip (SOC) where each or many of the components illustrated in FIG. 3 may be integrated onto a single integrated circuit. Such an SOC device may include one or more processing units, graphics units, communications units, system virtualization units and various application functionality all of which are integrated (or "burned") onto the chip substrate as a single integrated circuit. When operating via an SOC, the functionality, described herein, with respect to the capability of client to switch protocols may be operated via application-specific logic integrated with other components of the computing device 300 on the single integrated circuit (chip). Embodiments of the disclosure may also be practiced using other technologies capable of performing logical operations such as, for example, AND, OR, and NOT, including but not limited to mechanical, optical, fluidic, and quantum technologies. In addition, embodiments of the disclosure may be practiced within a general-purpose computer or in any other circuits or systems.

The computing device 300 may also have one or more input device(s) such as a keyboard, a mouse, a pen, a sound or voice input device, a touch or swipe input device, etc. The other computing device(s) 360 such as a display, speakers, a printer, LED lights and/or a signaling device, etc. may also be included. The aforementioned devices are examples and others may be used. The computing device 300 may include one or more communication connections allowing communications with other computing devices 360. Examples of suitable communication connections 330 include, but are not limited to, radio frequency (RF) transmitter, receiver, and/or transceiver circuitry; universal serial bus (USB) firewire, HDMI, UHD, parallel, and/or serial ports. The term computer readable media as used herein may include computer storage media. Computer storage media may include volatile and nonvolatile, removable and non-removable media implemented in any method or technology for storage of information, such as computer readable instructions, data structures, or program modules. The system memory 304, the removable storage device 310, and the non-removable storage device 320 are all computer storage media examples (e.g., memory storage). Computer storage media may include RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other article of manufacture which can be used to store information, and which can be accessed by the computing device 360. Any such computer storage media may be part of the graphical user interface (GUI), a visual indicator, LED, (e.g., a light emitting diode), and/or an audio transducer (e.g., a speaker). In some aspects, the mobile computing device incorporates a vibration transducer for providing the user with tactile feedback. In yet another aspect, the mobile computing device incorporates input and/or output ports, such as an audio input (e.g., a microphone jack), an audio output (e.g., a headphone jack), and a video output (e.g., a HDMI port) for sending signals to or receiving signals from an external device.

Figure 4:
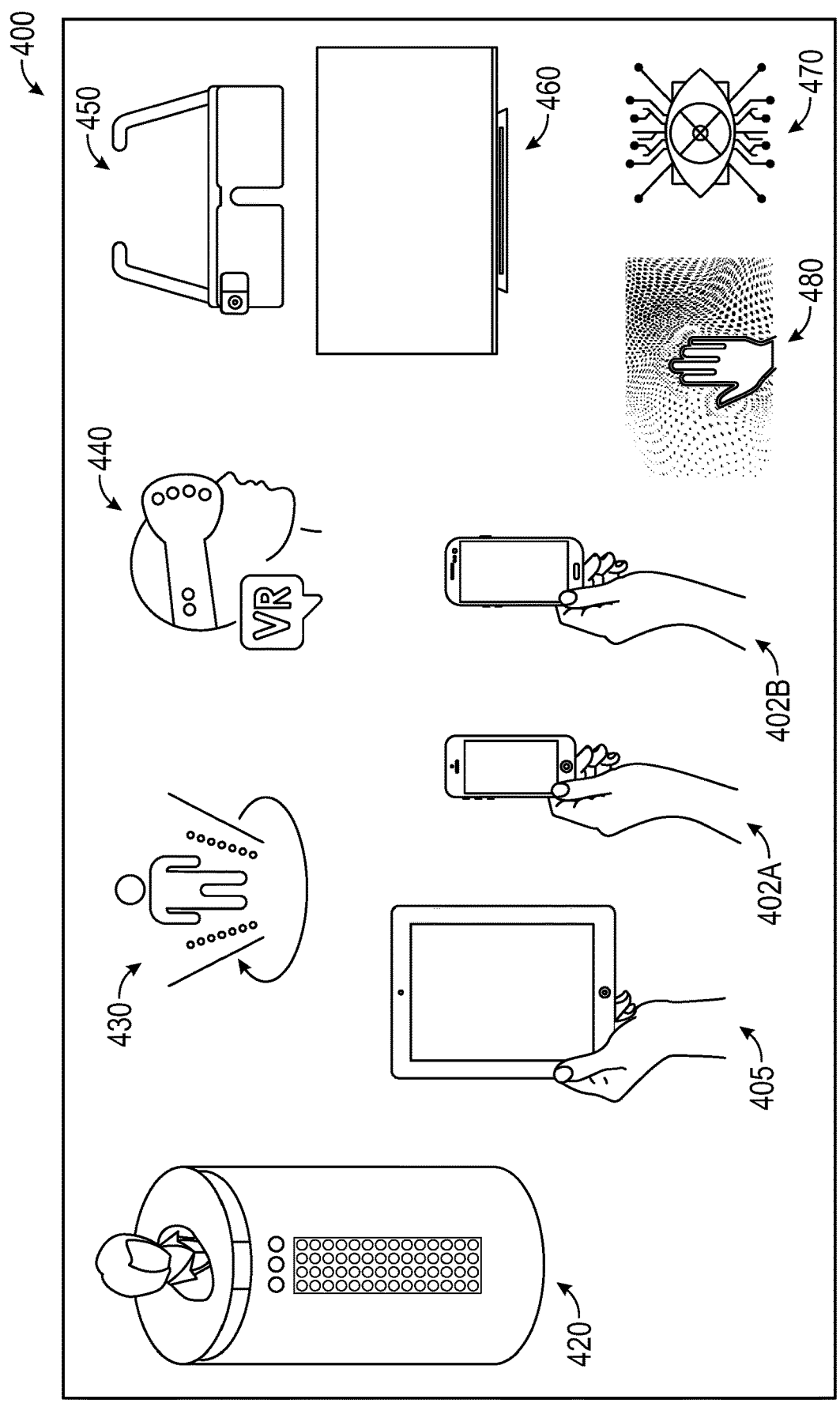
FIG. 4 are examples of computing devices with which aspects of the present disclosure may be practiced.

FIG. 4 is a diagram illustrating the architecture of various aspects of a computing device. That is, the computing devices 400 can incorporate a system (e.g., an architecture) to implement some aspects. In one embodiment, the system 402A is implemented as a "smart phone" capable of running one or more applications (e.g., browser, e-mail, calendaring, contact managers, messaging clients, games, and media clients/players). In some aspects, the system 402B is integrated as a computing device, such as an integrated personal digital assistant (PDA) and wireless phone. One or more application programs may be loaded into the memory and run on or in association with the operating system. Communication media may be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media.

FIG. 4 illustrates a computing device 400, for example, a mobile telephone, a smart phone, wearable computer (such as a smart watch), a tablet computer, a laptop computer, VR, 3D virtual experience, a personal assistant with hologram 430, smart glass 450, television screen 460, eye scanning device 470, sensory technologies 480 and the like, with which embodiments of the disclosure may be practiced. In some aspects, the client may be a mobile computing device. With reference to FIG. 4, one aspect of a mobile computing device 400 for implementing the aspects is illustrated. In a basic configuration, the mobile computing device 400 is a handheld computer having both input elements and output elements. The mobile computing device 400 typically includes a display 405 and one or more input buttons that allow the user to enter information into the mobile computing device 400. The display 405 of the mobile computing device 400 may also function as an input device (e.g., a touch screen display). If included, an optional side input element allows further user input. The side input element may be a rotary switch, a button, a microphone or any other type of manual input element. In alternative aspects, computing device 400 may incorporate more or less input elements. The visual indicator 420 may be used to provide visual notifications, and/or an audio interface may be used for producing audible notifications via the audio transducer. In the illustrated embodiment, the visual indicator 420 is a light(s) emitting diode (LED) or other light-emitting system, and the audio transducer is a speaker. These devices may be directly coupled to the power supply so that when activated, they remain on for a duration dictated by the notification mechanism even though the computer processor(s) and other components might shut down for conserving battery power. The audio interface is used to provide audible signals to and receive audible signals from the therapist or AI therapist. For example, in addition to being coupled to the audio transducer the audio interface may also be coupled to a microphone to receive audible input, such as to facilitate a telephone conversation. In accordance with embodiments of the present disclosure, the microphone may also serve as an audio sensor to facilitate control of notifications, as will be described below. The system 430-450 may further include a virtual or augmented reality experience in 3D, including audio and visual components and light-emitting system. In addition, the aspects and functionalities described herein may operate over distributed systems (e.g., cloud-based computing systems), where application functionality, memory, data storage and retrieval and various processing functions may be operated remotely from each other over a distributed computing network, such as the Internet and intranet or in the Metaverse. User interfaces and information of various types may be displayed via on-board computing device displays or via remote display units associated with one or more computing devices. For example, user interfaces and information of various types may be displayed and interacted with on a wall surface onto which user interfaces and information of various types are projected. Interaction with the multitude of computing systems with which embodiments of the disclosure a 3D holographic interface 430 that enables an operation of an on-board light-emitting system to for expressing language in color ready for translation using biometric sensors, including quantum dots programmed for LU, and an audio system to communicate conversationally, and the like. A mobile computing device 400 implementing the system(s) may have additional features or functionality. For example, the computing device 400 may also include additional data storage devices (removable and/or non-removable) such as, magnetic disks, optical disks, or tape. Data/information generated or captured by the computing devices 400 and stored via the system may be stored locally on the mobile computing device 400, as described above, or the data may be stored on any number of storage media that may be accessed by the device via the audio interface layer or via a wired connection between the mobile computing device 400 and a separate computing device associated with the computing device 400, for example, a server computer in a distributed computing network, such as the Internet or Metaverse. As should be appreciated such data/information may be accessed via the mobile computing device 400 via the audio interface layer or via a distributed computing network. Similarly, such data/information may be readily transferred between computing devices for storage and use according to well-known data information transfer and storage means. Aspects of the present disclosure provide a system comprising: at least one computer processor; and memory coupled to the at least one computer processor, the memory comprising computer executable instructions that, when executed by the at least one computer processor, performs a method for creating an AI Therapy Assistant or a morphing avatar or agent.

Figure 5:
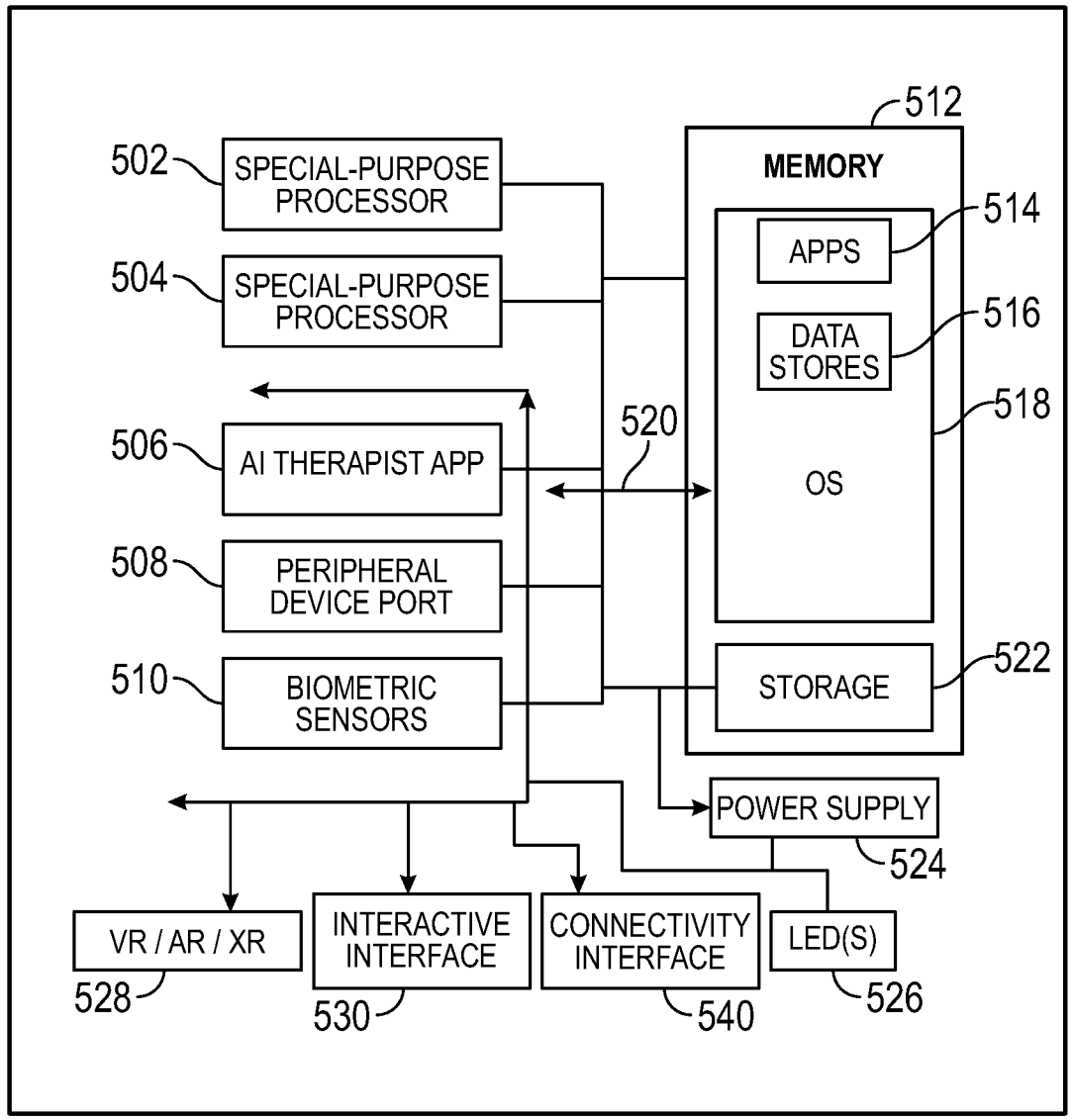
FIG. 5 is a simplified block diagram of a distributed computing system in which aspects of the present disclosure may be practiced.

FIG. 5 illustrates one aspect of the architecture of a system for processing data received at a computing system from a remote source, such as a personal computer 504, tablet computing device 506, or mobile computing device data. An AI therapist application 508 may be employed by a client that communicates with server device 504, and/or the AI therapist creation application 508 may be employed by server device 506. The server device 502 may provide data to and from a client computing device such as a personal computer 504, a tablet computing device 506 and/or an AI therapist display device 508 through a network 515. By way of example, the computer system described above may be embodied in a personal computer 504, a tablet computing device 506 and/or an AI therapist device 508. Any of these embodiments of the computing devices may obtain content from the store 520, in addition to receiving graphical data useable to be either pre-processed at a graphic-originating system, or post-processed at a receiving accessed chatbot therapist data in a data store 516; and providing an index generation engine access to the stored persona data. In some examples, the method further includes processing the persona data using at least one of machine learning techniques and one or more rule sets; and applying the processed persona data to the persona index to generate a customized persona index. In some examples, the persona index is associated with one or more data processing algorithms for processing the persona data, wherein the one or more data processing algorithms correspond to at least one of AI therapist interaction rules, image classification rules, and data acquisition rules. In some examples, training the AI therapist includes applying to the AI therapist at least one of a voice font, a 2D image, and a 3D image. In some examples, the method further includes submitting dialogue to the AI therapist; and generating, by the AI therapist, a response to the submitted dialogue, wherein generating the response includes utilizing a hierarchical data traversal process to collect response data from one or more data sources accessible to the computing system. By way of example, the computer system with computing device LED lights, described above may be embodied in a device 508 or within any interface on a computing device 504, 506 or on any and all devices, represented by an indicator, either by lights, colors, movement, verbal, etc.

Figure 6:
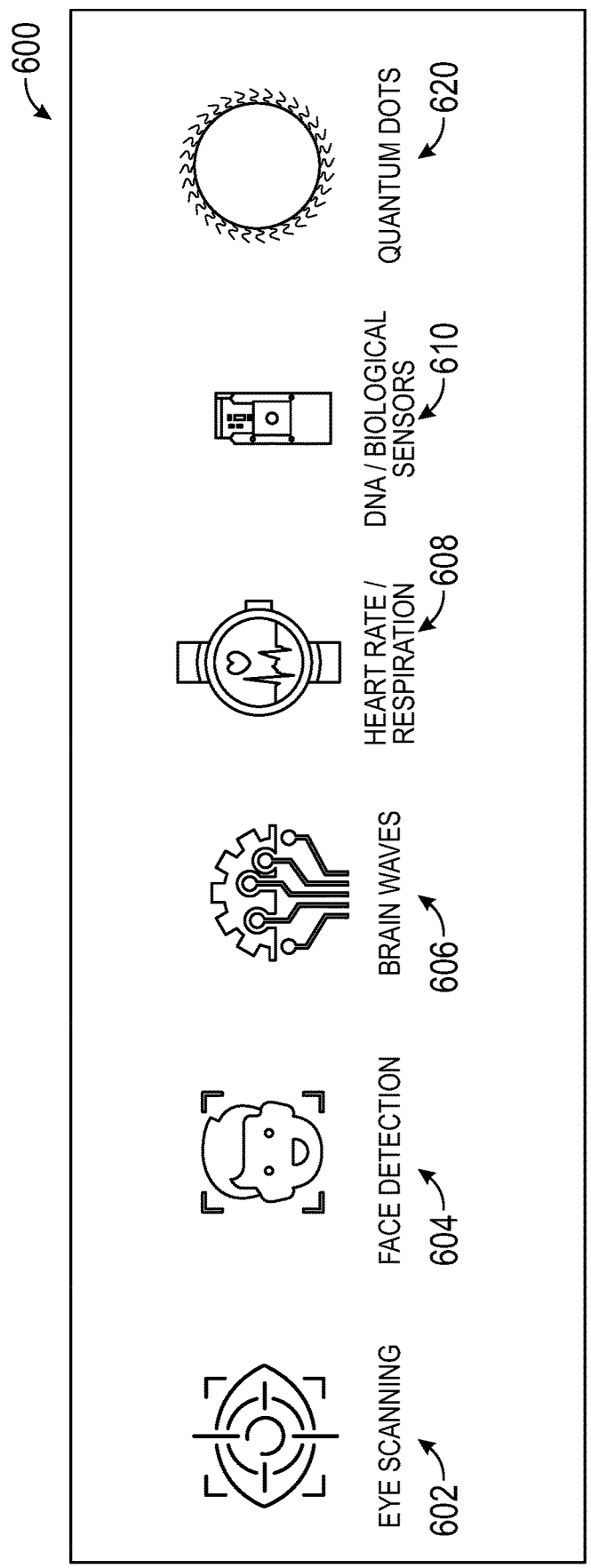
FIG. 6 are examples of biometric and biological sensors and with which aspects of the present disclosure may be practiced.

FIG. 6 illustrates an exemplary array of biometric sensors 600 that may execute one or more aspects disclosed herein. In some examples, the hierarchical data traversal process includes human response/reactions data to an environment including the Metaverse, delivering biometric responses in multiple different formats. The devices 602-630 are not limited to any number or type of biometric, haptic and/or biology-gated transistor sensor(s) but for example, biometric sensors to determine if eye movements, brain waves, brain activity on nervous system 602 convey a stress response, intent, emotions, words, meanings of words, etc., or if galvanic biometric sensors 608 are more reliable and/or any combination of biometric sensors. DNA and other biological systems can be measured by biology-gated transistors 610. Quantum dots 630, within the realm of nanotechnology can be programmed to accurately measure and transmit colors, specifically for a non-verbal language as outlined in this disclosure. Also, these Quantum dots 620 can be used to emit color based upon the stress response, either in a client device, object, glass, screen, substrate and/or in the Metaverse and including any 400 devices. These sensors can be used in any combination of software or hardware to supply the data used to determine the responses in any environment including the Metaverse. Aspects of the present disclosure further provide a computer-readable storage device storing computer executable instructions that when executed cause a computing system to perform a method for analyzing biometric sensor data in response to communication, non-verbal intent, motive, emotions, stress, among others. Hepatic sensors 620 and/or any other tactile sensors can transmit data and/or receive it. Furthermore, a computer-readable storage device storing computer executable instructions that when executed cause a computing system to non-verbal communication including words, meaning of words, emotions, stress, intent, motive among others, with knowledge base data and personal user information to validate accuracy of the data. In one embodiment the comparison of the sensor data may include a prediction percentage of validity when comparing the knowledge base data and the personal user data with the biometric sensor data as provided in this disclosure. The description and illustration of one or more aspects provided in this application are not intended to limit or restrict the scope of the disclosure as claimed in any way.

Figure 7:
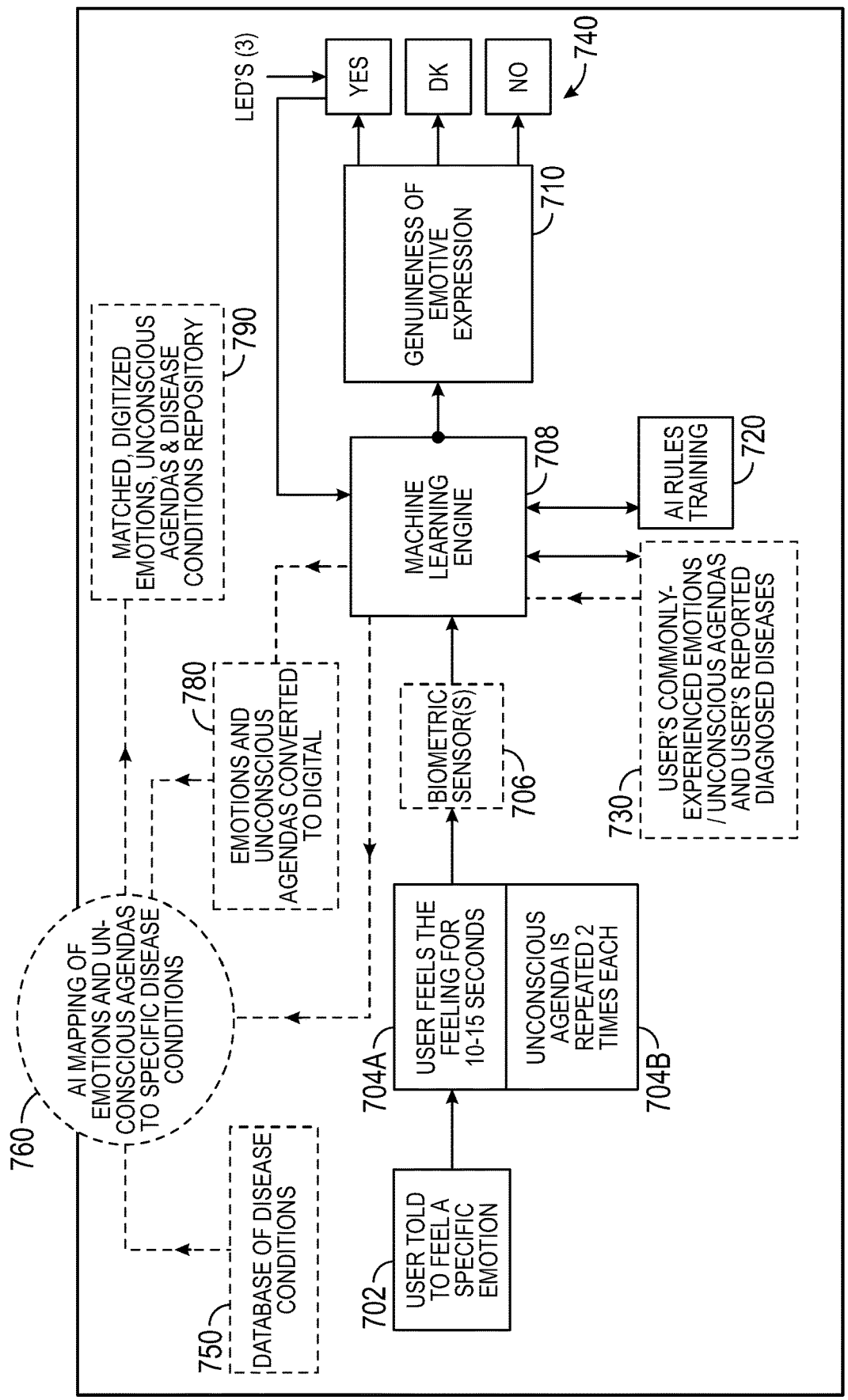
FIG. 7 illustrates components to digitize emotions and unconscious agendas by instructing a user to experience an emotion or repeat an unconscious agenda while being measured with biometric sensors, to the processing by machine learning to verify accuracy and distributing "yes" inputs by users to AI mapping between the emotion, unconscious agenda, to a disease condition, of the present disclosure may be practiced.

FIG. 7 illustrates an overview of an exemplary input processing unit 700 for digitizing emotions and unconscious agendas for correlating to user-data 730, as described herein. The digitizing and mapping of emotions and unconscious agendas with disease conditions 790 are a combination of techniques implemented by input process-components. In response to receiving the data assessed by biometric sensors or biological methods 706, machine learning engine 708 may access the yes answers 740 and the personal user data 730 and/or stored by AI rules training 720. Machine learning engine 708 may search for and receive data from biometric sensors 706 and predict the accuracy of yes, no and don't know answers 710, delivering a percentage of accuracy in one embodiment of the disclosure. Processing the data from feeling the feeling or stating an unconscious agenda by machine learning engine 708 with the knowledge base the user personal information 730 may further include determining and categorizing, rating, level of confidence in yes, no, or don't know answers.

The similarity score/metric may represent the estimated similarity between a number of users and their reported disease condition(s) with commonly felt emotions and unconscious agendas. In aspects, the processed customized data may be used to create, organize, populate or update rules training for an AI Therapy Assistant. The therapist 702, asks user to feel a feeling and hold the feeling for 10-15 seconds or ask the user to repeat an unconscious agenda at least two times 704A-B who then performs the requests while using biometric sensor(s) programmed to measure the accuracy of the answers. The yes and no or don't know interpreted answer(s) are then challenged by the machine learning engine by comparing the other user's personal information 730 with AI rules training 720 to predict the accuracy of the answer. After positive answer data 740 is available it is then correlated with other user's data that includes their reported diagnosed disease condition(s) and the emotions and unconscious agendas they commonly experience 730 to aggregate them with others that contain the same attributes. Feeling feelings 704A or stating unconscious agendas 704B can be done with the positive or negative aspect to receive a yes answer and a notation made in users records to address in the future if yes on the negative. In an embodiment that is not asking a question which the machine learning engine 708 is programmed to listen for, a button or switch will be required may be used to request a response to a statement 740. Finally, mapping occurs to the disease condition 750 and the emotions and unconscious agendas 780 based upon the frequency of similarities between multiple users with the same reported disease condition, emotions and unconscious agendas experienced frequently 730. In another embodiment users may be asked for the severity of their diagnosis rating it in one format or another. The resulting data 790 is then used in other implementations of one or more aspects provided in this application. It's the volume of data of personal users 730 with the same self-reported disease conditions and similar emotions, unconscious agendas experienced, to map known disease conditions 750 with digitized emotions and unconscious agendas 780 to process the mapping 760. In one embodiment, if five hundred of five thousand are similar, only five hundred would be mapped 790. The difference between various sets can be used to rate the percentage of confidence in the mapping of each 760. This process is then repeated for over eight hundred emotions, thousands of unconscious agendas and thousands of disease conditions but is not limited to any specific number, category, method or system. The communication method between the user 702, user 704A-B and the AI machine engine 708 can occur in any method from converting voice to text, for processing or by the AI machine engine learning conversational communication and may include using machine learned techniques and/or natural language processing techniques and may also include the use of latent semantic indexing, latent Dirichlet processing, word and/or sentence embedding models, collaborative filtering techniques, entity graphs, Jaccard similarity, cosine similarity and/or translation models. The description and illustration of one or more aspects provided in this application are not intended to limit or restrict the scope of the disclosure as claimed in any way.

Figure 8:
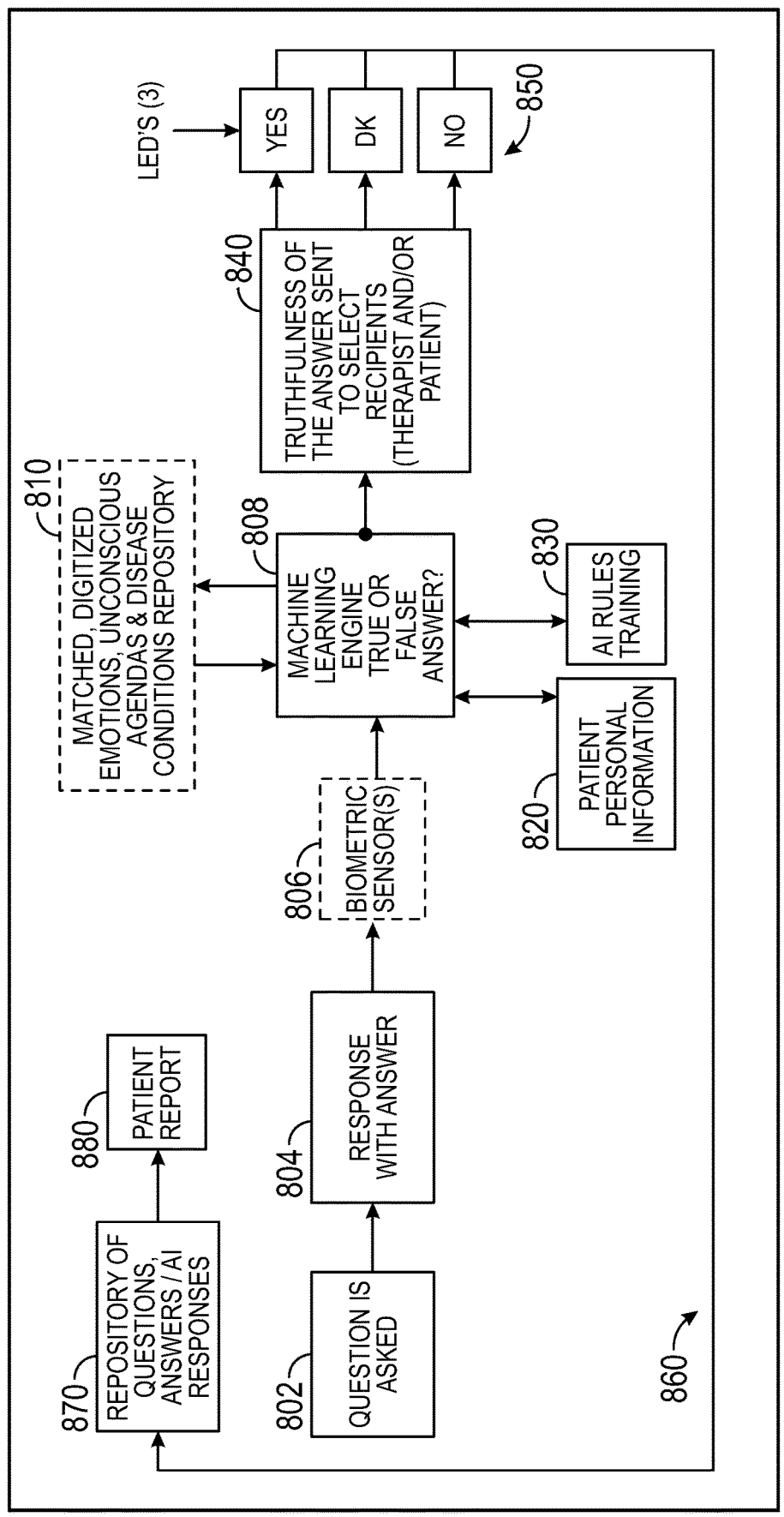
FIG. 8 illustrates question, answer, response aspects of the present disclosure may be practiced that includes comparing the digitized emotions, unconscious agendas, and matched disease conditions and the personal information of the user to determine validity of biometric sensor data.

FIG. 8 is an overview of another similar use and embodiment, a therapist 802 asks a question of a user 804 while biometric sensors 806 are applied by the user. The data being received by the machine learning engine 808 is processed by comparing and contrasting the digitized emotions, unconscious agendas and disease conditions 810 with the personal information of the user 820 that includes the most commonly experienced emotions and unconscious agendas and reported disease conditions that have been medically diagnosed, all according to the AI rules 830. The results of the machine learning engine 808 are determined 840 and indicated by signaling a yes, no, or don't know response 850. The results are added to a repository 870 that in one embodiment, can be accessed during the processing of the data 808 840 850. A user report 880 is available which provides an embodiment that deploys a "test" for a user to identify emotional risk factors underlying disease conditions. Any one or many components can exist simultaneously, be updated in real-time or otherwise, to provide ongoing training, including feedback loop(s) 870 808 to build learning upon learning over time and through experience of thousands of results reports. The machine learning engine 808 functions as an evaluator of truthful or untruthful answers 804 from the user or other user to questions posed by the therapist 802, or other user, in any field, industry, category, position, etc. including job performance, hiring success predictability, lie detector, loan applicant quality, and/or sports coach, etc. The description and illustration of one or more aspects provided in this application are not intended to limit or restrict the scope of the disclosure as claimed in any way. Processing the question-and-answer session 808 840 may further include a button or switch to ask for processing 840 from the machine learning engine 808 to add more control over the QA session and the processed 840 answer by the machine learning engine 808. In one embodiment, the therapist 802 may request an answer 850, then ask a question and automatically receive the answer. Yet other embodiments may have a button clicked after the question is asked to identify the question to test, especially if the line of questioning is significant and the therapist only has certain questions it wants assistance with. The process is built around questions that the Machine learning engine 808 listens for and hence gating of the answers 850 will require use options. In another embodiment, the methods and systems can be used as a test to measure the truth of any question including, "Are you aware of how you feel consciously?" "Are you an honest person?" "Are you ever late for work?" "Do you have a criminal record?" This provides a genuine response to questions that are typically asked when getting a loan, applying for a job, etc. Another embodiment of the methods and systems herein can answer questions 840 when the emotions are not matched with disease conditions or even non-digitized emotions. The description and illustration of one or more aspects provided in this application are not intended to limit or restrict the scope of the disclosure as claimed in any way.

Figure 9:
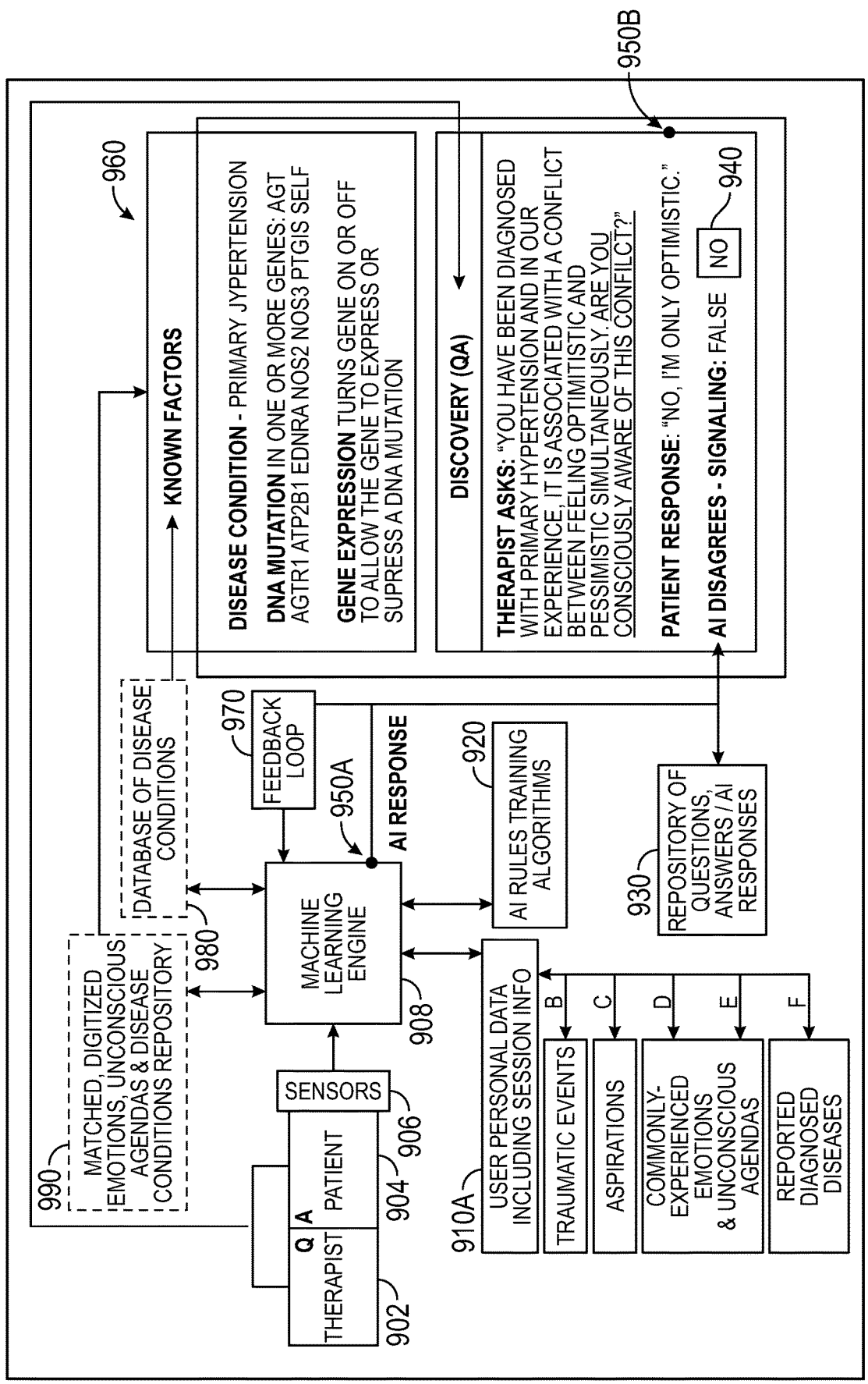
FIG. 9 illustrates detailed view of FIG. 8 and includes the dialogue that occurs between the therapist and the user, using the AI Therapy Assistant, aspects of the present disclosure may be practiced, starting with a question from the therapist that the user answers while being monitored by sensors, processed by machine learning making its assigned comparisons to signal a true or false answer to the question, directing the line of questioning.

FIG. 9 is a detailed view of an exemplary input and response processing unit 800 for creating an AI Therapy Assistant as described herein. Any version is a combination of techniques implemented by input process-components accessible by a user on a client device FIG. 4. In response to receiving the request posed as a question from a therapist 902 of the user/user 904 and answered while applying biometric sensors(s) data 906, the machine learning engine 908 may access the repositories of matched, digitized emotions, unconscious agendas and disease conditions 990 and the personal user data 910A-F with AI rules training 920 that also includes data updates from the feedback loop 970 to accomplish its task of processing 908 to conclude an analysis of the answer: Is the user's 904 answer 950A-B true or false? Machine learning engine 908 predicts the accuracy of yes, no and don't know answers 940 delivering a percentage of accuracy in one embodiment of the systems and methods. Processing the data from answers 904 950A-B using biometric sensor data 906 by machine learning engine 908 of the validity of user answers 904 with the repository of previous questions, answers, and AI responses 930, matched, digitized emotions, unconscious agendas and disease conditions 990 and the user personal information 910A-F may further include a scoring or comparison algorithm/model for evaluation. The scoring or comparison algorithm/model may generate and/or assign scores or labels to the evaluated characteristics. The scoring or comparison algorithm/model may use the generated scores/labels to determine a similarity score or metric for an AI therapy assistant. The similarity score/metric may represent the estimated similarity between multiple therapist questions 902 multiple user answers 904, and/or multiple AI responses 930 940. In aspects, the scoring data may be used to create, organize, populate or update an AI therapy assistant that determines true, false or don't know answers 940. In another embodiment, the database of disease conditions 980 is available for a therapy session to specifically help a user address the underlying emotional risk factors involved in disease, specifically. In this use case a user 902 might want to be "tested" on what is already known in the matched, digitized emotions, unconscious agendas with disease conditions 990 to prevent a disease before it ever presents symptoms. The user 904 trains the machine learning engine by submitting personal user data including personal stories of trauma, devastating events, emotional issues 910B, aspirations 910C, and the diseases they are diagnosed with 910F as well as the emotions and unconscious agendas that he/she experiences commonly 910E. In another embodiment, a user might also be "tested" for the emotions 990 related to a specific disease 990 that is known as hereditary to then prevent its occurrence. AI rules training 920 provides the algorithms that direct the machine learning engine 908 and includes taking into account the conscience of a human knowing that human responses are often tempered and yet others are overly blunt. Considering this disclosure is tapping into unconscious reactions to conscious answers, these three elements must are analyzed together to determine the truth of an answer at a highly effective rate 99.99%. The algorithms in AI rule training 920 are proprietary and include measuring emotional flavors that users choose to convey that can identify a personality type based on word choice. They may also include asking multiple questions by a therapist 902 of a user 904 to determine what life event shaped the unconscious agenda 910B 910E. In another embodiment focus on rules will be applied in the AI rules training 920. Also, new algorithms may be added in other embodiments of the AI rules 920 depending upon use case such as measuring the talent and the shortcomings of an athlete emotionally/mentally would include the rules of the sport the athlete performs in to associate unconscious agendas with possible uneasiness when a certain event occurs on the field such as a quarterback, with three sacks early in the game, can the athlete put that out of his mind and unconscious to avoid having it affect performance for the rest of the game? AI machine learning 908 used to tap into the unconscious requires involves understanding of the elements of the use case coming from the AI rules 920. The dialogue diagram in light gray 960 provides insight into the actual process that could occur with a therapist interested in tackling disease conditions and how they are associated with emotions and unconscious agendas 990. Even detail about DNA mutations and/or DNA expression associated with a disease would be the starting point knowing that in FIG. 10 there is a process to verify success of the process 1060A. The therapist 902 then conveys what is known to the user 904 and asks a question, "Are you consciously aware of this conflict?" The user 904 says, "No, I'm only optimistic 950B." The machine learning engine 908 processes the answer by analyzing the biometric sensor data 906, the user personal data 910A-F with matched, digitized emotions, unconscious agendas and disease conditions 990 using AI rules 920 and of course its own AI engine 908 insight. This process finds that the answer given 950B is false 940. The line of questioning would continue such as, "Well it looks like there might be an area in your life you might want to look at, about being pessimistic, etc." During this QA 902 904 and in various embodiments the results 950A-B can be held back, be automatic, be repeated, or be requested, or any other method/format to create a smooth question, answer, result methodology. The description and illustration of one or more aspects provided in this application are not intended to limit or restrict the scope of the disclosure as claimed in any way.

In one aspect, an emotional or mental belief system reprogramming system is disclosed. The system includes a digital framework including a pattern recognition module configured to identify and recommend reprogramming and alter a health status of a user, the digital framework includes (1) a digitally recorded library of human emotions, unconscious agendas, perceptions, beliefs, and mindsets of a control group of users selected from a population of users (2) a question engine configured to interrogate the user using a library of predetermined questions and to identify a plurality of underlying unconscious agendas of the user that generate behavior of the user and associated negative emotions of the user, (3) an expressive, experiential digital agent having digitized color, gestures, expressions, movements, emotions, beliefs, intent, intuition, and haptic effects, the digital agent configured to interact with the user in real time, to ask questions, to engage the user, and to direct the user to perform certain tasks, wherein the digital agent comprises a conversational digital avatar, and/or a conversational chatbot, (4) a plurality of sensors communicably connected to the digital framework and to the user during a question-answer session with a therapist, chatbot, avatar, coach, friend as a means of engaging the question engine, each of the plurality of sensors configured to communicate, record and report at least one of: a physiological state or an emotional state of the user while responding to a plurality of questions posed by the therapist, chatbot, avatar, coach, friend as a means of engaging the question engine during the question-answer session, (5) a baseline measuring module configured to evaluate the user's responses and reactions to the questions posed by the therapist, chatbot, avatar, coach, friend as a means of engaging the question engine, and to determine and differentiate between a valid answer and an invalid answer, and thereby to construct a baseline measure for the user, and (6) a reprogramming module configured to identify and recommend reprogramming of a plurality of negative beliefs of the user, accomplished through relaxation, breathing, recording and repeating a plurality of de-programming and reprogramming statements, confirmed as accurate, by the digital framework through an analysis of the plurality of sensors data in combination with the underlying unconscious agendas of the user.

The emotional or mental belief system reprogramming system further includes a user engagement level gauge configured to record and display the user's engagement level with the therapist, chatbot, avatar, coach, or friend during the question-answer session.

The emotional or mental belief system reprogramming system further includes a datastore of assets including a library of digitized options to suggest, offer to a user and validated, or not, by a validation engine, during the question-answer session.

The emotional or mental belief system reprogramming system wherein the library of digitized options to suggest, offer, validate comprises a plurality of digitized humanizing features comprising empathy, pacing of conversation, offering emotional validation to be offered by the therapist or the question engine during the question-answer session.

The emotional or mental belief system reprogramming system wherein the plurality of sensors comprise biometric sensors configured to perform at least one of: detection of eye and/or facial movements, monitoring of pulse, respiration, blood pressure changes, brain waves and/or changes in gene expression of the user.

The emotional or mental belief system reprogramming system wherein the pattern recognition module comprises an artificial intelligence architecture configured to analyze the plurality of sensors data in combination with the underlying unconscious agendas of the user.

The emotional or mental belief system reprogramming system wherein the pattern recognition module comprises a machine learning module configured to train the digital framework based on a set of rules to translate the user's response from a plurality of digitally recorded questions and/or suggested answers, and to interpret a plurality of outputs from the sensors.

The emotional or mental belief system reprogramming system wherein the digital framework is stored in a secure, distributed storage network comprising at least one of: a block chain application and a distributed database application.

The emotional or mental belief system reprogramming system wherein the digital framework is installed on at least one of: a mobile telephone, a personal digital assistant, a computer and a distributed network system, wherein the digital framework is accessed from the at least one of: the mobile telephone, the personal digital assistant, the computer and the distributed network system, and wherein the digital framework is operationalized from the at least one of: the mobile telephone, the personal digital assistant, the computer and the distributed network system.

The present disclosure provides systems and methods of creating a morphing avatar, agent that embodies human characteristics for enhancing awareness, protection and equipment of a universal language for real-time communication. The personas that can be modified to obscure, enhance or reflect a virtual agent can be any person, place, object, real or imagined and is not limited to just a human representation. The format of the persona, avatar, or virtual agent is also expansive in that the features are contained in colors, resonance, or even exist as an intuition or inner voice with no appearance (cloaked, with minimal virtual representation). Texture, size or other features are also not to be limited to what we commonly know as human. The embodiment of human characteristics is also not limited to intuition amplification, addition of a stress response system SRS, or better known as the fight or flight response but can extend to emotive or cognitive expression in a non-verbal form. Intent, another feature that makes humans human, is also embodied in the virtual agent along with creative decision-making. Experience between the virtual agent and the local user can be shared through haptic transmission and/or any other systems and methods, creating a "dual, simultaneous experience."

Machine learning models assist in all aspects related to human characteristics for continued mirroring, including a real-world experience of the virtual world. In examples, a model may be a rule-based model, machine-learning regressor, a machine learning classifier, a neural network, or the like. In some aspects, conversing in the Metaverse may include determining and/or using conversational attributes, such as style, diction, tone, voice, intent, sentence/dialogue length and complexity, topic and consistency. Conversing may include behavioral attributes such as gestures, movements, or facial expressions including experiencing feelings, intent and intuition.

In aspects, photos and videos are converted to 3D objects for producing an avatar, virtual agent, or other object for embodying human characteristics. The photos and video snippets are stored and converted on the fly and include all races, sizes, shapes, and colors. In another embodiments, these photos and videos may be of other objects, places, things, or a cloaked experience. Repositories hold data of converted information related to color and its match to word or meanings, emotions or intent converted to colors. In addition to colors, machine learning is associated with use of the data repositories.

Figure 10:
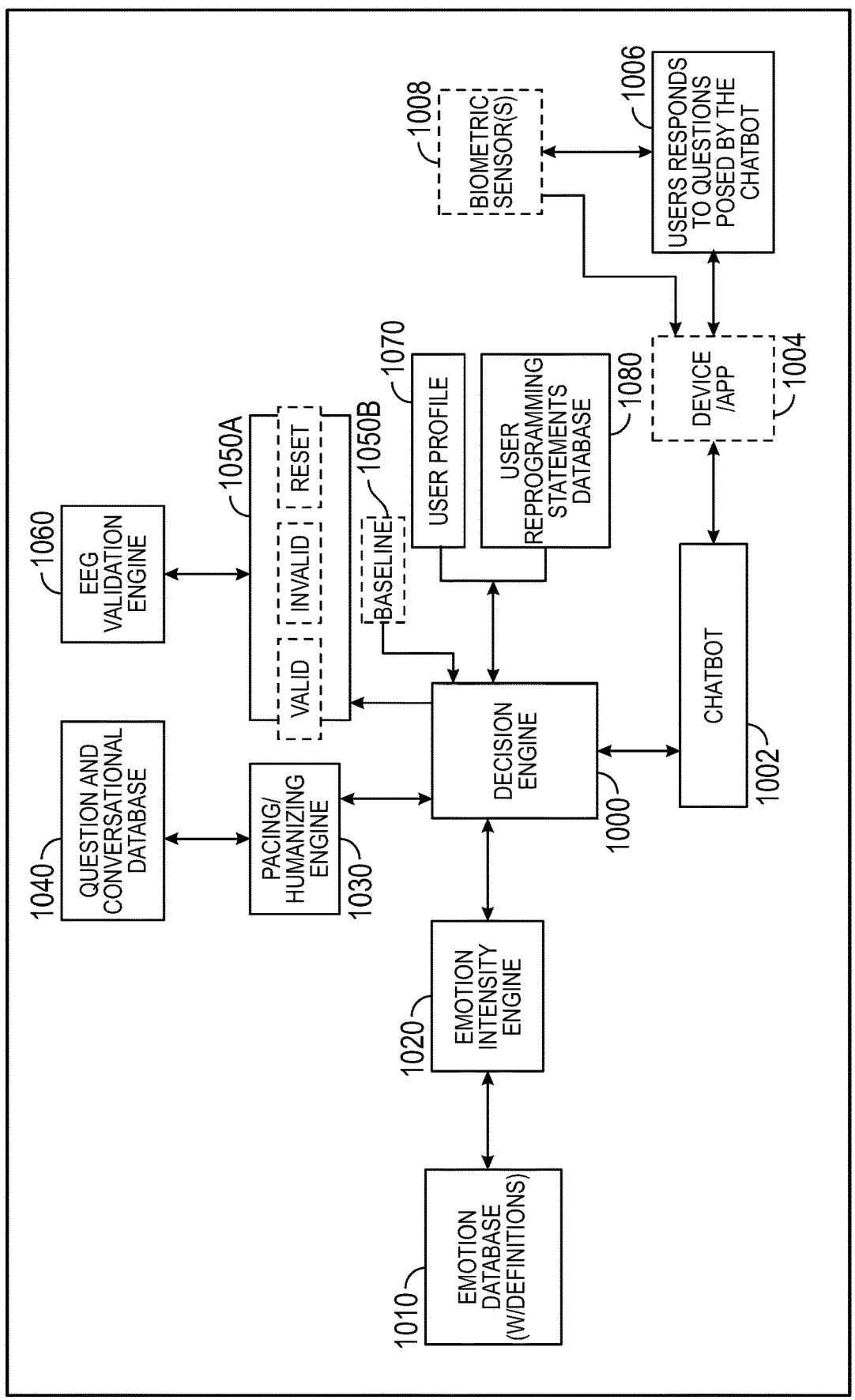
FIG. 10 illustrates a health status reprogramming system including a digital framework that includes a pattern recognition module configured to record and report a health status of a user.

FIG. 10 illustrates emotional or mental belief system reprogramming system including a digital framework that includes a pattern recognition module configured to record and report a health status of a user. Referring to FIG. 10, 1000 is the core of the software where decisions are made, all except the EEG Validation Engine 1060 and its decision output 1050A & B. 1002 is the Chatbot that will ultimately be an avatar—it's where a user engages with the app in a conversational style, answering questions posed by the chatbot; chatbot starts asking the baseline questions first, each session. 1004 is the device with the app accessible on it and includes functionality from administering one's profile but also chatting with the chatbot, storing reprogramming statements locally (and to the network) and a recording and playback area for them. 1006 is the user, 1008 are the biometric sensors and in these two use cases is a headset with sensors that measure brain waves by connecting to the app using Bluetooth. 1010 is a database of emotions and their definitions for use in the chatbot line of questioning, asking a user how he/she feels when in a specific situation (helps a real therapist and client identify the feeling tagged to a perception about a previous experienced, cataloged in the brain). 1020 is an intensity measuring engine that asks a user to determine 2 things, how strong is an emotion (trauma, difficult or annoying) and to reduce the number of emotions delivered to select from anguished, banished, bleak, barren, bashful, bereft, and blue.

Tell me how you feel when this behavior occurs?

1030 helps to humanize the user experience with the chatbot and ultimately with an avatar—includes adding empathy-laced words, expressions, behaviors, responses, etc. . . . 1040 contains the actual sets of questions, both hard coded, and dynamically created in the AI version. 1050 are the results of analysis of the brainwaves. 1060 is where the processing occurs. The algorithm will remain unpublished but includes measuring all or a select group of sensors, the full array of brainwaves, and applying math to compute the widest range between a low stress answer (true statement) and a high stress answer (false answer).

Figure 11:
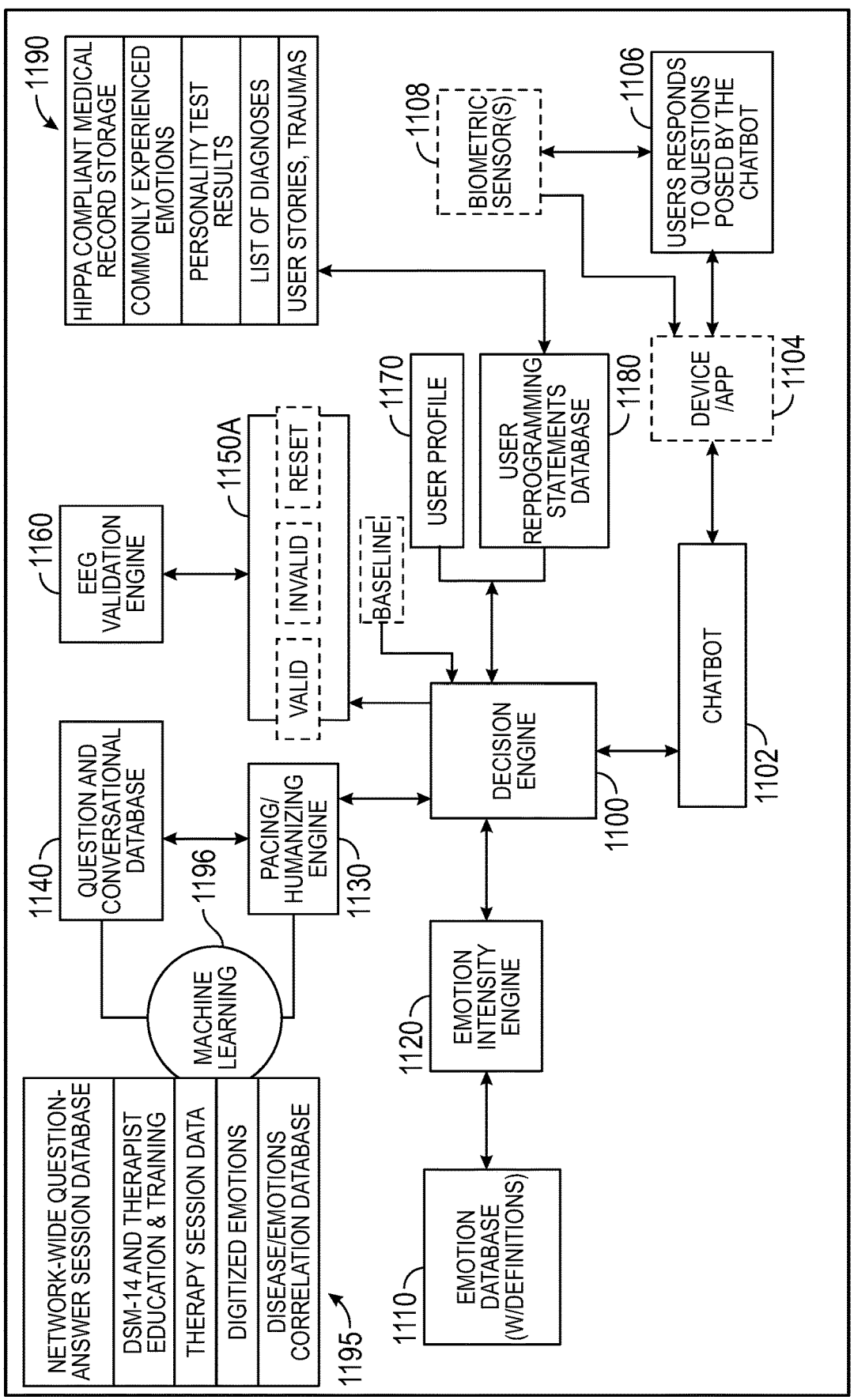
FIG. 11 illustrates an alternate overview of the health status reprogramming system of FIG. 10 including a digital framework that includes a pattern recognition module configured to record and report a health status of a user.

FIG. 11 illustrates an alternate overview of the emotional or mental belief system reprogramming system of FIG. 10 including a digital framework that includes a pattern recognition module configured to record and report a health status of a user. FIG. 11 is the same as FIG. 10 with 3 additional components. 1190 is an expansion of the user profile, provided by the user or by an integration with a healthcare platform. 1195 is a new knowledge center to support machine learning, to become a full-fledged licensable therapist. 1196 is the machine learning component. The machine learning component 1196 may get progressively enriched with improvements in Artificial Intelligence (AI) technology, as needed to continually improve the functionality of the therapeutic model.

Figure 12:
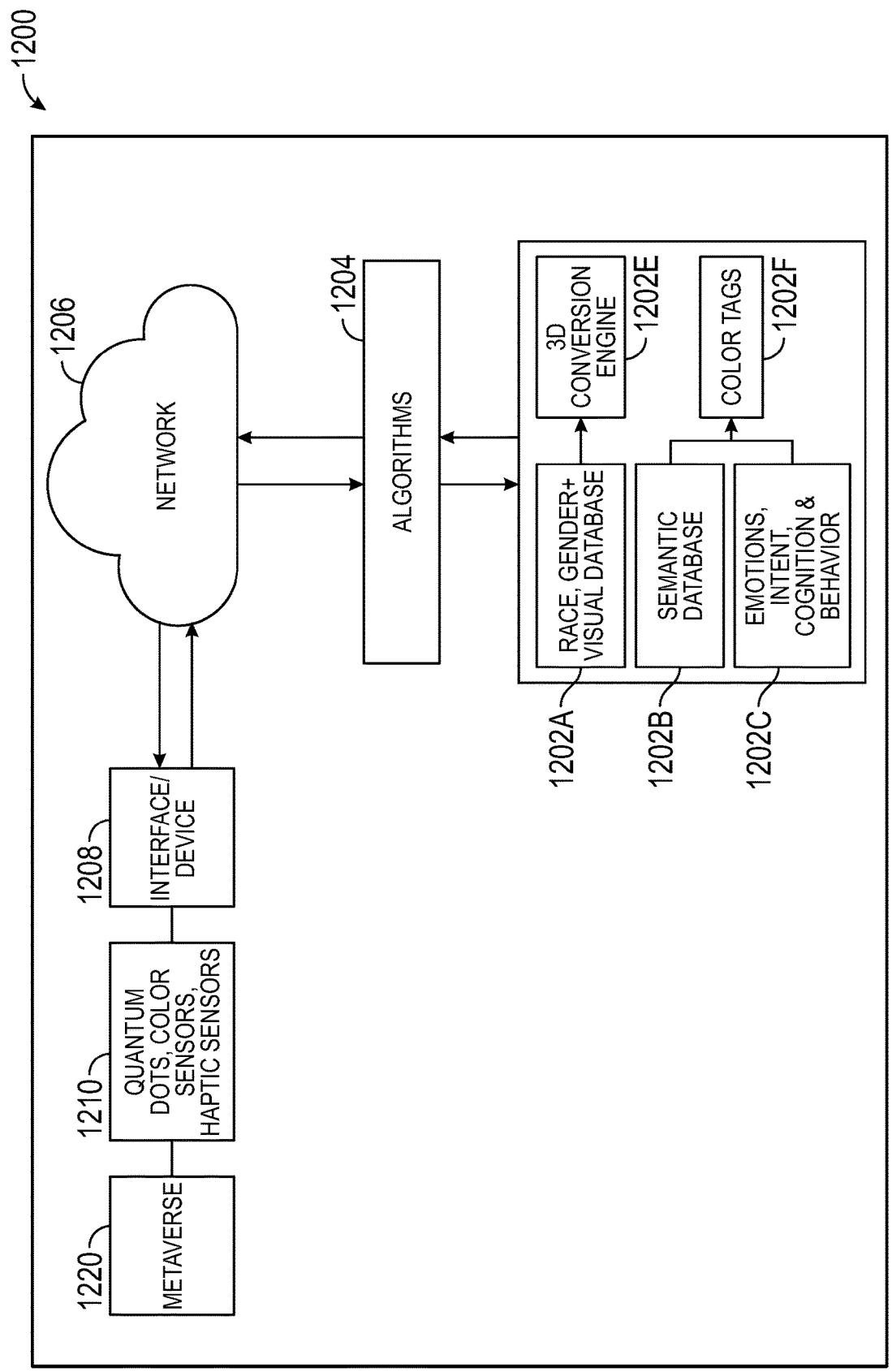
FIG. 12 illustrates an overview of an exemplary system for creating an expressive, auto-morphing Metaverse virtual agent as described herein.

FIG. 12 illustrates an overview of an example for creating a morphing avatar as described herein. Exemplary system 1200 may be a combination of interdependent components that interact to form an integrated whole for performing task management. In aspects, system 1200 may include hardware components (e.g., used to execute/run an operating system (OS)), and/or software components (e.g., applications, application programming interfaces (APIs), modules, virtual machines, runtime libraries, etc.) running on hardware. In particular aspects, system 1200 may provide an environment for soft ware components to execute, evaluate operational constraint sets, and utilize resources or facilities of the system 1200. In such aspects, the environment may include, or be installed on, one or more processing devices. For instance, software (e.g., applications, operational instructions, modules, etc.) may be run on a processing device such as a computer, mobile device (e.g., smartphone/phone, tablet, laptop, personal digital assistant (PDA etc.) and/or any other electronic device. As an example of a processing device operating environment, refer to the exemplary operating environments depicted in FIGS. 4-6. In other instances, the components of systems disclosed herein may be distributed across and executable by multiple interfaces. For example, input may be entered on a client device and information may be processed or accessed from other devices in a network (e.g., server devices, network appliances, other client devices, etc.).

As presented, system 1200 includes client devices 1208, distributed network 1206, and a distributed server environment include one or more servers, such as server devices and datastores 1202A-F. One of skill in the art will appreciate that the scale of systems such as system 1200 may vary and may include additional or fewer components than those described herein.

In some aspects, interfacing between components of the system 1200 may occur remotely, for example, where components of system 1200 may be distributed across one or more devices of a distributed network.

In aspects, client devices 1208 may be configured to receive input and send output via a user interface component or other input means. Examples of input may include voice, visual, emotional expression, gestures, movements, colors, and text input. In examples, one or more portions of the input may correspond to human characteristics data associated with the user 1220 and may store the data and/or provide access to data sources include data for the one or more characteristics in server datastores 1202A-F. The data sources may be located on, or accessible to, server devices 1202A-F via network 1206. As an example, client devices 1208 may provide access to user profile data and avatar configurations integrated with human characteristics 1202A-F. Such data may be locally stored on client devices 1208, or on one or more of server devices 1202A-F. In some aspects, client devices 1208 may have access to the index generation engine (or an instance thereof). The sensors 1210 are integrated with the user interface 1208 to provide input and output for communicating in the Metaverse.

In aspects, client devices 1208 may provide an index generation engine (or portions thereof) and/or a personalized index system (or portions thereof) of an avatar. The avatar may be located locally on a client device 1208, in the Metaverse 1220 or in another undisclosed environment, or some combination thereof. The avatar model may use the index generation engine to train the avatar to interact in accordance with one or more human characteristics in the Metaverse 1220 or other environment. For example, client devices 1208 may provide a personalized index generation engine to an avatar, displayed and interactive with human characteristics, or in the Metaverse 1220 or other environment. The avatar's persona may be trained using the personalized index generation engine to interact conversationally with the characteristics of a real-life. An instance of the trained, personalized avatar may be transmitted to one or more client devices and/or server devices. In some aspects, client devices 1208 may have access to a one or more language interpretations provided by color matching 1202B-1202F. A chat index, as used herein, may refer to a repository of conversational data include human characteristics and/or conversational algorithms associated with a plurality of users, events and conversational scenarios. As an example, a chat index may include question and answer information from another person, question and answer information from a person or entity, general information related to a specific persona, generic information persona relating to a particular topic or time period.

In aspects, client devices 1208 may provide for creating and/or applying a voice font for an avatar. For example, client devices 1208 may use Speech recognition and/or speech synthesis techniques may be applied to the voice data to create a voice font and include the conversion of words, meanings of words, emotions or intention, each to a unique color based upon the sender's language and then translated to the receiving party's language. The models and/or algorithms for implementing such techniques may be provided by client devices 1208, server devices and repositories 1202A-F, algorithms 1204 or a separate device/service and or algorithms 1204. The voice and/or language font and/or visualizations may then be applied to a morphing avatar to enable the avatar to converse in the voice of a specific or random person. In some aspects, client devices 1208, extending into the Metaverse 1220, may further provide for creating and/or applying a 3D model to an avatar. For example, client devices 1202A-F may access image data to create a 3D model of the specific gender, race or merging of genders and races. Additionally, or alternatively, client devices 1202A-F may access image data and/or 3D data (e.g., photos, video snippets, behavior information 1202C, color mapping information 1202F, etc.) included in server repositories, an index generation engine or other data sources. The image data and/or 3D data may be applied to a 3D modelling algorithm or service to create a 3D model of avatar or entity.

In aspects, sensors 1210 may provide a system to detect brain waves, brain activity and/or nervous activity in the brain to then interpret level of stress associated with Metaverse engagement as experienced by the avatar including transmitting Haptic data for local experience, and vice-versa. The sensors 1210 are connected to network 1206 through the client device 1208 and is interpreted with algorithms 1204. The biometric sensors, in another embodiment, sense colors and or other experiential data, emitted from the Metaverse 1220 and connected to the network 1206 through the client device 1208, for conversion by the conversion engine 1202E to convert colors to words, into meaning, intent, and/or emotion, intent, intuition, even touch, or any combination thereof.

Figure 13:
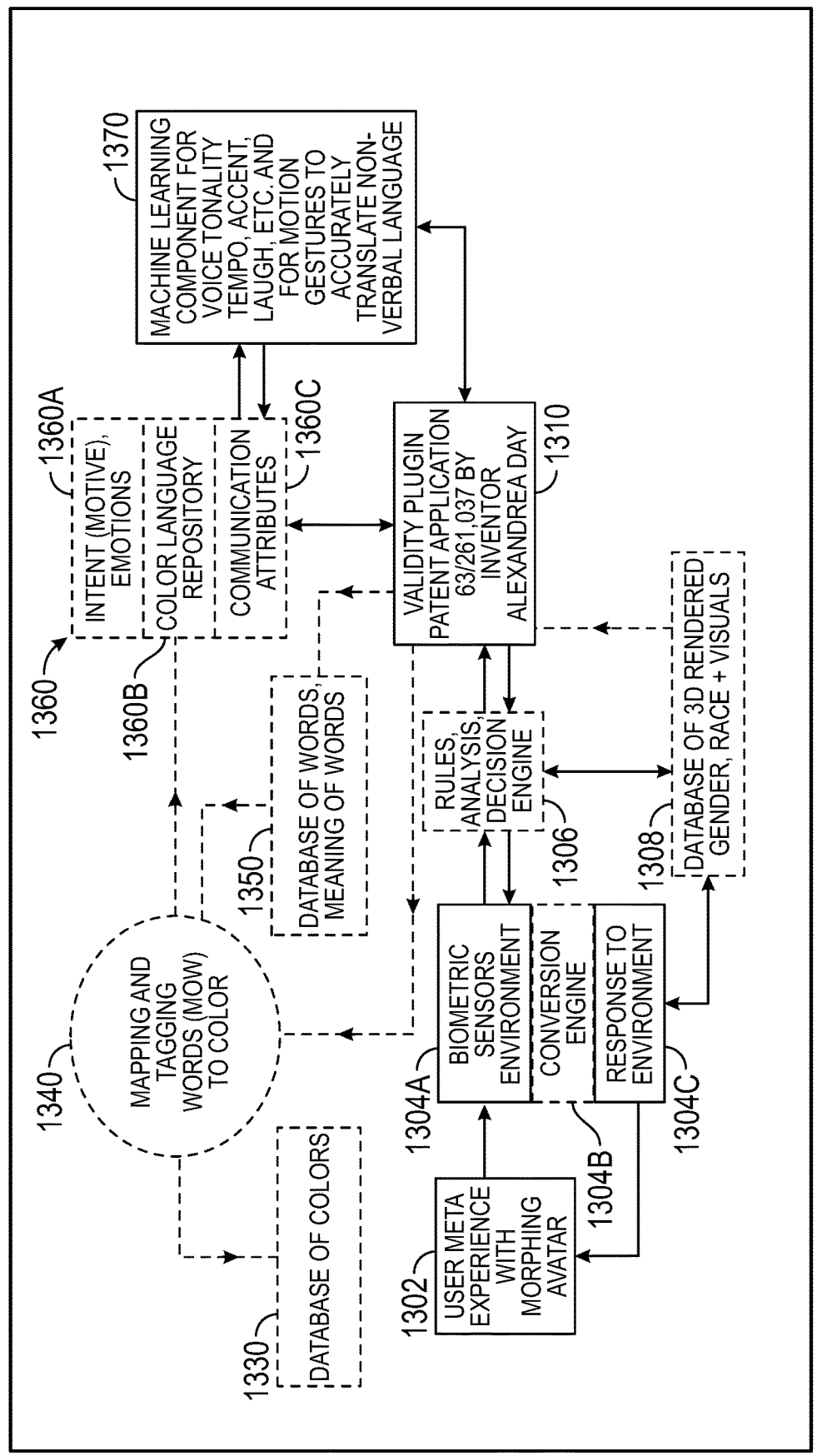
FIG. 13 is a simplified block diagram of a distributed computing system in which aspects of the present disclosure may be practiced.

FIG. 13 illustrates an overview of an exemplary input processing unit 1300 for creating a color-coded, universal, non-verbal language and to infuse and avatar or agent with intent, emotions, words, meaning of words, and other communication attributes for correlating to rendered morphing avatar or agent with blended race and gender 1308, as elected, as described herein. The digitizing and mapping of words and meaning of words 1340 are a combination of techniques implemented by input process-components. In response to receiving the data assessed by biometric, haptic sensors or biological methods 1304A, machine learning engine 1370 may access Haptic data 1360A intent 1360B, color language repository 1360C and communication attributes 1360D and/or stored by AI rules training 1370, in order to make a decision in the conversion engine 1304B. Machine learning engine 1370 may search for and receive data from biometric sensors 1304A and predict the accuracy of the incoming data from an environment including the Metaverse 1302, delivering a percentage of accuracy in one embodiment of the disclosure. Processing the data from sensors 1304A by machine learning engine 1370 with the knowledge base of non-verbal or verbal communication, intent, emotions, and physical experience (haptic) 1360A may further include determining and categorizing, rating, level of confidence in the data received from the sensors 1304A. The similarity score/metric may represent the estimated similarity between a number of users and their responses with commonly understood words, meaning of words, emotions, intent, etc. In aspects, the processed customized data may be used to create, organize, populate or update rules training for a Morphing avatar or agent. The response to the environment 1304C asks user asks questions verbally which are converted to color either by individual word or meaning of words 1350 before transmitting 1304C to the environment or into the Metaverse who then receives the requests also using, wearing biometric sensor(s) 1304A programmed to communicate non-verbally in color, intent, emotions, stress response, and/or gestures, etc. These are then interpreted by the machine learning engine 1370 by comparing the other user's incoming data through the biometric sensors 1304A. AI rules training 1304A is to predict the accuracy of the non-verbal communication data or sensed haptic data 1360A. Finally, mapping occurs between a specific assigned color to a word, meaning of words 1360C, intent, emotions 1360B and other communication attributes 1360D based upon the frequency of similarities between multiple users with the same words, meaning of words 1350, intent, emotions to then provide the data to the color translation engine 1304B. Communication attributes 1360D represents spoken word and non-verbal cues represented by bodily movement, facial expression, and the like. The resulting data creates the rules, analysis, and decision engine 1306 that is then used in other implementations of one or more aspects provided in this application. It's the volume of data of avatars, agent users 1302 with matching results data to improve all aspects of this disclosure. The communication method between the user 1302, user and any environment including the Metaverse can occur in any method from converting voice to text to color 1306C for processing or by the AI machine engine learning conversational communication of non-verbal communication and may include using machine learned techniques and/or natural language processing techniques and may also include the use of latent semantic indexing, latent Dirichlet processing, word and/or sentence embedding models, collaborative filtering techniques, entity graphs, Jaccard similarity, cosine similarity and/or translation models. The description and illustration of one or more aspects provided in this application are not intended to limit or restrict the scope of the disclosure as claimed in any way.

Figure 14:
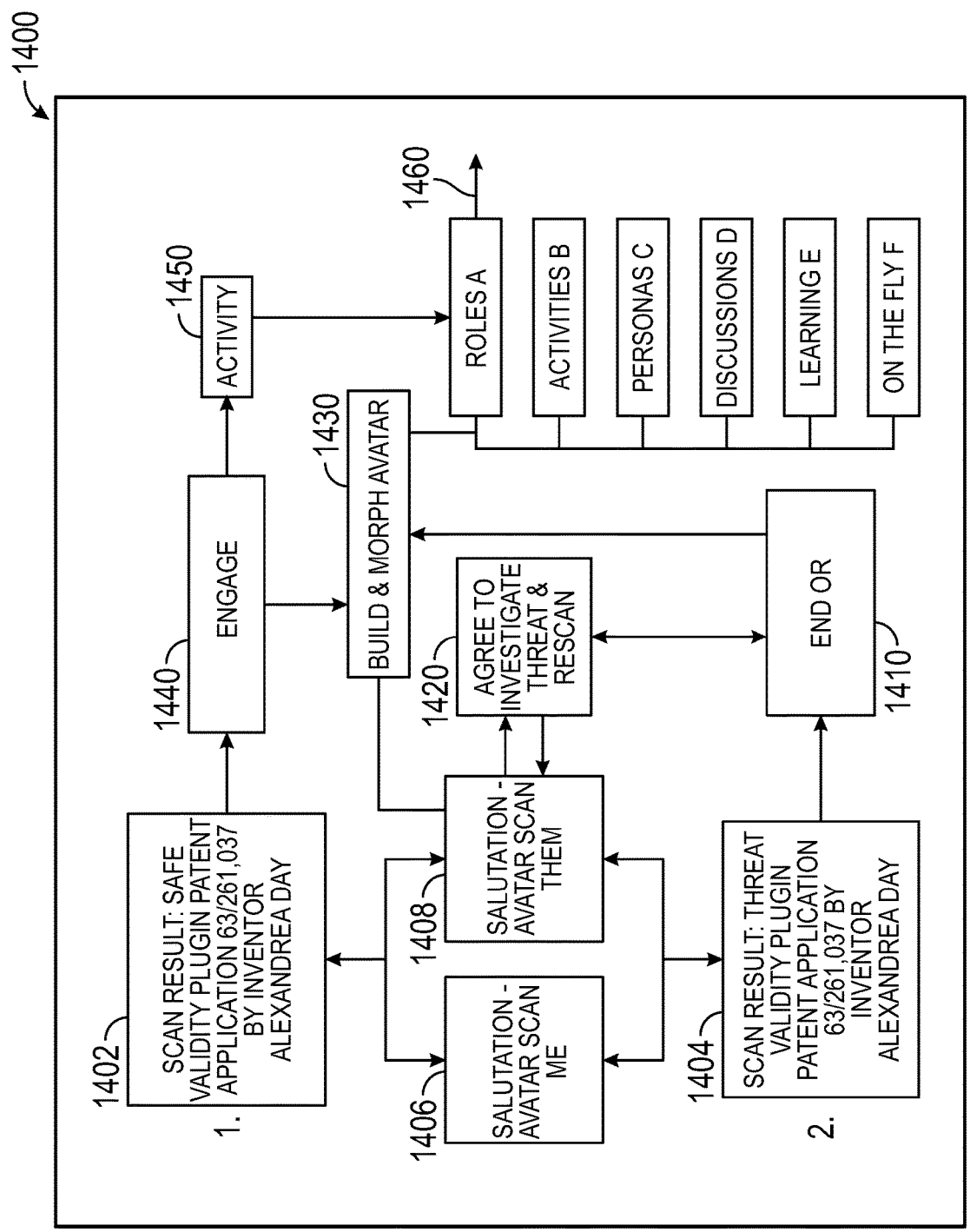
FIG. 14 illustrates the process by which data is gathered and responded to in the Metaverse between the avatar contemplated in this disclosure and another person or group, as described herein.

FIG. 14 is an overview of another similar use and embodiment, a validation system 1400 is an overview of two or more avatars or agents in an environment including the Metaverse 1406 and 1408 while scanning with biometric sensors by both users to validate threat, or not, of each as described in this disclosure. If scan is validated as safe 1402, engagement with the other is commenced. If the results are a threat 1404, session ends 1410 or a re-evaluation 1420 can commence, if agreed to by both parties. The data being received from the sensors worn by avatar, agent 1406 and 1408 is processed by measuring the stress response from each other's presence. Safe results 1402 allows for engagement 1440 in an activity 1450 and in a role 1460A-F, between the environment, Metaverse with an avatar, agent. Any one or many components can exist simultaneously, be updated in real-time or otherwise, to provide morphing avatars, agents, the ability to quickly adapt to their environment including the Metaverse. Non-verbal cues, language, both body movements, gestures, and facial expressions among others, words, utterances, are all monitored, analyzed and interpreted for intent, meaning, and in the case of threat, as described in this disclosure.

Figure 15:
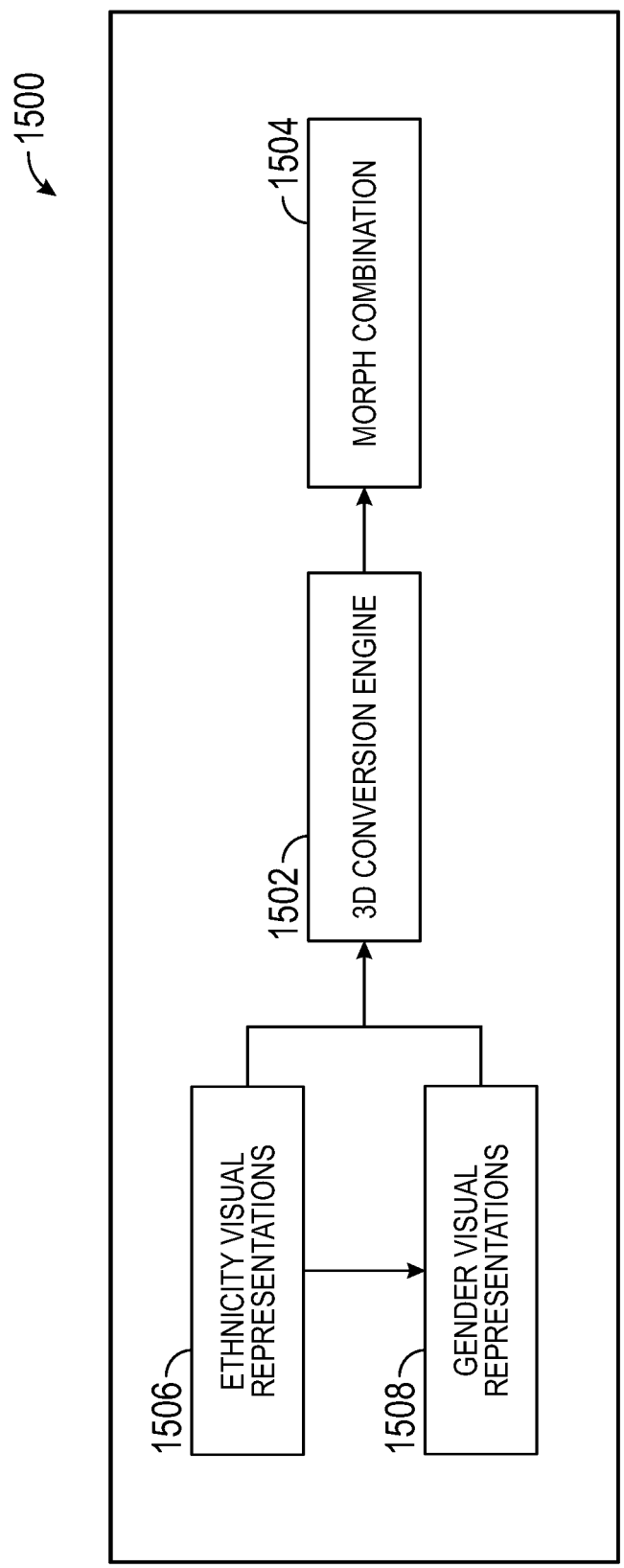
FIG. 15 introduces the integration and function of the prediction system's methods and systems, with the present disclosure as described herein.

FIG. 15 is an overview of an exemplary input and response processing unit 1500 for creating a Morphing avatar or agent as described herein. Any version is a combination of techniques implemented by input process-components accessible by a user on a client device FIG. 4. In response to receiving the request posed as a change in environment, including the Metaverse, to initiate morphing of an avatar or agent such as a threat, safety resuming, to blend in, to participate in an activity or perform in a role. Morphing includes components and digital assets such as racial, ethnicity visuals 1506 and/or gender visuals 1508. The conversion engine 1502 converts the visual representations of ethnicity 1506 and gender 1508 selected assets and converts to a 3D wireframe for adding layers of specificity. Once constructed, the morphing combination 1504 occurs. The description and illustration of one or more aspects provided in this application are not intended to limit or restrict the scope of the disclosure as claimed in any way.

Figure 16:
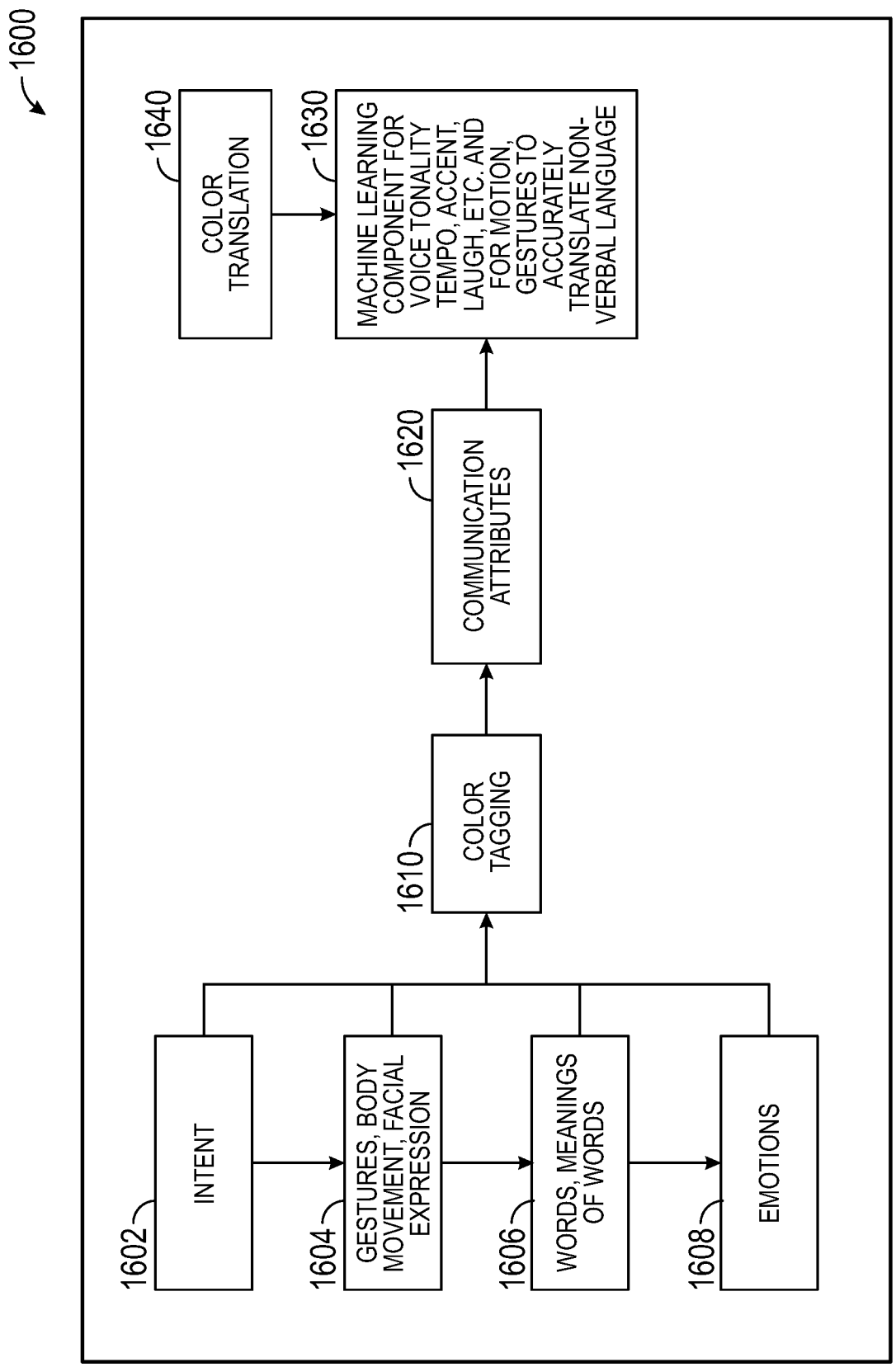
FIG. 16 illustrates asset datastores for use in visualizing an expressive, auto-morphing Metaverse avatar as described herein.

FIG. 16 is an overview of an exemplary input and response processing unit 1600 for creating a Morphing avatar or agent in regard to nonverbal communications regarding intent 1602, gestures, body movements, facial expression 1604, words, meaning of words 1606, and emotions 1608, etc. Each of these components' individual aspect is then colorized with a unique color, and then analyzed independently or collectively and/or in any combination thereof to refine their attributes 1620 for LU characteristics, such as semantics, machine learned techniques and/or natural language processing techniques before applying machine learning 1630 for overall improvement by comparing and contrasting successful non-verbal communications of many users. Color tagging occurs initially as demonstrated in 1610 (additionally in 1340, referring to FIG. 13) with its repository held in 1620 (additionally in 1360B, referring to FIG. 13) and ultimately makes its way through machine learning 1630 to perfect. This diagram shows the repeated process on each communication is regardless of duration and/or disconnected from time and delivered spontaneously. Language Interpretation occurs during the translation process 1640, upon receipt, reversing the order of this diagram to first enter the machine learning 1630 process in a feedback loop system, and then decoding for the language sent in for its attributes 1620, and then the unique color tagged, converted to the properties of intent 1602, gestures, body movements 1604, facial expressions 1606, emotions 1608 and/or haptic experience 1609, as relevant. The description and illustration of one or more aspects provided in this application are not intended to limit or restrict the scope of the disclosure as claimed in any way.

Figure 17:
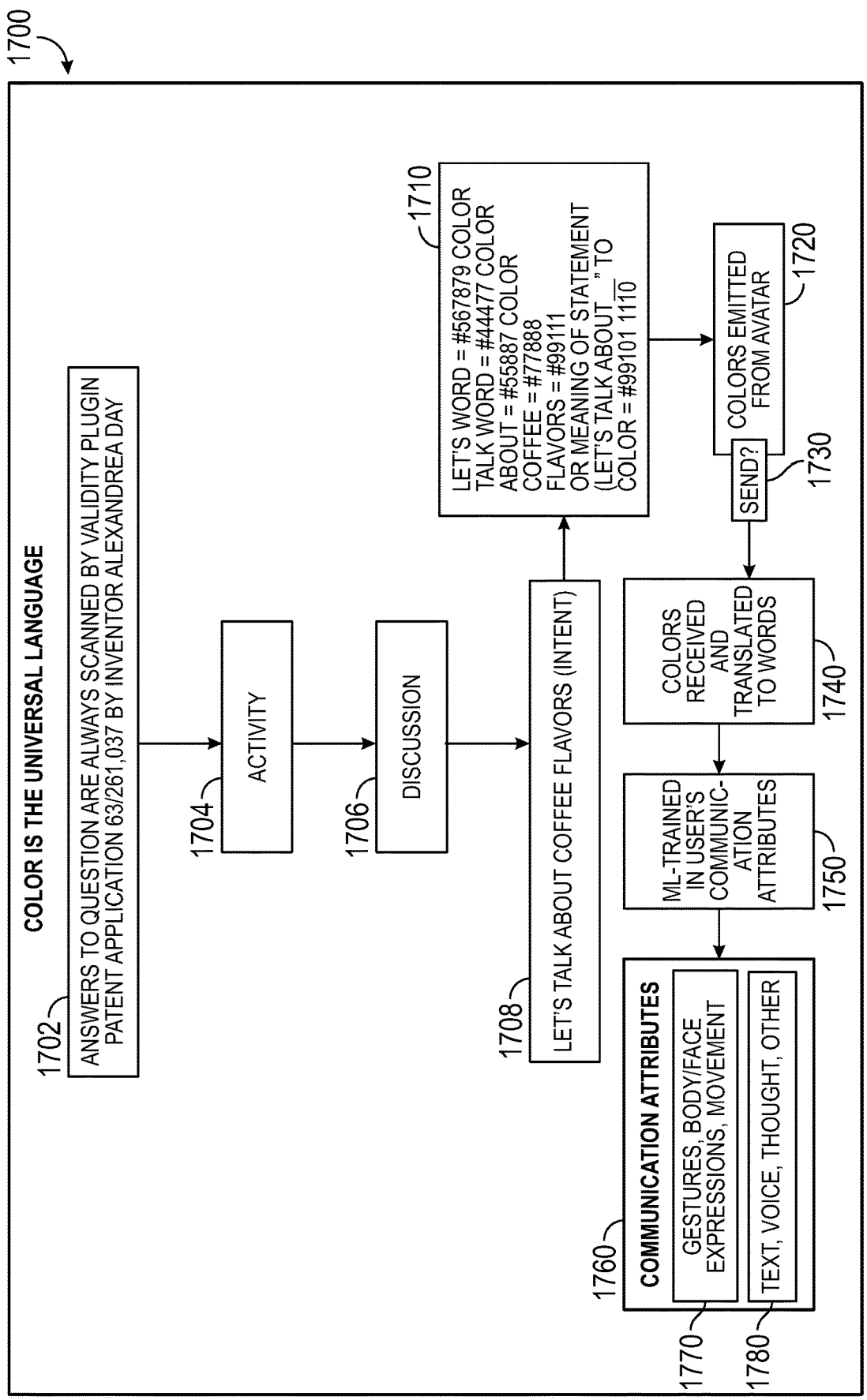
FIG. 17 illustrates the required interactions between words, intent, gestures, movement, facial expression, emotions and haptic experience and colors to create a universal language, and a life-like avatar, agent, as described herein.

FIG. 17 is an overview of an exemplary input and response processing unit 1700 for creating a life-like avatar or agent in regard to nonverbal communications and to combine all communication attributes 1760, including gestures, body movements, facial expression 1770, and text, voice, thought, or other communication components 1780, etc. A specific discussion 1706 ensure based upon an activity 1704, and encodes specific colors to words, or meanings of words 1710 which are then emitted from the avatar 1720, sent 1730, and received within the Metaverse by others 1740, and then translated to the receiver's language to correctly deliver not only the communication attributes in context and other language properties 1750 but also gestures, body/face, movement, with intent, etc. expression 1760, and in any format from text, voice, thought, or other.

In one aspect, a health status validating system is disclosed. The system includes a digital framework including a pattern recognition module configured to measure and validate a change in a health status of a user. The digital framework includes (1) a first digitally recorded library of (i) human emotions, (ii) unconscious agendas, and (iii) physical and mental disease conditions of a control group of users selected from a population of users, to correlate with the emotions, beliefs systems and reported physical and/or mental conditions of the user, (2) a question engine configured to (i) interrogate the user using a second digitally recorded library of predetermined questions, and (ii) identify a plurality of underlying unconscious agendas of the user that generate behavior of the user and associated negative emotions of the user, (3) a baseline measuring module configured to (i) evaluate the user's responses and reactions to the questions posed by the therapist or the question engine, (ii) determine and differentiate between a valid answer and an invalid answer, and thereby (iii) construct a first predictive pattern for a plurality of disease conditions, (4) a reprogramming module configured to (i) reprogram a plurality of negative beliefs of the user, accomplished through relaxation, breathing, recording and repeating a plurality of de-programming and reprogramming statements, (ii) confirm as accurate using the question engine, and thereby (iii) construct a post-reprogramming predictive pattern for a plurality of disease conditions, and (5) a validation module configured to (i) record the first predictive pattern for a plurality of disease conditions, (ii) record the post-reprogramming predictive pattern for a plurality of disease conditions, (iii) compare the first predictive pattern for a plurality of disease conditions and the post-reprogramming predictive pattern for a plurality of disease conditions, and thereby (iv) validate a change in the first predictive pattern for a plurality of disease conditions.

At least one of the baseline measuring module, reprogramming module, and the validation module uses an epigenetic technique to (i) construct the first predictive pattern for a plurality of disease conditions or the post-reprogramming predictive pattern for a plurality of disease conditions, (iii) compare the first predictive pattern for a plurality of disease conditions and the post-reprogramming predictive pattern for a plurality of disease conditions, and (iv) validate a change in the first predictive pattern for a plurality of disease conditions. The epigenetic technique in the health status validating system includes one or more of: measuring gene expression, microarray analysis and reverse transcription polymerase chain reaction (RT-PCR), work by measuring mRNA levels, and Western blot and or other undiscovered or disclosed methods.

Epigenetics is the practice of observing changes in the expression of genes. Epigenetics or any other method are used in this application to observe changes in personality (emotions experience and/or belief systems changed). This invention does not measure what diseases someone has. It predicts what diseases may be in a person's future based upon the emotions they experience frequently based upon the belief systems they hold.

This application is further to recognize and correlate everyone how has a specific disease with their emotions and belief systems, believing that the common experience results in X disease. The correlation is an application—the libraries exist to do the matching the matching itself is the invention—between known diseases and known emotion and human belief systems. This is already known theoretically. For instance, positive people survive cancer at a higher rate, for example. The mapping is the process. The validation of this thesis, people who feel X frequently, and are diagnosed with X, can know and then through that knowledge reprogram their beliefs and reverse their disease condition . . . measured by epigenetic techniques. Did gene expression change after a person changed their mind/emotions? One of the objectives of this application is to predict an unknown disease and or reverse an existing disease.

There are libraries of emotions, their definitions, a library of belief systems, and disease conditions. In additional, in the personal profile of the user, are self-reported, commonly experienced emotions, belief systems and disease conditions. After enough data can be collected and analyzed, we will be able to predict behavior based upon user's self-reported emotions and belief systems.

The purpose of the question engine is to pose a question to the user and wait for the user's answer, and wait again for brainwave analysis of whether the answer is valid or invalid and recording it so. Step 1 is baseline valid, baseline invalid so that following questions can be measure against these pre-determined values.

The health status validating system also includes a plurality of sensors communicably connected to the digital framework and to the user during a question-answer session with a therapist or the question engine, each of the plurality of sensors configured to communicate, record and report at least one of: a physiological state or an emotional state of the user while responding to a plurality of questions posed by the therapist or the question engine during the question-answer session.

The plurality of sensors in the health status validating system includes biometric sensors configured to perform at least one of: detection of eye and/or facial movements, monitoring of pulse, respiration, blood pressure changes, brain waves and/or changes in gene expression of the user.

In one aspect, the pattern recognition module in the health status validating system includes an artificial intelligence architecture configured to analyze the plurality of sensors data in combination with the underlying unconscious agendas of the user. In one aspect, the pattern recognition module in the health status validating system includes a machine learning module configured to train the digital framework based on a set of rules to translate the user's response from a plurality of digitally recorded questions, and to interpret a plurality of outputs from the sensors.

The digital framework in the health status validating system is stored in a secure, distributed storage network include at least one of: a Blockchain application and a distributed database application.

The digital framework in the health status validating system is installed on at least one of: a mobile telephone, a personal digital assistant, a computer and a distributed network system. The digital framework is accessed from the at least one of: the mobile telephone, the personal digital assistant, the computer and the distributed network system. The digital framework is operationalized from the at least one of: the mobile telephone, the personal digital assistant, the computer and the distributed network system.

Figure 18:
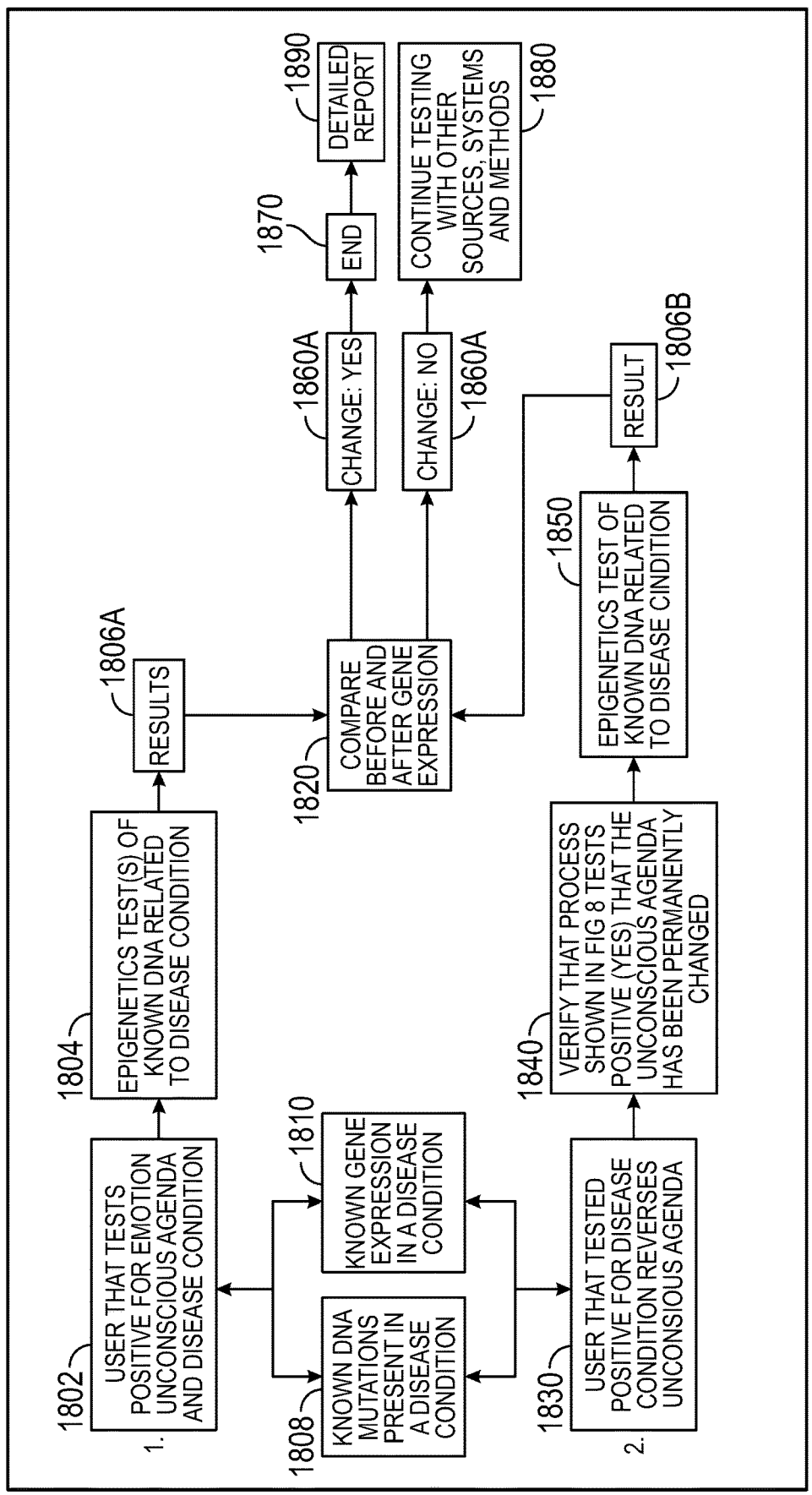
FIG. 18 illustrates a health status validation system including a digital framework that includes a pattern recognition module configured to detect pre-determined associations between specific emotions and unconscious agendas to a specific disease condition by measuring changes in gene expression, of the present disclosure may be practiced.

FIG. 18 illustrates a health status validation system including a digital framework that includes a pattern recognition module configured to detect pre-determined associations between specific emotions and unconscious agendas to a specific disease condition by measuring changes in gene expression, of the present disclosure may be practiced. FIG. 18 further illustrates (1) an epigenetics process that is detailed to establish a baseline for each user and confirm that gene expression anomalies exist in the user that has reported their disease condition, as in 1802. This information has already been cataloged by the Genome Project 1810 and an example would be of a person with primary hypertension that will have gene expression anomalies in one or more of the following genes: AGT AGTR1 ATP2B1 EDNRA NOS2 NOS3 PTGIS SELE. In another embodiment of this application a DNA test may also look for mutations in the same genes. After tests are complete the results 1806A are available for comparison 1820. The method of epigenetics testing 1804 could be one or more different processes including microarray analysis and reverse transcription polymerase chain reaction (RT-PCR), work by measuring mRNA levels, Western blot and/or other techniques developed in the future to measure gene expression and/or changes in gene expression. The next step (2) is performed after each selected test subjects' baseline tests that are included for comparison 1820 have completed the emotional work needed to change the unconscious agendas causing the negative feeling, in the case of primary hypertension could be conflicted. In some embodiments, The second epigenetics and/or DNA test is only conducted after the test subject has successfully been reassessed by system in FIG. 8, as in 1830. In other words, the testee person being tested would no longer feel conflicted and no longer test as conflicted as true and the belief system of being pessimistic and optimistic at the same time will also be changed and validated by the system and method in FIG. 8, as in 1840. In another embodiment, testing blood pressure levels could also be used but in most disease conditions no "test" exists to watch for changes. Results 1806B of epigenetics test 1850 are then compared 1820 with the baseline results and sorted 1860A-B to calculate a detailed report 1890 of the changes. Post report, those with no changes will be reviewed and studied looking for other emotions and unconscious agendas that may be affected by other gene expression changes or DNA mutations not yet available as a known contributor. The description and illustration of one or more aspects provided in this application are not intended to limit or restrict the scope of the disclosure as claimed in any way.

In operation, a method of recording and reporting a health status of a user using a digital framework including a pattern recognition module is disclosed. The method of recording and reporting the health status includes (1) selecting a control group of users from a population of users and digitally recording a plurality of human emotions and unconscious agendas of the control group of users into a library of human emotions and unconscious agendas, (2) digitally recording set of rules related to at least one of: (i) education and training in regard to emotions, unconscious agendas, disease conditions of the control group of users, (ii) communication models for understanding, responses of the control group of users, (iii) a human-tempered response framework, (iv) interpretation of questions posed to the control group of users, and (v) interpretation of answers of the control group of users, and (3) digitally recording a user profile of the user, the user profile includes personal information of the user, personal information includes a list of diagnosed disease conditions, personal life stories, defined traumas throughout life, aspirations, personality traits and preferences, the user's belief systems, record of discovered unconscious agendas, reported diagnosed disease conditions session notes, and/or observation by other humans expressed in reports.

The method of recording and reporting the health status also includes communicably connecting a plurality of sensors to the digital framework and to the user during a question-answer session with a therapist, each of the plurality of sensors communicating, recording and reporting at least one of: a physiological state or an emotional state of the user while responding to a plurality of questions posed by the therapist during the question-answer session.

The digital framework is used to: (i) integrate a first input from the digitally recorded library of human emotions and unconscious agendas, a second input from the digitally recorded set of rules, and a third input from the digitally recorded user profile of the user, and a fourth input from the plurality of sensors, (ii) validate an accuracy of the user's response to the plurality of questions posed by the therapist, based on the first input, the second input, the third input, and the fourth input, wherein the accuracy of the user's response to the plurality of questions posed by the therapist includes a statistical level of confidence score calculated based on data collected from the control group of users or the population of users, (iii) map and predict a disease condition of the user based on the first input, the second input, the third input, and the fourth input, wherein the disease condition includes a medically diagnosed disease condition, and (iv) display and report the predicted disease condition of the user on a visible report or a printable report.

The method also includes the therapist using the set of rules to train the digital framework to ask questions based on a list of emotions and unconscious agendas. The method also includes digitally recording a second library of physical and mental disease conditions that correlate with emotions and beliefs systems of the user.

The communicably connecting a plurality of sensors to the digital framework and to the user includes communicably connecting a plurality of biometric sensors and performing at least one of: detection of eye and/or facial movements, monitoring of pulse, respiration, blood pressure changes, brain waves and/or changes in gene expression of the user.

The method also includes the pattern recognition module using an artificial intelligence architecture to predict the disease condition based on a similarity score or metric that represents the estimated similarity between the control group of users and their reported disease conditions with commonly felt emotions and unconscious agendas.

The method also includes the pattern recognition module using a machine learning module to train the digital framework based on the set of rules to translate the user's response from a plurality of digitally recorded questions, and to interpret a plurality of outputs from the sensors.

The method also includes storing the digitally recorded library of human emotions and unconscious agendas, the digitally recorded set of rules, the digitally recorded user profile of the user, the visible report, and the printable report in a secure, distributed storage network includes at least one of: a Blockchain application and a distributed database application.

The method also includes (i) installing the digital framework on at least one of: a mobile telephone, a personal digital assistant, a computer and a distributed network system, (ii) accessing the digital framework from the at least one of: the mobile telephone, the personal digital assistant, the computer and the distributed network system, and (iii) operationalizing the digital framework is from the at least one of: the mobile telephone, the personal digital assistant, the computer and the distributed network system.

In one aspect, a method of reprogramming a belief system of a user using a digital framework include a pattern recognition module is disclosed. The method includes reprogramming and altering a mental or emotional state of a user using a digital framework comprising a pattern recognition module. The identifying, recommending for reprogramming and altering the mental or emotional state of the user includes (1) interrogating the user using a question engine comprising a library of predetermined questions and identifying a plurality of underlying unconscious agendas of the user that generate behavior of the user and triggered by negative emotions of the user, (2) engaging an expressive, experiential digital agent having digitized color, gestures, expressions, movements, emotions, beliefs, intent, intuition, and haptic effects to interact with the user in real time, to ask questions, to engage the user, and direct the user to perform certain tasks, wherein the digital agent comprises a conversational digital avatar, and a conversational chatbot, (3) communicably connecting a plurality of sensors to the digital framework and to the user during a question-answer session with a therapist or the question engine, each of the plurality of sensors communicating, recording and reporting at least one of: a physiological state or an emotional state of the user while responding to a plurality of questions posed by the therapist, chatbot, avatar, coach, friend or the question engine during the question-answer session, and (4) evaluating the user's responses and reactions to the questions posed by the therapist, chatbot, avatar, coach, friend or the question engine using a baseline measuring module, determining and differentiating between a valid answer and an invalid answer, and thereby constructing a baseline measure for the user, (5) identifying and recommending reprogramming a plurality of negative beliefs of the user through relaxation, breathing, recording and repeating of a plurality of de-programming and reprogramming statements, confirmed as accurate, by the digital framework through an analysis of the plurality of sensors data in combination with the underlying unconscious agendas of the user.

The method of reprogramming a belief system of a user further includes gauging, recording and displaying an engagement level of the user with the therapist or the question engine during the question-answer session.

The method of reprogramming a belief system of a user further includes providing a datastore of assets including a library of digitized options to suggest, offer, validate by a validation engine during the question-answer session.

The method of reprogramming a belief system of a user, wherein the library of digitized options to suggest, offer, validate comprise a plurality of digitized humanizing features comprising empathy, pacing of conversation, offering emotional validation to be offered by the validation engine during the question-answer session.

The method of reprogramming a belief system of a user, wherein the communicably connecting a plurality of sensors to the digital framework and to the user comprises communicably connecting a plurality of biometric sensors and performing at least one of: detection of eye and/or facial movements, monitoring of pulse, respiration, blood pressure changes, brain waves and/or changes in gene expression of the user.

The method of reprogramming a belief system of a user further including a pattern recognition module using an artificial intelligence architecture to analyze the plurality of sensors data in combination with the underlying unconscious agendas of the user.

The method of reprogramming a belief system of a user further including a pattern recognition module using a machine learning module to train the digital framework based on a set of rules to translate the user's response from a plurality of digitally recorded questions and/or suggestions, and to interpret a plurality of outputs from the sensors.

The method of reprogramming a belief system of a user further including storing the digital framework in a secure, distributed storage network comprising at least one of: a block chain application and a distributed database application.

The method of reprogramming a belief system of a user further including installing the digital framework on at least one of: a mobile telephone, a personal digital assistant, a computer and a distributed network system, accessing the digital framework from the at least one of: the mobile telephone, the personal digital assistant, the computer and the distributed network system, and operationalizing the digital framework is from the at least one of: the mobile telephone, the personal digital assistant, the computer and the distributed network system.

In one aspect, a method of validating a health status of a user includes measuring and validating a change in a health status of a user using a digital framework include a pattern recognition module. The measuring and validating the change in the health status of the user includes (1) digitally recording a first library of (i) human emotions, (ii) unconscious agendas, and (iii) physical and mental disease conditions of a control group of users selected from a population of users, to correlate with the emotions, beliefs systems and reported physical and/or mental conditions of the user; (2) interrogating the user using a question engine include a second digitally recorded library of predetermined questions, and identifying a plurality of underlying unconscious agendas of the user that generate behavior of the user and associated negative emotions of the user; (3) evaluating the user's responses and reactions to the questions posed by the therapist or the question engine, determining and differentiating between a valid answer and an invalid answer, and thereby constructing a first predictive pattern for a plurality of disease conditions; (4) reprogramming a plurality of negative beliefs of the user, accomplished through relaxation, breathing, recording and repeating a plurality of de-programming and reprogramming statements, confirm the user's responses as accurate using the question engine, and thereby constructing a post-reprogramming predictive pattern for a plurality of disease conditions; and (5) recording the first predictive pattern for a plurality of disease conditions, recording the post-reprogramming predictive pattern for a plurality of disease conditions, comparing the first predictive pattern for a plurality of disease conditions and the post-reprogramming predictive pattern for a plurality of disease conditions, and thereby validating a change in the first predictive pattern for a plurality of disease conditions.

The at least one of: the constructing a first predictive pattern for a plurality of disease conditions, constructing a post-reprogramming predictive pattern for a plurality of disease conditions, and validating a change in the first predictive pattern for a plurality of disease conditions comprises using epigenetic technique to construct the first predictive pattern for a plurality of disease conditions, construct the post-reprogramming predictive pattern for a plurality of disease conditions, and validate the change in the first predictive pattern for a plurality of disease conditions. The epigenetic technique includes one or more of: a method of measuring gene expression, microarray analysis and reverse transcription polymerase chain reaction (RT-PCR), work by measuring mRNA levels, and Western blot technique.

The method of validating a health status of a user further include communicably connecting a plurality of sensors to the digital framework and to the user during a question-answer session with a therapist or the question engine, each of the plurality of sensors communicating, recording and reporting at least one of: a physiological state or an emotional state of the user while responding to a plurality of questions posed by the therapist or the question engine during the question-answer session.

The method of validating a health status of the user, wherein the communicably connecting a plurality of sensors to the digital framework and to the user includes communicably connecting a plurality of biometric sensors and performing at least one of: detection of eye and/or facial movements, monitoring of pulse, respiration, blood pressure changes, brain waves and/or changes in gene expression of the user.

The method of validating a health status of the user further including the pattern recognition module using an artificial intelligence architecture to analyze the plurality of sensors data in combination with the underlying unconscious agendas of the user.

The method of validating a health status of the user further including the pattern recognition module using a machine learning module to train the digital framework based on a set of rules to translate the user's response from a plurality of digitally recorded questions, and to interpret a plurality of outputs from the sensors.

The method of validating a health status of a user further including storing the digital framework in a secure, distributed storage network include at least one of: a Blockchain application and a distributed database application.

The method of validating a health status of a user further including installing the digital framework on at least one of: a mobile telephone, a personal digital assistant, a computer and a distributed network system, accessing the digital framework from the at least one of: the mobile telephone, the personal digital assistant, the computer and the distributed network system, and operationalizing the digital framework is from the at least one of: the mobile telephone, the personal digital assistant, the computer and the distributed network system.

In one aspect, a non-transitory machine-readable storage medium including instructions embodied thereon for recording and reporting a health status of a user is disclosed. The instructions when executed using one or more computer processors causes the machine to perform recording and reporting the health status of the user using a digital framework includes a pattern recognition module configured to, the recording and reporting the health status includes: (1) selecting a control group of users from a population of users and digitally recording a plurality of human emotions and unconscious agendas of the control group of users into a library of human emotions and unconscious agendas; (2) digitally recording set of rules related to at least one of: (i) education and training in regard to emotions, unconscious agendas, disease conditions of the control group of users, (ii) communication models for understanding, responses of the control group of users, (iii) a human-tempered response framework, (iv) interpretation of questions posed to the control group of users, and (v) interpretation of answers of the control group of users; and (3) digitally recording a user profile of the user, the user profile includes personal information of the user, personal information includes a list of diagnosed disease conditions, personal life stories, defined traumas throughout life, aspirations, personality traits and preferences, the user's belief systems, record of discovered unconscious agendas, reported diagnosed disease conditions session notes, and/or observation by other humans expressed in reports.

The non-transitory machine-readable storage medium including instructions embodied thereon for recording and reporting a health status of a user, the instructions when executed using one or more computer processors further causes the machine to perform communicably connecting a plurality of sensors to the digital framework and to the user during a question-answer session with a therapist, each of the plurality of sensors communicating, recording and reporting at least one of: a physiological state or an emotional state of the user while responding to a plurality of questions posed by the therapist during the question-answer session.

The digital framework is configured to: (i) integrate a first input from the digitally recorded library of human emotions and unconscious agendas, a second input from the digitally recorded set of rules, and a third input from the digitally recorded user profile of the user, and a fourth input from the plurality of sensors, (ii) validate an accuracy of the user's response to the plurality of questions posed by the therapist, based on the first input, the second input, the third input, and the fourth input, wherein the accuracy of the user's response to the plurality of questions posed by the therapist includes a statistical level of confidence score calculated based on data collected from the control group of users or the population of users, (iii) map and predict a disease condition of the user based on the first input, the second input, the third input, and the fourth input, wherein the disease condition includes a medically diagnosed disease condition, and (iv) display and report the predicted disease condition of the user on a visible report or a printable report.

The non-transitory machine-readable storage medium further includes engaging the therapist using the set of rules to train the digital framework to ask questions based on a list of emotions and unconscious agendas.

The non-transitory machine-readable storage medium further includes digitally recording a second library of physical and mental disease conditions that correlate with emotions and beliefs systems of the user.

The communicably connecting a plurality of sensors to the digital framework and to the user includes communicably connecting a plurality of biometric sensors and performing at least one of: detection of eye and/or facial movements, monitoring of pulse, respiration, blood pressure changes, brain waves and/or changes in gene expression of the user.

The non-transitory machine-readable storage medium further includes the pattern recognition module using an artificial intelligence architecture to predict the disease condition based on a similarity score or metric that represents the estimated similarity between the control group of users and their reported disease conditions with commonly felt emotions and unconscious agendas.

The non-transitory machine-readable storage medium further includes the pattern recognition module using a machine learning module to train the digital framework based on the set of rules to translate the user's response from a plurality of digitally recorded questions, and to interpret a plurality of outputs from the sensors.

The non-transitory machine-readable storage medium further includes storing the digitally recorded library of human emotions and unconscious agendas, the digitally recorded set of rules, the digitally recorded user profile of the user, the visible report, and the printable report in a secure, distributed storage network includes at least one of: a Blockchain application and a distributed database application.

The non-transitory machine-readable storage medium further includes (i) installing the digital framework on at least one of: a mobile telephone, a personal digital assistant, a computer and a distributed network system, (ii) accessing the digital framework from the at least one of: the mobile telephone, the personal digital assistant, the computer and the distributed network system, and (iii) operationalizing the digital framework from the at least one of: the mobile telephone, the personal digital assistant, the computer and the distributed network system.

In one aspect, a non-transitory machine-readable storage medium, including instructions embodied thereon for reprogramming and altering an emotional or mental belief system of a user is disclosed. The instructions when executed using one or more computer processors causes the machine to perform identifying and recommending reprogramming and altering a mental or emotional state of a user using a digital framework comprising a pattern recognition module, the identifying and recommending reprogramming and altering a mental or emotional state of a user using a digital framework comprising a pattern recognition module includes (1) interrogating the user using a question engine include a library of predetermined questions and identifying a plurality of underlying unconscious agendas of the user that generate behavior of the user and associated negative emotions of the user; (2) engaging an expressive, experiential digital agent having digitized color, gestures, expressions, movements, emotions, beliefs, intent, intuition, and haptic effects to interact with the user in real time, to ask questions, to engage the user, and direct the user to perform certain tasks, wherein the digital agent includes a conversational digital avatar, and a conversational chatbot; (3) communicably connecting a plurality of sensors to the digital framework and to the user during a question-answer session with a therapist or the question engine, each of the plurality of sensors communicating, recording and reporting at least one of: a physiological state or an emotional state of the user while responding to a plurality of questions posed by the therapist or the question engine during the question-answer session; (4) evaluating the user's responses and reactions to the questions posed by the therapist or the question engine using a baseline measuring module, determining and differentiating between a valid answer and an invalid answer, and thereby constructing a baseline measure for the user; and (5) identifying and recommending reprogramming a plurality of negative beliefs of the user through relaxation, breathing, recording and repeating of a plurality of de-programming and reprogramming statements, confirmed as accurate, by the digital framework through an analysis of the plurality of sensors data in combination with the underlying unconscious agendas of the user.

The non-transitory machine-readable storage medium further includes gauging, recording and displaying an engagement level of the user with the therapist, chatbot, avatar, coach, friend, or the question engine during the question-answer session.

The non-transitory machine-readable storage medium further includes providing a datastore of assets including a library of digitized options to suggest, offer, validate by the validation engine during the question-answer session.

The non-transitory machine-readable storage medium wherein the library of digitized options to suggest, offer, validate comprise a plurality of digitized humanizing features comprising empathy, pacing of conversation, offering validation by the validation engine during the question-answer session.

The non-transitory machine-readable storage medium wherein the communicably connecting a plurality of sensors to the digital framework and to the user comprises communicably connecting a plurality of biometric sensors and performing at least one of: detection of eye and/or facial movements, monitoring of pulse, respiration, blood pressure changes, brain waves and/or changes in gene expression of the user.

The non-transitory machine-readable storage medium further including the pattern recognition module using an artificial intelligence architecture to analyze the plurality of sensors data in combination with the underlying unconscious agendas of the user.

The non-transitory machine-readable storage medium further including the pattern recognition module using a machine learning module to train the digital framework based on a set of rules to translate the user's response from a plurality of digitally recorded questions and suggestions, and to interpret a plurality of outputs from the sensors.

The non-transitory machine-readable storage medium further including storing the digital framework in a secure, distributed storage network comprising at least one of: a block chain application and a distributed database application.

The non-transitory machine-readable storage medium further including (1) installing the digital framework on at least one of: a mobile telephone, a personal digital assistant, a computer and a distributed network system, (2) accessing the digital framework from the at least one of: the mobile telephone, the personal digital assistant, the computer and the distributed network system, and (3) operationalizing the digital framework is from the at least one of: the mobile telephone, the personal digital assistant, the computer and the distributed network system.

In one aspect, a non-transitory machine-readable storage medium, including instructions embodied thereon for validating and reporting a health status of a user is disclosed. The instructions when executed using one or more computer processors causes the machine to perform: measuring and validating a change in a health status of a user using a digital framework include a pattern recognition module. The measuring and validating the change in the health status of the user include: (1) digitally recording a first library of (i) human emotions, (ii) unconscious agendas, and (iii) physical and mental disease conditions of a control group of users selected from a population of users, to correlate with the emotions, beliefs systems and reported physical and/or mental conditions of the user; (2) interrogating the user using a question engine include a second digitally recorded library of predetermined questions, and identifying a plurality of underlying unconscious agendas of the user that generate behavior of the user and associated negative emotions of the user; (3) evaluating the user's responses and reactions to the questions posed by the therapist or the question engine, determining and differentiating between a valid answer and an invalid answer, and thereby constructing a first predictive pattern for a plurality of disease conditions; (4) reprogramming a plurality of negative beliefs of the user, accomplished through relaxation, breathing, recording and repeating a plurality of de-programming and reprogramming statements, confirm the user's responses as accurate using the question engine, and thereby constructing a post-reprogramming predictive pattern for a plurality of disease conditions; and (5) recording the first predictive pattern for a plurality of disease conditions, recording the post-reprogramming predictive pattern for a plurality of disease conditions, comparing the first predictive pattern for a plurality of disease conditions and the post-reprogramming predictive pattern for a plurality of disease conditions, and thereby validating a change in the first predictive pattern for a plurality of disease conditions.

At least one of: the constructing a first predictive pattern for a plurality of disease conditions, constructing a post-reprogramming predictive pattern for a plurality of disease conditions, and validating a change in the first predictive pattern for a plurality of disease conditions comprises using epigenetic technique to construct the first predictive pattern for a plurality of disease conditions, construct the post-reprogramming predictive pattern for a plurality of disease conditions, and validate the change in the first predictive pattern for a plurality of disease conditions.

The using epigenetic technique includes using one or more of: a method of measuring gene expression, microarray analysis and reverse transcription polymerase chain reaction (RT-PCR), work by measuring mRNA levels, and Western blot technique.

The non-transitory machine-readable storage medium further including communicably connecting a plurality of sensors to the digital framework and to the user during a question-answer session with a therapist or the question engine, each of the plurality of sensors communicating, recording and reporting at least one of: a physiological state or an emotional state of the user while responding to a plurality of questions posed by the therapist or the question engine during the question-answer session.

The non-transitory machine-readable storage medium, wherein the communicably connecting a plurality of sensors to the digital framework and to the user includes communicably connecting a plurality of biometric sensors and performing at least one of: detection of eye and/or facial movements, monitoring of pulse, respiration, blood pressure changes, brain waves and/or changes in gene expression of the user.

The non-transitory machine-readable storage medium further including the pattern recognition module using an artificial intelligence architecture to analyze the plurality of sensors data in combination with the underlying unconscious agendas of the user.

The non-transitory machine-readable storage medium further including the pattern recognition module using a machine learning module to train the digital framework based on a set of rules to translate the user's response from a plurality of digitally recorded questions, and to interpret a plurality of outputs from the sensors.

The non-transitory machine-readable storage medium further including storing the digital framework in a secure, distributed storage network include at least one of: a Blockchain application and a distributed database application.

The non-transitory machine-readable storage medium further including installing the digital framework on at least one of: a mobile telephone, a personal digital assistant, a computer and a distributed network system, accessing the digital framework from the at least one of: the mobile telephone, the personal digital assistant, the computer and the distributed network system, and operationalizing the digital framework is from the at least one of: the mobile telephone, the personal digital assistant, the computer and the distributed network system.

While the disclosure has been described in terms of exemplary embodiments, those skilled in the art will recognize that the disclosure can be practiced with modifications in the spirit and scope of the appended claim, drawings and attachment. The examples provided herein are merely illustrative and are not meant to be an exhaustive list of all possible designs, embodiments, applications or modifications of the disclosure.

What is claimed is:

1. An emotional or mental belief system reprogramming system, the system comprising one or more computer processors configured to provide:
   a digital framework comprising a pattern recognition module configured to identify and recommend reprogramming and alter a health status of a user, the digital framework comprising:
   a digitally recorded library of human emotions, unconscious agendas, perceptions, beliefs, and mindsets of a control group of users selected from a population of users;
   a question engine configured to interrogate the user using a library of predetermined questions and to identify a plurality of underlying unconscious agendas of the user that generate behavior of the user and associated negative emotions of the user;
   an expressive, experiential digital agent having digitized color, gestures, expressions, movements, emotions, beliefs, intent, intuition, and haptic effects, the digital agent configured to interact with the user in real time, to ask questions, to engage the user, and to direct the user to perform certain tasks, wherein the digital agent comprises a conversational digital avatar, or a conversational chatbot;
   a plurality of sensors communicably connected to the digital framework and to the user during a question-answer session with a therapist, chatbot, avatar, coach, or friend as a means of engaging the question engine, each of the plurality of sensors configured to communicate, record and report at least one of: a physiological state or an emotional state of the user while responding to a plurality of questions posed by the therapist, chatbot, avatar, coach, or friend as a means of engaging the question engine during the question-answer session;
   a baseline measuring module configured to evaluate the user's responses and reactions to the questions posed by the therapist, chatbot, avatar, coach, or friend as a means of engaging the question engine, and to determine and differentiate between a valid answer and an invalid answer, and thereby to construct a baseline measure for the user; and
   a reprogramming module configured to identify and recommend reprogramming of a plurality of negative beliefs of the user, accomplished through relaxation, breathing, recording and repeating a plurality of de-programming and reprogramming statements, confirmed as accurate, by the digital framework through an analysis of the plurality of sensors data in combination with the underlying unconscious agendas of the user.

2. The system of claim 1 further comprising a user engagement level gauge configured to record and display the user's engagement level with the therapist, chatbot, avatar, coach, or friend during the question-answer session.

3. The system of claim 1 further comprising a datastore of assets comprising:
a library of digitized options to suggest, offer to a user and validated, or not, by a validation engine, during the question-answer session.

4. The system of claim 3, wherein the library of digitized options to suggest, offer, validate comprises a plurality of digitized humanizing features comprising empathy, pacing of conversation, offering emotional validation to be offered by the therapist or the question engine during the question-answer session.

5. The system of claim 1, wherein the plurality of sensors comprise biometric sensors configured to perform at least one of: detection of eye or facial movements, monitoring of pulse, respiration, blood pressure changes, brain waves or changes in gene expression of the user.

6. The system of claim 1, wherein the pattern recognition module comprises an artificial intelligence architecture configured to analyze the plurality of sensors data in combination with the underlying unconscious agendas of the user.

7. The system of claim 1, wherein the pattern recognition module comprises a machine learning module configured to train the digital framework based on a set of rules to translate the user's response from a plurality of digitally recorded questions or suggested answers, and to interpret a plurality of outputs from the sensors.

8. The system of claim 1, wherein the digital framework is stored in a secure, distributed storage network comprising at least one of: a block chain application and a distributed database application.

9. The system of claim 1, wherein the digital framework is installed on at least one of: a mobile telephone, a personal digital assistant, a computer and a distributed network system,
wherein the digital framework is accessed from the at least one of: the mobile telephone, the personal digital assistant, the computer and the distributed network system, and
wherein the digital framework is operationalized from the at least one of: the mobile telephone, the personal digital assistant, the computer and the distributed network system.

10. A method of reprogramming a belief system of a user, the method comprising:
reprogramming and altering a mental or emotional state of a user using a digital framework comprising a pattern recognition module, the identifying, recommending for reprogramming and altering the mental or emotional state of the user comprising:
interrogating the user using a question engine comprising a library of predetermined questions and identifying a plurality of underlying unconscious agendas of the user that generate behavior of the user and triggered by negative emotions of the user;
engaging an expressive, experiential digital agent having digitized color, gestures, expressions, movements, emotions, beliefs, intent, intuition, and haptic effects to interact with the user in real time, to ask questions, to engage the user, and direct the user to perform certain tasks, wherein the digital agent comprises a conversational digital avatar, and a conversational chatbot;
communicably connecting a plurality of sensors to the digital framework and to the user during a question-answer session with a therapist or the question engine, each of the plurality of sensors communicating, recording and reporting at least one of: a physiological state or an emotional state of the user while responding to a plurality of questions posed by the therapist, chatbot, avatar, coach, friend or the question engine during the question-answer session;
evaluating the user's responses and reactions to the questions posed by the therapist, chatbot, avatar, coach, friend or the question engine using a baseline measuring module, determining and differentiating between a valid answer and an invalid answer, and thereby constructing a baseline measure for the user;
identifying and recommending reprogramming a plurality of negative beliefs of the user through relaxation, breathing, recording and repeating of a plurality of de-programming and reprogramming statements, confirmed as accurate, by the digital framework through an analysis of the plurality of sensors data in combination with the underlying unconscious agendas of the user.

11. The method of claim 10 further comprising gauging, recording and displaying an engagement level of the user with the therapist or the question engine during the question-answer session.

12. The method of claim 10 further comprising providing a datastore of assets comprising:
a library of digitized options to suggest, offer, validate by a validation engine during the question-answer session.

13. The method of claim 12, wherein the library of digitized options to suggest, offer, validate comprise a plurality of digitized humanizing features comprising empathy, pacing of conversation, offering emotional validation to be offered by the validation engine during the question-answer session.

14. The method of claim 10, wherein the communicably connecting a plurality of sensors to the digital framework and to the user comprises communicably connecting a plurality of biometric sensors and performing at least one of: detection of eye or facial movements, monitoring of pulse, respiration, blood pressure changes, brain waves or changes in gene expression of the user.

15. The method of claim 10 further comprising the pattern recognition module using an artificial intelligence architecture to analyze the plurality of sensors data in combination with the underlying unconscious agendas of the user.

16. The method of claim 10 further comprising the pattern recognition module using a machine learning module to train the digital framework based on a set of rules to translate the user's response from a plurality of digitally recorded questions or suggestions, and to interpret a plurality of outputs from the sensors.

17. The method of claim 10 further comprising storing the digital framework in a secure, distributed storage network comprising at least one of: a block chain application and a distributed database application.

18. The method of claim 10 further comprising:
installing the digital framework on at least one of: a mobile telephone, a personal digital assistant, a computer and a distributed network system, accessing the digital framework from the at least one of: the mobile telephone, the personal digital assistant, the computer and the distributed network system, and operationalizing the digital framework is from the at least one of: the mobile telephone, the personal digital assistant, the computer and the distributed network system.

19. A non-transitory machine-readable storage medium, comprising instructions embodied thereon for reprogramming and altering an emotional or mental belief system of a user, the instructions when executed using one or more computer processors causes the machine to perform:

identifying and recommending reprogramming and altering a mental or emotional state of a user using a digital framework comprising a pattern recognition module, the identifying and recommending reprogramming the mental or emotional state of the user comprising:

interrogating the user using a question engine comprising a library of predetermined questions and identifying a plurality of underlying unconscious agendas of the user that generate behavior of the user and, triggered by the negative emotions of the user;

engaging an expressive, experiential digital agent having digitized color, gestures, expressions, movements, emotions, beliefs, intent, intuition, and haptic effects to interact with the user in real time, to ask questions, to engage the user, and direct the user to perform certain tasks, wherein the digital agent comprises a conversational digital avatar, and a conversational chatbot;

communicably connecting a plurality of sensors to the digital framework and to the user during a question-answer session with a therapist or the question engine, each of the plurality of sensors communicating, recording and reporting at least one of: a physiological state or an emotional state of the user while responding to a plurality of questions posed by the therapist or the question engine during the question-answer session;

evaluating the user's responses and reactions to the questions posed by the therapist or the question engine using a baseline measuring module, determining and differentiating between a valid answer and an invalid answer, and thereby constructing a baseline measure for the user;

identifying and recommending reprogramming a plurality of negative beliefs of the user through relaxation, breathing, recording and repeating of a plurality of de-programming and reprogramming statements, confirmed as accurate, by the digital framework through an analysis of the plurality of sensors data in combination with the underlying unconscious agendas of the user.

20. The non-transitory machine-readable storage medium of claim 19 further comprising gauging, recording and displaying an engagement level of the user with the therapist, chatbot, avatar, coach, friend, or the question engine during the question-answer session.

21. The non-transitory machine-readable storage medium of claim 19 further comprising providing a datastore of assets comprising:

a library of digitized options to suggest, offer, validate by the validation engine during the question-answer session.

22. The non-transitory machine-readable storage medium of claim 21, wherein the library of digitized options to suggest, offer, validate comprise a plurality of digitized humanizing features comprising empathy, pacing of conversation, offering validation by the validation engine during the question-answer session.

23. The non-transitory machine-readable storage medium of claim 19, wherein the communicably connecting a plurality of sensors to the digital framework and to the user comprises communicably connecting a plurality of biometric sensors and performing at least one of: detection of eye or facial movements, monitoring of pulse, respiration, blood pressure changes, brain waves or changes in gene expression of the user.

24. The non-transitory machine-readable storage medium of claim 19 further comprising the pattern recognition module using an artificial intelligence architecture to analyze the plurality of sensors data in combination with the underlying unconscious agendas of the user.

25. The non-transitory machine-readable storage medium of claim 19 further comprising the pattern recognition module using a machine learning module to train the digital framework based on a set of rules to translate the user's response from a plurality of digitally recorded questions and suggestions, and to interpret a plurality of outputs from the sensors.

26. The non-transitory machine-readable storage medium of claim 19 further comprising storing the digital framework in a secure, distributed storage network comprising at least one of: a block chain application and a distributed database application.

27. The non-transitory machine-readable storage medium of claim 19 further comprising:

installing the digital framework on at least one of: a mobile telephone, a personal digital assistant, a computer and a distributed network system, accessing the digital framework from the at least one of: the mobile telephone, the personal digital assistant, the computer and the distributed network system, and operationalizing the digital framework is from the at least one of: the mobile telephone, the personal digital assistant, the computer and the distributed network system.

\* \* \* \* \*